(12) United States Patent
Kingston et al.

(10) Patent No.: US 10,273,529 B2
(45) Date of Patent: Apr. 30, 2019

(54) ISOLATION OF FACTORS THAT ASSOCIATE DIRECTLY OR INDIRECTLY WITH NON-CODING RNAS

(75) Inventors: Robert Kingston, Arlington, MA (US); Matthew Simon, New Haven, CT (US); Jason Allen West, Somerville, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 700 days.

(21) Appl. No.: 14/239,369

(22) PCT Filed: Aug. 20, 2012

(86) PCT No.: PCT/US2012/051565
§ 371 (c)(1),
(2), (4) Date: Jul. 30, 2014

(87) PCT Pub. No.: WO2013/028611
PCT Pub. Date: Feb. 28, 2013

(65) Prior Publication Data
US 2015/0056615 A1    Feb. 26, 2015

Related U.S. Application Data

(60) Provisional application No. 61/525,559, filed on Aug. 19, 2011.

(51) Int. Cl.
*C12Q 1/68* (2018.01)
*C12Q 1/6834* (2018.01)
(Continued)

(52) U.S. Cl.
CPC ......... *C12Q 1/6834* (2013.01); *C12Q 1/6809* (2013.01); *C12Q 1/6811* (2013.01); *C12Q 1/6813* (2013.01); *C12Q 1/6876* (2013.01)

(58) Field of Classification Search
None
See application file for complete search history.

(56) References Cited

U.S. PATENT DOCUMENTS

| | | | | |
|---|---|---|---|---|
| 2003/0228615 A1* | 12/2003 | Rossi | ................ | C12N 15/1096 435/6.11 |
| 2012/0115237 A1* | 5/2012 | Smart | ................ | C12Q 1/6844 436/86 |
| 2013/0123123 A1* | 5/2013 | Chang | ................ | C12Q 1/6876 506/9 |

FOREIGN PATENT DOCUMENTS

| | | |
|---|---|---|
| JP | 2011147412 A | 8/2011 |
| WO | 2003054162 A2 | 7/2003 |

(Continued)

OTHER PUBLICATIONS

Ho et al. (1998) "Mapping of RNA accessible sites for antisense experiments with oligonucleotide libraries" Nature Biotechnology 16:59-63.*

(Continued)

*Primary Examiner* — Karen S. Weiler
(74) *Attorney, Agent, or Firm* — Nixon Peabody LLP; David S. Resnick; Shayne Y. Huff

(57) ABSTRACT

Methods and assays are provided for isolating factors including polypeptides, ribonucleic acids (RNAs) and polypeptide complexes that are associated with a target nucleic acid sequence. The target nucleic acid sequence may be comprised within chromatin. The methods are suitable for identification and characterisation of factors including non-coding RNAs (ncRNAs) that associate with specified genomic loci.

15 Claims, 30 Drawing Sheets
Specification includes a Sequence Listing.

(51) Int. Cl.
 *C12Q 1/6813* (2018.01)
 *C12Q 1/6876* (2018.01)
 *C12Q 1/6809* (2018.01)
 *C12Q 1/6811* (2018.01)

(56) References Cited

FOREIGN PATENT DOCUMENTS

| WO | 2008024499 A2 | 2/2008 |
| WO | 2009024781 A1 | 2/2009 |
| WO | 2010093860 A2 | 8/2010 |

OTHER PUBLICATIONS

Iioka et al., Nucleic Acids Research, 39(8):e53 (2011). "RNA-protein interactions using tethered RNAs."

Miglino et al., Journal of Virological Methods, 146(1-2): 2007. "A semi-automated and highly sensitive streptavidin magnetic capture-hybridization RT-PCR assay: Application to genus-wide or species-specific detection of several viruses of ornamental bulb crops."

Wages et al., Biotechniques, 23(6):1116 (1997). "Affinity purification of RNA: Sequence-specific capture by nonionic morpholino probes."

Tahira et al., "Long noncoding intronic RNAs are differentially expressed in primary and metastatic pancreatic cancer", Molecular Cancer 10:141 (2011). (19 pages).

Hung, T. and Chang, H.Y., RNA Biol., 7(5):582-585 (2010): "Long Noncoding RNA in Genome Regulation: Prospects and Mechanisms."

* cited by examiner

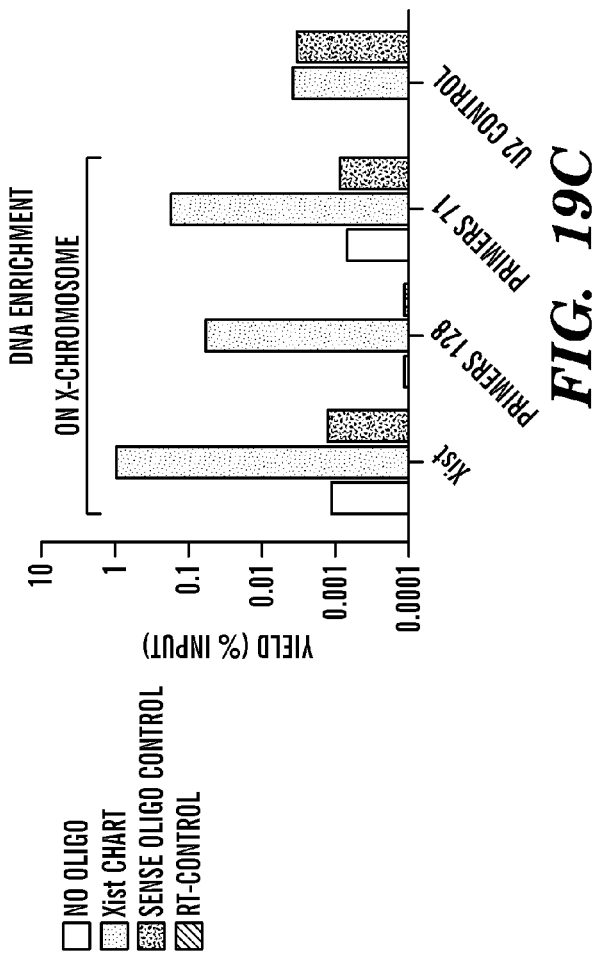
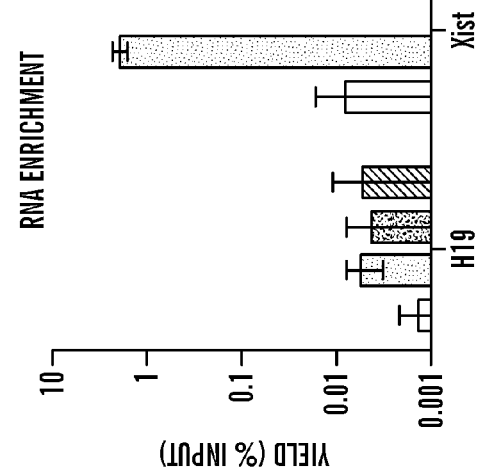
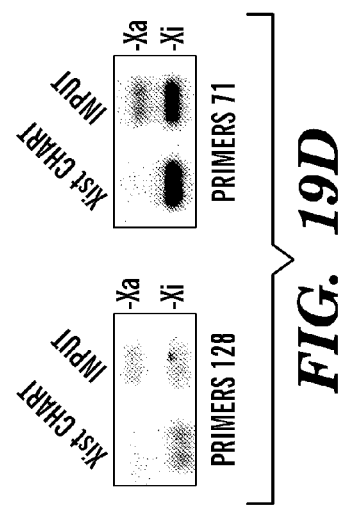
FIG. 19B
FIG. 19C
FIG. 19D

SEQUENCE LISTING

<160> NUMBER OF SEQ ID NOS: 54

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
taacaccaat ttaccctttc gatg                                          24

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
tctcactgtc cgtaagacaa ttcaa                                         25

<210> SEQ ID NO 3
<211> LENGTH: 25

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctcttgcttg attttgcttc ggaga                                            25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
taatggctcc tacatactac atct                                             24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
catcgaaagg gtaaattggt gtta                                             24

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ttgaattgtc ttacggacag tgaga                                            25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tctccgaagc aaaatcaagc aagag                                            25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gctaggactc acactggcca gggac                                            25

<210> SEQ ID NO 9
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 9
tccatgtctc ccggttccat ctgct                                          25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
catgaagcat ttttgtaact ttcag                                          25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ggactctggg aaacctgggc tcccg                                          25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gaggcgtcag aggggacctg ccttc                                          25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gctgctcccc gcctgagccc cgggg                                          25

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agctcggatg gccatcga                                                  18

<210> SEQ ID NO 15
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 15
cgttactctt gcttgatttt gc                                              22

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cattgataat cgttcgaaac gttc                                            24

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gacaagcgcg tcaacc                                                     16

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tgtcttggaa cgcaacatt                                                  19

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcatatatat ttgcttaatt tgcaacat                                        28

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtgggcctgc agccatccag                                                 20

<210> SEQ ID NO 21
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 21
gcgggctctc tcctccaggg                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggggcggatc ggtgttgctt                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cccggttcca tctgctcgcc                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agcccgggac agtaagccga                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tccccaccct ctctgcaggc                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cagctcctcg ttggagaagt                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 27
aagcctccat tcccaagaac                                               20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tcgccgaacc ccaacaccaa                                               20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcgcggtgtt catcggccat                                               20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gttggcggag tgcttgccct                                               20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cggacgcaga agtcctcgcc                                               20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccgcttgcga tgcaaacgcc                                               20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atgtggcggt acgcggatgc                                           20

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agagcgagat agttggaag                                            19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tcaagttgag atcgcttcg                                            19

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gaccggatta ctgggtttcg c                                         21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
catatggccg atcaagtgct c                                         21

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aacggcgtag tgggaggcca                                           20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 39
ccgcccacca cagctgtctg                                              20

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
caatcagcag attctccggc t                                            21

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
agccgcactc gcgcttctac                                              20

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
agctcggatg gccatcga                                                18

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cgttactctt gcttgatttt gc                                           22

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tcagtagttg tcaccggctt g                                            21

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
```
cccgccaaga agaagctctc                                                  20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
aaggtgaagg tcggagtcaa                                                  20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggaagatggt gatgggattt                                                  20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cgcaactggc ctctcctgcc                                                  20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ctcgtcgctg cgtcccaagg                                                  20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ggggcggatc ggtgttgctt                                                  20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51

```
cccggttcca tctgctcgcc                                                    20

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cgccatttta tagacttctg agcag                                              25

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cccttaaagc cacgggggac cgcgc                                              25

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ctcggtctct cgaatcggat ccgac                                              25
```

ISOLATION OF FACTORS THAT ASSOCIATE DIRECTLY OR INDIRECTLY WITH NON-CODING RNAS

CROSS-REFERENCE TO RELATED APPLICATIONS

This application is a 35 U.S.C. § 371 National Phase Entry Application of International Application No. PCT/US2012/051565 filed Aug. 20, 2012, which designates the U.S., and which claims benefit under 35 U.S.C. § 119(e) of U.S. Provisional Application No. 61/525,559, filed Aug. 19, 2011, the contents of each of which are incorporated herein by reference in their entirety.

GOVERNMENT SUPPORT

This invention was made with Government support under National Institutes of Health Grants NIH grant GM043901 and GM045744. The Government has certain rights in this invention.

SEQUENCE LISTING

The instant application contains a Sequence Listing which has been submitted electronically in ASCII format and is hereby incorporated by reference in its entirety. Said ASCII copy, created on Feb. 26, 2014, is named 030258-071492-US_SL.txt and is 12,746 bytes in size.

FIELD

The invention relates to assays for factors that associate with nucleic acid sequences, particularly genomic DNA, RNA and chromatin. In addition, novel chromatin associated factors identified by the assay are provided.

BACKGROUND

Epigenetics concerns the transmission of information from a cell or multicellular organism to its descendants without that information being encoded in the nucleotide sequence of genes. Epigenetic mechanisms can operate through chemical modification of the DNA or through post translational modifications to proteins and polypeptides associated with the DNA. RNAs, including long non-coding RNAs have also been implicated in epigenetic regulation.

The location and identity of nucleic acid sequences is critical to information storage and regulation of cell state; this is particularly evident in the regulation of chromatin structure and function. For example, the genomes of eukaryotic cells, DNA is associated with protein and ribonucleic acid (RNA) complexes that assist in regulating gene expression, packaging of the DNA and controlling replication. The myriad of factors that are associated with the genome contribute to what is termed chromatin: the nuclear material present in the nucleus of most eukaryotic cells. At various times in the cell cycle the level of packaging (or condensation) of the genomic DNA can vary between a lower packaged state such as during replication of the DNA (S Phase) to a more condensed state such as during cell division (M phase) where the genome is packaged into chromosomes. Highly expressed genes also tend to exist in a state of low packaging (so called euchromatic state), whereas silenced genes exist in a state of high packaging (so called heterochromatic state). The relative state of condensation, maintenance of this state and the transition between heterochromatin and euchromatin is believed to be mediated largely by a plurality of specialist proteins, RNAs and polypeptide complexes. For example, the roX non-coding RNAs found in flies act with a protein complex to open chromatin and increase transcription on the male X chromosome. Conversely and the mammalian Xist non-coding RNA coats one of the female X chromosomes and causes it to condense into heterochromatin.

At a fundamental level, the most 'open' or euchromatic form of chromatin comprises short sections of the genomic DNA wound around an octet of histone proteins, that together form a nucleosome. The nucleosomes are arrayed in series to form a beads-on-a-string formation. Interactions between adjacent nucleosomes allow the formation of more highly ordered chromatin structures. It is these interactions that can be mediated by enzymes that catalyse post-translational modifications of histones, or structural proteins that physically interact with and assist in anchoring the histones together.

Epigenetic controls over chromatin organisation and stability are essential for the normal and healthy functioning of a cell. Aberrant epigenetic modifications and a decrease in chromatin stability are often seen in senescent, apoptotic or diseased cells, particularly in cancer cells. It is of considerable importance to identify and characterise the multiple proteins and polypeptides that are capable of exhibiting epigenetic activities, as well as those factors that are capable of interacting with chromatin and chromatin associated proteins. It would also be of great value to identify and characterise novel chromatin associated factors, not least to facilitate a better understanding of chromatin biology as a whole.

Conventionally, isolation of proteins associated with chromatin has been achieved by performing a chromatin immunoprecipitation (ChIP). In a typical ChIP assay the chromatin binding proteins are crosslinked to DNA with formaldehyde in vivo. The chromatin is then sheared into small fragments and purified. The purified chromatin fragments are probed with antibodies specific to a known target chromatin binding protein so as to isolate the complex by immunoprecipitation. The precipitated chromatin is treated to reverse the cross-linking, thereby releasing the DNA for sequence analysis. Although it is possible to investigate the ancillary associated proteins pulled down by the cross-linking, the method is not restricted to one genomic region and is not optimised for this. Protocols for performing ChIP are disclosed in Nelson et al. (Nature Protocols (2006) 1:179-185) and Crane-Robinson et al. (Meth. Enzym. (1999) 304:533-547). Furthermore, while ChIP is useful for probing protein regulatory factors across the genome, there are no analogous techniques to determine the binding sites of RNA factors.

A significant drawback with ChIP based techniques is that for a given sequence, at least one specific protein associated with that sequence must be known already. Hence, is a need for a method of isolating protein factors that associate directly or indirectly with a specified target nucleic acid sequence. In effect, there is a need for a method of chromatin associated protein or polypeptide isolation that is nucleic acid sequence driven rather than antigen driven. Also, in ChIP a lack of immunoprecipitation does not necessarily reflect an absence of the tested factor, so there is always a risk of false negative results with this technique.

The present invention overcomes the deficiencies in the art by providing a novel method for isolating factors that associate directly or indirectly with a given target nucleic acid sequence. In particular the method of the invention overcomes the aforementioned problems (1) with regard to isolating novel chromatin binding RNAs and polypeptides and (2) with analyzing the factors associated with a regulatory RNA including its DNA binding sites.

SUMMARY

Aspects of the invention relate to a method for identifying one or more factors associated with a target nucleic acid sequence, wherein the one or more factors comprise at least one ribonucleic acid (RNA) sequence that is associated with the target nucleic acid sequence. The method comprises the steps of obtaining a sample that comprises the target nucleic acid sequence and the one or more factors associated with the target nucleic acid sequence; contacting the sample with one or more capture probes, wherein the capture probes comprise a nucleic acid sequence and at least one affinity label, and wherein the capture probes specifically hybridise with the at least one RNA sequence, under conditions that allow the one or more capture probes to hybridise with the at least one RNA sequence so as to form a hybridization complex between the capture probe, the at least one RNA, the target nucleic acid sequence and the one or more factors associated with the target nucleic acid sequence; isolating the hybridization complex by immobilising the hybridization complex via a molecule that interacts with the affinity label; and analyzing the constituents of the isolated hybridization complex so as to identify the one or more factors associated with the target nucleic acid sequence.

In one embodiment of the methods described herein, the target nucleic acid sequence is comprised within genomic DNA.

In one embodiment of the methods described herein, the target nucleic acid sequence is comprised within chromatin.

In one embodiment of the methods described herein, the target nucleic acid sequence is comprised within a gene.

In one embodiment of the methods described herein, the target nucleic acid sequence is comprised within a regulatory sequence.

In one embodiment of the methods described herein, the regulatory sequence is within a promoter.

In one embodiment of the methods described herein, the regulatory sequence is within a coding region.

In one embodiment of the methods described herein, the regulatory sequence is within a non-coding region.

In one embodiment of the methods described herein, the one or more factors comprise at least one non-coding RNA (ncRNA).

In one embodiment of the methods described herein, the one or more factors comprise at least one messenger RNA (mRNA).

In one embodiment of the methods described herein, the one or more factors comprise at least one polypeptide.

In one embodiment of the methods described herein, the at least one ribonucleic acid (RNA) sequence that is associated with the target nucleic acid sequence is a ncRNA.

In one embodiment of the methods described herein, the at least one ribonucleic acid (RNA) sequence that is associated with the target nucleic acid sequence is an mRNA.

In one embodiment of the methods described herein, the one or more capture probes comprise DNA.

In one embodiment of the methods described herein, the one or more capture probes comprise at least one modified nucleotide analogue.

In one embodiment of the methods described herein, the affinity label is selected from the group consisting of: biotin or an analogue thereof; digoxigenin; fluorescein; dinitrophenol; and an immunotag.

In one embodiment of the methods described herein, the biotin analogue is desthiobiotin.

In one embodiment of the methods described herein, the probe-target hybrid is immobilized through a molecule that binds to the at least one affinity label and which molecule is attached to a solid substrate.

In one embodiment of the methods described herein, the solid substrate comprises a microbead.

In one embodiment of the methods described herein, the microbead is capable of being magnetically separated from a solution.

In one embodiment of the methods described herein, the one or more factors associated with the target nucleic acid sequence are exposed to conditions that result in crosslinking of the one or more factors prior to the step of exposing the sample to the capture probe, and wherein the crosslinking is reversed prior to the step of analyzing the constituents of the isolated hybridization complex so as to identify the one or more factors associated with the target nucleic acid sequence.

In one embodiment of the methods described herein, the conditions that allow the one or more capture probes to hybridise with the at least one RNA sequence comprise high ionic strength and high concentration of a denaturant compound.

In one embodiment of the methods described herein, the denaturant compound is urea.

In one embodiment of the methods described herein, the method comprises an additional pre-treatment step prior to the obtaining step in which the at least one ribonucleic acid (RNA) sequence that is associated with the target nucleic acid sequence is mapped in order to identify regions of the RNA that are accessible to hybridization with a capture probe.

In one embodiment of the methods described herein, the mapping of the RNA sequence comprises exposing the RNA sequence to RNase H in the presence of one or more complementary DNA oligonucleotides, determining the location of any RNase H cleavage sites that result from hybridization of the RNA to the one or more complementary DNA oligonucleotides, and identifying the cleavage sites as regions of the RNA that are accessible to hybridization with a capture probe.

In one embodiment of the methods described herein, mapping of the RNA sequence comprises determining whether the target RNA sequence co-purifies with chromatin when analysed in the form of a sheered chromatin extract.

In one embodiment of the methods described herein, the co-purification is an anti-histone RNA-immunoprecipitation.

In one embodiment of the methods described herein, the co-purification is from a DNA affinity epitope.

In one embodiment of the methods described herein, the sample is from a cell.

In one embodiment of the methods described herein, wherein the cell is a eukaryotic cell.

In one embodiment of the methods described herein, the cell is a mammalian cell.

In one embodiment of the methods described herein, the mammalian cell is a human cell.

In one embodiment of the methods described herein, the sample is obtained from human tissue.

Other aspects of the invention relate to a method for identifying one or more factors associated with a region of chromatin that comprises at least one genomic locus, wherein the one or more factors comprise at least one ribonucleic acid (RNA) sequence that is capable of associating with the at least one genomic locus. The method comprises the steps of obtaining a sample that comprises the region of chromatin and the one or more factors associated with the region of chromatin; contacting the sample with one or more capture probes, wherein the capture probes comprise a nucleic acid sequence and at least one affinity label, wherein the affinity label is conjugated to the one or more capture probes via a spacer group, and wherein the capture probes specifically hybridise with the at least one RNA sequence, under conditions that allow the one or more capture probes to hybridise with the at least one RNA sequence so as to form a hybridization complex between the capture probe, the at least one RNA, the target nucleic acid sequence and the one or more factors associated with the target nucleic acid sequence, wherein the conditions comprise high ionic strength and the presence of high concentration of a denaturant compound; isolating the hybridization complex by immobilising the hybridization complex via a molecule that interacts with the affinity label; and analyzing the constituents of the isolated hybridization complex so as to identify the one or more factors associated with the target nucleic acid sequence.

In one embodiment of the methods described herein, the region of chromatin comprises one or more of the group consisting of: a telomere; a centromere; euchromatin; heterochromatin; a gene; a repeat sequence; a heterologously inserted sequence; and an integrated viral genome.

In one embodiment of the methods described herein, the at least one RNA is a non-coding RNA (ncRNA).

In one embodiment of the methods described herein, the one or more factors comprise at least one polypeptide.

Other aspects of the invention relate to a method for identifying one or more factors associated with a region of chromatin that comprises at least one genomic locus, wherein the one or more factors comprise at least one ribonucleic acid (RNA) sequence that is capable of associating with the at least one genomic locus. The method comprises the steps of obtaining a sample that comprises the region of chromatin and the one or more factors associated with the region of chromatin; contacting the sample with one or more capture probes that specifically hybridise with the at least one RNA sequence, wherein the capture probes comprise a nucleic acid sequence and wherein the capture probes are immobilized on a solid substrate, under conditions that allow the one or more capture probes to hybridise with the at least one RNA sequence so as to form a hybridization complex between the capture probe, the at least one RNA, the target nucleic acid sequence and the one or more factors associated with the target nucleic acid sequence, wherein the conditions comprise high ionic strength and the presence of high concentration of a denaturant compound; and analyzing the constituents of the isolated hybridization complex so as to identify the one or more factors associated with the target nucleic acid sequence.

In one embodiment of the methods described herein, the solid substrate comprises a microbead.

Another aspect of the invention relates to a method for identifying one or more factors associated with a region of chromatin that comprises at least one genomic locus, wherein the one or more factors comprise at least one non-coding ribonucleic acid (ncRNA) sequence that is capable of associating with the at least one genomic locus. The method comprises the steps of mapping the at least one ncRNA sequence in order to identify regions of the ncRNA that are accessible to hybridization; synthesizing one or more capture probes, wherein the capture probes comprise a nucleic acid sequence and at least one affinity label, wherein the affinity label is conjugated to the one or more capture probes via a spacer group, and wherein the capture probes are able to hybridize with the at least one ncRNA sequence in a region defined as accessible to hybridization by the mapping step; obtaining a sample that comprises the region of chromatin and the one or more factors associated with the region of chromatin; contacting the sample with one or more capture probes, under conditions that allow the one or more capture probes to hybridise with the at least one ncRNA sequence so as to form a hybridization complex between the capture probe, the at least one ncRNA, the target nucleic acid sequence and the one or more factors associated with the target nucleic acid sequence, wherein the conditions comprise high ionic strength and the presence of high concentration of a denaturant; isolating the hybridization complex by immobilising the hybridization complex via a molecule that interacts with the affinity label; and analyzing the constituents of the isolated hybridization complex so as to identify the one or more factors associated with the target nucleic acid sequence.

In one embodiment of the methods described herein, the mapping step comprises exposing the ncRNA sequence to RNase H in the presence of one or more complementary DNA oligonucleotides, determining the location of any RNase H cleavage sites that result from hybridization of the ncRNA to the one or more complementary DNA oligonucleotides, and identifying the cleavage sites as regions of the ncRNA that are accessible to hybridization.

Another aspect of the invention relates to an assay for identifying one or more factors associated with a target nucleic acid sequence, wherein the one or more factors comprise at least one RNA sequence that is associated with the target nucleic acid sequence. The assay comprises (i) one or more capture probes, wherein the capture probes comprise a nucleic acid sequence and at least one affinity label, and wherein the nucleic acid sequence of the capture probes is complementary to and will specifically hybridize with at least a part of the at least one RNA sequence; (ii) a hybridization buffer solution for providing conditions that allow the one or more capture probes to hybridise with the at least one RNA sequence so as to form a hybridization complex between the capture probe, the at least one RNA, the target nucleic acid sequence and the one or more factors associated with the target nucleic acid sequence, wherein the conditions comprise high ionic strength and the presence of high concentration of a denaturant; and (iii) a label comprising set of instructions on how to perform the assay.

In one embodiment of the assays described herein, the affinity label is conjugated to the one or more capture probes via a spacer group.

In one embodiment of the assays described herein, the assay further comprises (iv) a solid substrate that comprises a molecule that is capable of binding to the at least one affinity label and which molecule is attached to the solid substrate.

In one embodiment of the assays described herein, the solid substrate comprises a microbead.

In one embodiment of the assays described herein, the microbead comprises magnetic particles so that it is capable of being magnetically separated from a solution.

In one embodiment of the assays described herein, the assay further comprises a solution of RNase H.

Another aspect of the invention relates to an assay for identifying one or more factors associated with a target nucleic acid sequence, wherein the one or more factors comprise at least one RNA sequence that is associated with the target nucleic acid sequence. The assay comprises (i) one or more capture probes, wherein the capture probes comprise a nucleic acid sequence and wherein the capture probes are immobilized on a solid substrate, and wherein the nucleic acid sequence of the capture probes is complementary to and will specifically hybridize with at least a part of the at least one RNA sequence; (ii) a hybridization buffer solution for providing conditions that allow the one or more capture probes to hybridise with the at least one RNA sequence so as to form a hybridization complex between the capture probe, the at least one RNA, the target nucleic acid sequence and the one or more factors associated with the target nucleic acid sequence, wherein the conditions comprise high ionic strength and the presence of high concentration of a denaturant; and (iii) a label comprising set of instructions on how to perform the assay.

In one embodiment of the assays described herein, the solid substrate comprises a microbead.

In one embodiment of the assays described herein, the microbead comprises magnetic particles so that it is capable of being magnetically separated from a solution.

In one embodiment of the assays described herein, the assay further comprises a solution of RNase H.

Other aspects of the invention relate to a method for identifying one or more genomic DNA target nucleic acids of a non-coding RNA sequence (ncRNA), comprising a) treating a chromatin extract comprising the ncRNA, to thereby reversibly cross-link the ncRNA present in the extract to an associated genomic DNA target nucleic acid(s) present in the extract; b) contacting the extract from step a) with one or more capture probes specific to the ncRNA under conditions that allow the capture probes to specifically hybridize with the ncRNA to thereby form a hybridization complex comprised of the capture probe(s), the ncRNA and the associated genomic DNA target nucleic acid(s); c) isolating the hybridization complex by immobilizing the one or more capture probes in the context of the hybridization complex; and d) analyzing DNA in the hybridization complex to thereby identify the genomic DNA target nucleic acid(s).

In one embodiment, analyzing the hybridization complex comprises a) treating the hybridization complex to uncross-link the ncRNA and associated genomic DNA target nucleic acid(s); and b) sequencing the genomic DNA target nucleic(s) acid present in the hybridization complex.

In one embodiment, the method further comprises amplifying the genomic DNA target nucleic acid present in the hybridization complex prior to sequencing.

Other aspects of the invention relate to a method for identifying one or more factors associated with a non-coding RNA sequence (ncRNA), comprising, a) treating a genomic DNA extract comprising the ncRNA, to thereby reversibly cross-link the ncRNA present in the extract to one or more associated genomic DNA target nucleic acids present in the extract, b) contacting the extract from step a) with one or more capture probes specific to the ncRNA under conditions that allow the capture probes to specifically hybridize with the ncRNA to thereby form a hybridization complex comprised of the capture probe(s), the ncRNA and the associated genomic DNA target nucleic acid(s); c) isolating the hybridization complex by immobilizing the one or more capture probes in the context of the hybridization complex; and d) analyzing the hybridization complex for the presence of associated proteins or RNAs, to thereby identify factors associated with the ncRNA.

In one embodiment, the analyzing step d) comprises performing western blot analysis of proteins present in the hybridization complex to thereby analyze the hybridization complex for the presence of associated proteins.

In one embodiment, analyzing step d) comprises performing PCR on RNA present in the hybridization complex to thereby analyze the hybridization complex for the presence of RNAs.

In one embodiment, analyzing step d) further comprises performing sequencing of the RNA present in the hybridization complex.

In one embodiment, the capture probes are DNA oligonucleotides.

In one embodiment, capture probes comprise an affinity label and the hybridization complex is immobilized by binding of the affinity label to a specific binding partner.

In one embodiment, the affinity label is biotin.

Other aspects of the invention relate to a method for determining one or more oligonucleotide sequences for use in a capture probe for a specific ncRNA, for use in Capture Hybridization Analysis of RNA Targets (CHART), comprising: a) preparing a reversibly cross-linked chromatin extract; b) providing candidate oligonucleotides; c) separately combining each of the candidate oligonucleotides of step b) to the reversibly cross-linked chromatin extract, the presence of RNase H, under conditions suitable for RNA hydrolysis of RNA-DNA hybrids, to thereby produce a chromatin-oligonucleotide mixture; d) performing RT-qPCR on the chromatin-oligonucleotide mixture to detect RNAse H sensitivity; and e) identifying a candidate oligonucleotide as a sequence for use as a capture probe for CHART when RNAse H sensitivity in step d) is detected.

In one embodiment, the reversibly cross-linked chromatin extract of step a) is prepared by formaldehyde cross-linking.

In one embodiment, the candidate oligonucleotides are between 15 and 25 nucleotides in length.

In one embodiment, the candidate oligonucleotides are 20 nucleotides in length

In one embodiment, the RT-qPCR is performed with a primer set that amplifies a region of the target cDNA that includes the oligo probe, a control primer set for an unrelated RNA, and a control primer set designed to hybridize to a region representative of the ncRNA that is not RNAse H sensitive.

Other aspects of the invention relate to a kit comprising one or more capture probes optimized for use in Capture Hybridization Analysis of RNA Targets (CHART) for a specific ncRNA.

In one embodiment, the capture probes are optimized for a specific stage of development within a cell.

In one embodiment, the capture probes are optimized for a specific cell type.

BRIEF DESCRIPTION OF THE DRAWINGS

FIG. 11A shows enrichment of RNAs by roX2 CHART (using C-oligos listed in Table 3) as measured by RT-qPCR. FIG. 11B shows enrichment of DNA loci by roX2 CHART. CES-5C2 is a regulatory site enriched by roX2 CHART. The enrichment values are labeled for comparison of CES-5C2 by roX2 CHART with sense-oligo CHART and also with roX2 CHART at a control site, Pka. RNase-positive lanes represent CHART enrichment from extracts pretreated with RNase to eliminate RNA-mediated signal. Error bars represent ±SEM for three qPCR experiments. Primers are listed in Table 4. FIG. 11C shows specific enrichment of a tagged MSL subunit, MSL3-TAP, by roX2 CHART. DSP1 antisera (64) is used as a negative control because of its sensitivity.

FIG. 12B shows results similar to FIG. 12A, but enrichment of associated DNA loci as determined by qPCR. Error bars represent ±SEM for three independent CHART experiments. FIG. 12C shows specific enrichment of two paraspeckle proteins, p54/nrb and PSPC1, by NEAT1 CHART from MCF7 extract. Histone H3 was chosen as a negative control because it is a highly sensitive antiserum and NEAT1 is not expected to be predominantly chromatin bound.

FIG. 13A, top four rows, mapped sequencing reads from roX2 and sense-oligo CHART data (performed from S2 cells expressing MSL3-TAP) (55) compared to MSL3-TAP ChIP data from MSL3-TAP Clone 8 (41). Both mapped read numbers and normalized read numbers are listed. Note the RNase-H-eluted roX2 CHART has higher peaks signals at roX2 binding sites and required a different scale than the other three sequencing tracks. Below, ChIP-chip data for the indicated histone modifications are shown (S2 cells, Mod-ENCODE) (65). FIG. 13B shows finer-scale examples and comparisons of roX2 CHART data, with normalized read depth, except Far Right where normalized for peak height. FIG. 13C shows a correlation between the roX2 CHART signal and MSL3-TAP ChIP signal (41) by plotting the conservative enrichment magnitudes (relative to corresponding inputs) on a log 2 scale of roX2 CHART peaks (from combined RNase-H-elution replicates) and MSL3-TAP ChIP peaks. Peaks from chrX are shown in red and autosomal peaks in blue, but the Pearson r was determined including both sets of peaks.

FIG. 13D shows a motif identified from the top roX2 CHART peaks, depicted here as a motif logo in comparison with a nearly identical motif previously determined from MSL3-TAP ChIP-chip data (41).

FIG. 14 A FIG. 14B Top, the 5' region of roX2 RNA examined using RNase-H mapping. Three primer sets (indicated here in green, blue, and red) were used to assay cleavage by RT-qPCR. Below, each point on this plot depicts the RNase-H sensitivity induced by a single oligonucleotide, and cleavage measured using the primer sets shown. RNase-H sensitivity represents the ratio of cleaved to uncleaved RNA (e.g., a value of 9 corresponds to 90% cleavage). Note that the sites of high sensitivity are only observed with the appropriate primer sets. The targets of the C-oligos based on this mapping are indicated with gray arrowheads. FIG. 14D shows the design of C-oligos used inbiotin-eluted CHART and FIG. 14E shows the design of C-oligos used for RNase-H-eluted CHART.

FIG. 16A shows the location of oligonucleotides. Using HeLa cell extract, peaks of RNase-H sensitivity were used to design C-oligos to a mammalian lncRNA. Similar to analysis depicted in FIG. 10B, RNase-H mapping of a region of NEAT1 (980-1240 nt of NR_028272.1) and MALAT1 revealed sites of high RNase-H sensitivity that were used to design C-oligos (sites indicated by gray arrowheads). FIG. 16B shows NEAT1 CHART, but not MALAT1 CHART, enriches NEAT1 RNA in MCF7 cells, similar to analysis depicted in FIG. 12A demonstrating enrichment of specific RNAs by RT-qPCR with different CHART experiments (0, Mock; N, NEAT1; M, MALAT1) and RNase refers to pretreatment of the extract with RNase prior to CHART analysis. FIG. 16C shows NEAT1 CHART, but not MALAT1 CHART, enriches the NEAT1 endogenous locus in MCF7 cells, similar to analysis depicted in FIG. 12B demonstrating enrichment of specific DNA loci by qPCR with different CHART experiments as in FIG. 16B.

FIG. 17A shows that whereas the top roX2 CHART peaks are found on chrX, some of the lower-significance peaks from biotin-eluted roX2 CHART-seq correspond to sites that are caused by direct binding of the C-oligos to DNA. Comparison of normalized sequencing reads across a region of chr2L demonstrating several roX2 CHART peaks (marked by asterisks) that correspond to peaks also observed in the sense control, suggesting they are caused by direct binding of the C-oligos to DNA and are not roX2 binding sites. Supporting this conclusion, these peaks were greatly reduced in an RNase-H-eluted roX2 CHART and did not correspond to peaks in the MSL3-TAP ChIP experiment (Alekseyenko A A, et al. (2008) Cell 134:599-609). FIG. 17B shows peaks from biotin-eluted roX2 CHART data were ordered by the enrichment magnitude relative to the senseoligo control and plotted for their cumulative fraction found on the chrX. The red dashed line shows the cutoff at 173 peaks where 100% of peaks are found on chrX. FIG. 17C shows the analysis of DNA enrichment by RNase-H-eluted roX2 CHART based on qPCR and similar to FIG. 11B. Results are plotted on a log 10 scale. Error bars are ±SEM from three qPCR replicates. A genome-wide correlation of biotin-eluted and RNase-H-eluted CHARTread density (200-bp bandwidth) was deduced and plotted on a log 10 scale (not shown). chrX peaks were plotted along side with autosomal peaks and analyzed. A correlation for all data was also deduced. The correlation between two RNase-H-eluted CHARTreplicates were similarly deduced. FIG. 17D similar to FIG. 17B, peaks from RNase-H-eluted roX2 CHART data were ordered by the enrichment magnitude relative to the input and plotted for their cumulative fraction found on the chrX. The red dashed line shows the cutoff at 214 peaks where 100% of peaks are found on chrX.

FIG. 18 shows data from experiments.

FIG. 19A-FIG. 19D is a schematic and collection of bar graphs and photographs of data generated from the application of CHART to the Xist RNA in mammalian cells. FIG. 19 A is a schematic overview of the CHART procedures as applied in Example 3. FIG. 19B shows a bar graph of data from experiments showing RNA enrichment. FIG. 19C shows a bar graph of data from experiments showing DNA enrichment.

DETAILED DESCRIPTION

Figure 1:
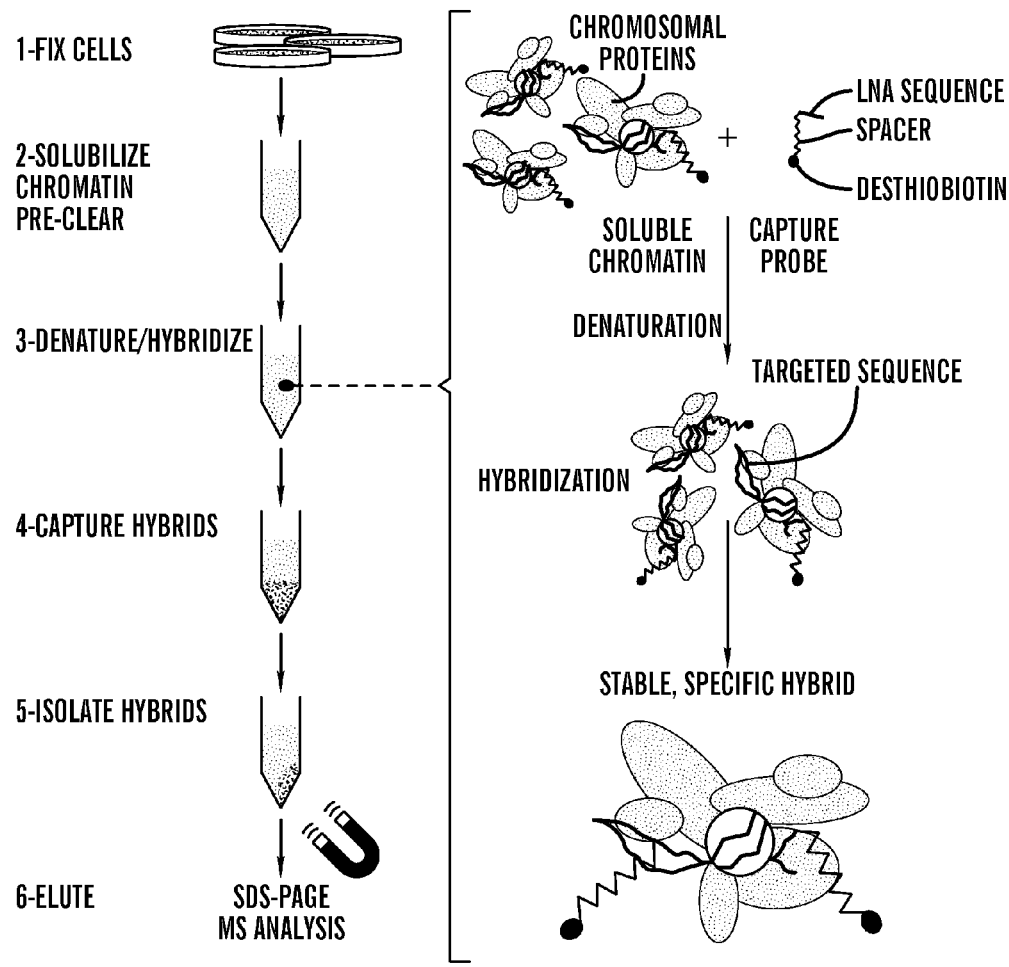
FIG. 1 shows a graphical representation of the PICh (Proteomics of Intact Chromatin) procedure.

All references cited herein are incorporated by reference in their entirety. Unless otherwise defined, all technical and scientific terms used herein have the same meaning as commonly understood by one of ordinary skill in the art to which this invention belongs. It will be understood that the present invention involves use of a range of conventional molecular biology techniques, which can be found in standard texts such as Sambrook et al. (Sambrook et al (2001) Molecular Cloning: A Laboratory Manual; CSHL Press, USA).

In setting forth the detailed description of the invention, a number of definitions are provided that will assist in the understanding of the invention.

The term "polypeptide" as used herein, refers to a polymer of amino acid residues joined by peptide bonds, whether produced naturally or in vitro by synthetic means. Polypeptides of less than approximately 12 amino acid residues in length are typically referred to as a "peptide". The term "polypeptide" as used herein denotes the product of a naturally occurring polypeptide, precursor form or proprotein. Polypeptides also undergo maturation or post-translational modification processes that may include, but are not limited to: glycosylation, proteolytic cleavage, lipidization, signal peptide cleavage, propeptide cleavage, phosphorylation, ubiquitylation, sumoylation, acetylation, methylation and such like. A "protein" is a macromolecule comprising one or more polypeptide chains.

A "polypeptide complex" as used herein, is intended to describe proteins and polypeptides that assemble together to form a unitary association of factors. The members of a polypeptide complex may interact with each other via non-covalent or covalent bonds. Typically members of a polypeptide complex will cooperate to enable binding either to DNA or to polypeptides and proteins already associated with or bound to DNA (i.e. chromatin). Chromatin associated polypeptide complexes may comprise a plurality of proteins and/or polypeptides which each serve to interact with other polypeptides that may be permanently associated with the complex or which may associate transiently, dependent upon cellular conditions and position within the cell cycle. Hence, particular polypeptide complexes may vary in their constituent members at different stages of development, in response to varying physiological conditions or as a factor of the cell cycle. By way of example, in animals, polypeptide complexes with known chromatin remodelling activities include Polycomb group gene silencing complexes as well as Trithorax group gene activating complexes.

The term "isolated", when applied to a nucleic acid or polypeptide sequence is a sequence that has been removed from its natural organism of origin. Typically, an isolated polypeptide or polynucleotide/nucleic acid molecule has been removed from the environment in which it was produced; although, it is not necessarily in a pure form. That is, an isolated polypeptide or polynucleotide is not necessarily 100% pure, but may be about 10%, 20%, 30%, 40%, 50%, 60%, 70%, 80% or 90% pure. A purified, isolated polypeptide or polynucleotide is advantageously at least 80% pure, and may be at least 90%, at least 95% or at least 98% pure (e.g. 99% pure). In the present context, the term "isolated" when applied to a polypeptide is intended to include the same polypeptide in alternative physical forms whether it is in the native form, denatured form, dimeric/multimeric, glycosylated, crystallised, or in derivatised forms. Advantageously, the nucleic acid molecules/polynucleotides/oligonucleotides (e.g. nucleic acid probes, RNAi molecules etc.), and polypeptides/peptides (e.g. antibodies or fragments thereof) of the invention are isolated; and more beneficially, purified.

Chromatin is the compacted structure of genomic DNA present in the nucleus of most eukaryotic cells. It comprises DNA and a plurality of DNA-binding proteins as well as certain RNAs. The term 'chromatin' derives from the readiness of this cellular material to hold stain with certain chemical dyes (chromaticity). Chromatin is primarily comprised of DNA associated with histone proteins that together form a basic nucleosomal structure. The nucleosome comprises an octet of histone proteins around which is wound a stretch of double stranded DNA 146 by in length. H1stones H2A, H2B, H3 and H4 are part of the nucleosome while histone H1 can act to link adjacent nucleosomes together into a higher order structure. Assembly into higher order structures allows for greater packing, or condensation of the DNA. Chromatin is often referred to as occurring in two main states, euchromatin and heterochromatin, corresponding to uncondensed actively transcribed DNA and condensed DNA respectively. Many further polypeptides, RNAs and protein complexes interact with the nucleosome and the histones in order to mediate transition between the euchromatic and heterochromatic states. The identity and functional activity of many of these crucially important chromatin associated proteins and complexes is presently unknown.

A "target nucleic acid" as the term is used herein, refers to a nucleic acid to which another nucleic acid binds in the context of the cellular environment. Typically such binding is through complementarity of the respective nucleic acid sequences.

An affinity label, as the term us used herein, refers to a moiety that specifically binds another moiety and can be used to isolate or purify the affinity label, and compositions to which it is bound, from a complex mixture. One example of such an affinity label is a member of a specific binding pair (e.g, biotin:avidin, antibody:antigen). The use of affinity labels such as digoxigenin, dinitrophenol or fluorescein, as well as antigenic peptide 'tags' such as polyhistidine, FLAG, HA and Myc tags, is envisioned.

Epigenetics concerns the transmission of information from a cell or multicellular organism to its descendants without that information being encoded in the nucleotide sequence of genes. Epigenetic controls are typically established via chemical modification of the DNA or chromatin structure. Gene expression can be moderated, in some cases, via the covalent attachment of chemical groups to polypeptides that are associated with or that can bind to DNA. By way of example, methylation, sumoylation, phosphorylation, ubiquitylation and/or acetylation of histones can lead to activation or silencing of gene expression in the region of the genome where these epigenetic modifications have occurred. Epigenetic modifications can occur at different times in the normal development of an organism, and also during transformation of normal cells into cancerous cells. Such modifications often result in the silencing or activation of certain genes. In cancer, it is well documented that the majority of tumour cells display abnormal DNA epigenetic imprints (Feinberg A P & Vogelstein B, (1983) Nature 1(5895):89-92).

The term "cancer" is used herein to denote a tissue or a cell located within a neoplasm or with properties associated with a neoplasm. Neoplasms typically possess characteristics that differentiate them from normal tissue and normal cells. Among such characteristics are included, but not limited to: a degree of anaplasia, changes in cell morphology, irregularity of shape, reduced cell adhesiveness, the ability to metastasise, increased levels of angiogenesis, increased cell invasiveness, reduced levels of cellular apoptosis and generally increased cell malignancy. Terms pertaining to and often synonymous with "cancer" include sarcoma, carcinoma, tumour, epithelioma, leukaemia, lymphoma, polyp, transformation, neoplasm and the like.

An embodiment of the present invention resides in the development of a method for identifying proteins, polypeptides, RNA and protein complexes that are associated with a particular target chromatin site, gene or stretch of nucleic acid, such as DNA. The method utilises a high specificity nucleic acid probe optionally labelled with an affinity tag that allows for isolation of probe-target hybridised sequences. To determine whether a protein of interest is localized to a specific genomic region, the standard approach has been to combine immuno-staining and DNA fluorescent in situ hybridization (immuno-FISH) on fixed nuclei. However, previous attempts to retrieve target chromatin using conventional DNA capture/FISH probes and standard FISH reagents have always suffered from very low yields and high contamination from non-specific proteins. The method of the invention demonstrates an advantage of enabling the identification of any and all DNA and/or chromatin associated proteins at a specified target site without the need for prior knowledge of any of the proteins that may or may not be present at that site. Hence, the method of the invention also demonstrates considerable advantage over immuno-precipitation based techniques, such as ChIP, which rely on the presence of a known protein antibody target that is already bound to the DNA. Also, if the antibody is quantitatively precipitating a crosslinked antigen, which is rare, ChIP does not permit purification of a single loci but a mixture of loci that contain the protein of interest. The method of the invention also allows for changes in chromatin/DNA associated protein complexes to be monitored under different cellular conditions as well.

As shown in FIG. 1, the PICh (proteomics of intact chromatin) process allows for targeting of specific sequences in genomic DNA and thereby isolating any associated chromatin factors (described in co-pending patent application U.S. Ser. No. 12/674,163; and published as Déjardin and Kingston. Purification of proteins associated with specific genomic Loci. Cell (2009) vol. 136 (1) pp. 175-86, the contents of each of which are herein incorporated by reference in their entirety). In brief, cells are fixed, the chromatin solubilized, a specific probe is hybridized to the chromatin, the hybridized chromatin is then captured on magnetic beads, the hybrids are eluted and the proteins identified. Extensive crosslinking with agents such as formaldehyde can be used to preserve protein-DNA and protein-protein interactions. Unlike strategies based upon antibody antigen affinity, nucleic acid hybridization is insensitive to the presence of ionic detergents, which allows the use of these detergents throughout to limit contamination. To increase the stability of the probe-chromatin interactions, Locked Nucleic Acid (LNA) containing oligonucleotides were used as probes because LNA residues have an altered backbone that favours base stacking thereby significantly increasing their melting temperature (Vester, B., and Wengel, J. (2004) Biochemistry 43, 13233-13241). To minimize the steric hindrance (which is detrimental for yields) observed upon immobilization of chromatin an extremely very long spacer group was used between the immobilization tag and the LNA probe. Suitable spacers include long chain aliphatic groups, or spacers can be synthesised from methoxyoxalamido and succinimido precursors such as those described in Morocho, A. M. et al (Methods Mol Biol (2005) 288, 225-240). Finally the co-elution of non-specific factors was limited by using desthiobiotin, a biotin analog with weaker affinity for avidin, permitting a competitive gentle elution using biotin. The PICh process uses a genomic sequence driven approach to isolation of associated factors. As a result, PICh requires a highly specific probe design that can penetrate the complex structure of chromatin.

The regulation of genetic information in a eukaryotic cell occurs in the context of chromatin, and the importance of protein factors that regulate chromatin has long been appreciated. More recently, however, it has become clear that non-coding RNAs (ncRNAs), especially long ncRNAs (>100 nt) also play important roles regulating chromatin, but the range of RNAs involved, their functions and the specific genomic loci that are regulated by ncRNAs is largely unknown. Part of the reason present understanding of RNAs has lagged behind the knowledge of proteins is that routine experiments with proteins, such as co-immunoprecipitation (coIP), RNA immunoprecipitation (RIP) and chromatin immunoprecipitation (ChIP), do not have well-established analogous procedures for RNAs. Therefore, a broadly applicable affinity purification technique that allows the identification of factors that interact with the endogenous RNA (analogous to coIP) and the determination of the genomic localization (analogous to ChIP) or interacting RNAs (RIP) would provide important insight into the regulation of chromatin.

Genomic analyses have demonstrated that although less than 2% of the mammalian genome encodes proteins, at least two thirds is transcribed. It is widely accepted that ncRNAs (non-coding RNAs), as opposed to protein-coding RNAs (mRNAs), represent the majority of human transcripts; and the regulatory roles of many of these ncRNAs have been elucidated in recent years. Many non-translated RNAs have now been characterized, and several long transcripts, ranging from 0.5 to over 100 kb, have been shown to regulate gene expression by modifying chromatin structure. Functions uncovered at a few well characterized loci demonstrate a wide diversity of mechanisms by which ncRNAs can regulate chromatin over a single promoter, a gene cluster, or an entire chromosome, in order to activate or silence genes in cis or in trans. One important role so far recognized for ncRNAs is their participation in the epigenetic regulation of genes. Indeed, it is becoming increasingly apparent that many epigenetic mechanisms of gene expression are controlled by ncRNAs.

The present technique is referred to as CHART (Capture Hybridization Analysis of RNA Targets), a hybridization-based strategy to map genome-wide binding sites for endogenous RNAs (including ncRNAs). CHART involves identifying complementary oligonucleotides to the RNA that are then used to purify these RNAs from crosslinked extracts. The enrichment has proven sufficient to demonstrate co-purification of associated proteins and other polypeptide and RNA factors. Furthermore, CHART allows the identification of the genomic loci where RNAs are bound to chromatin. This technique is generally applicable; CHART is capable of enriching different RNAs from different organisms. Therefore the present inventors believe this protocol will provide the technology required to raise the understanding of ncRNA to the same level as that for the protein factors that regulate chromatin.

Following performance of CHART, the CHART enriched material (typically isolated in the form of a hybridization complex, can be analysed to identify its components. Such components may include, without limitation, specific target nucleic acids (e.g., genomic DNA), proteins, and RNAs.

Figure 2A:
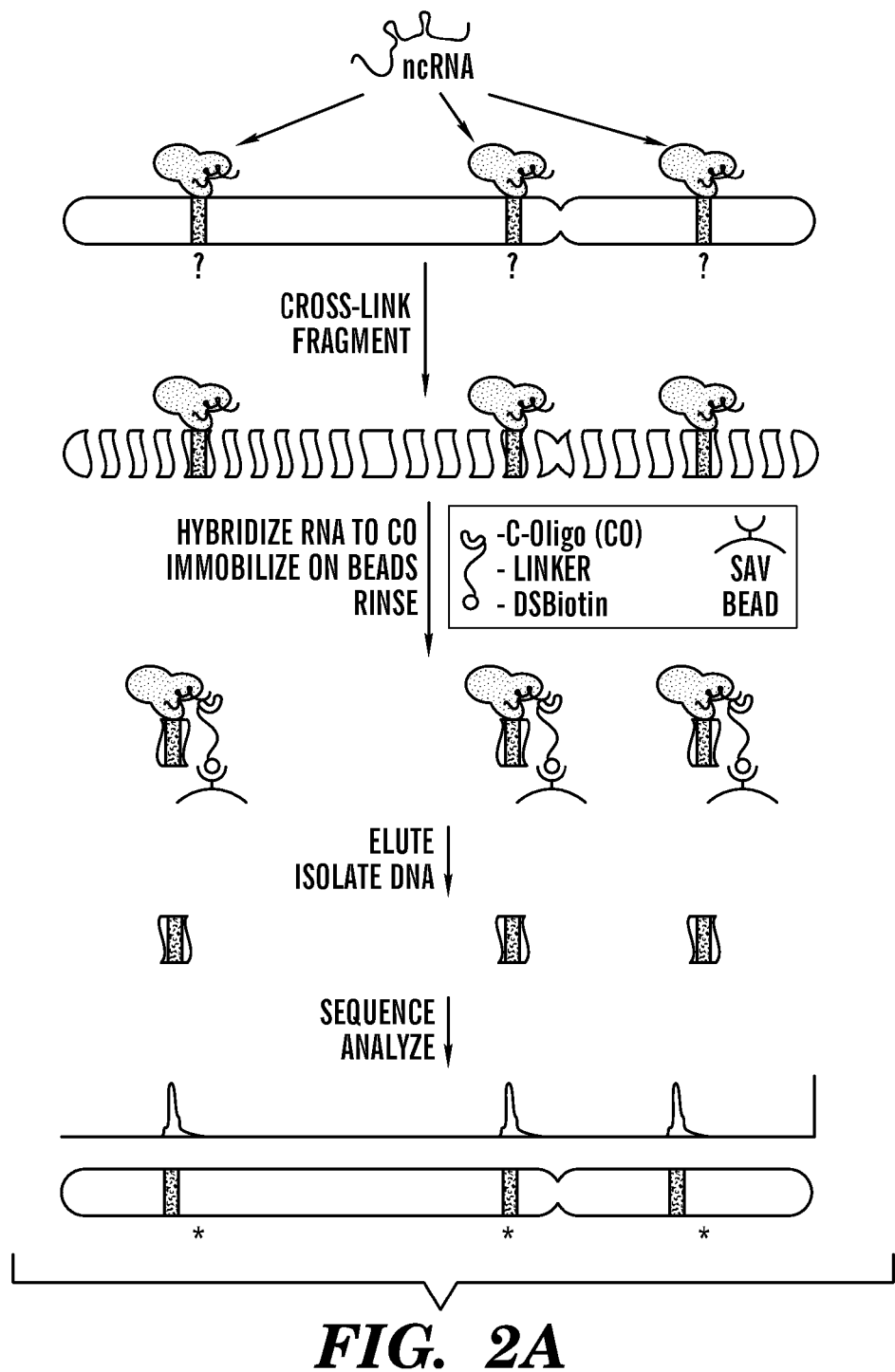
FIG. 2 shows (A) a schematic overview of the CHART procedure of one embodiment of the invention; (B-C) the regions of normalized, mapped sequencing reads from roX2 and control CHART data (S2 cells) compared with MSL3-TAP ChIP (MSL3-TAP Clone 8 cells); (D) a graph showing distribution of sequencing reads for CESs compared to non-CESs.
Figure 2B:
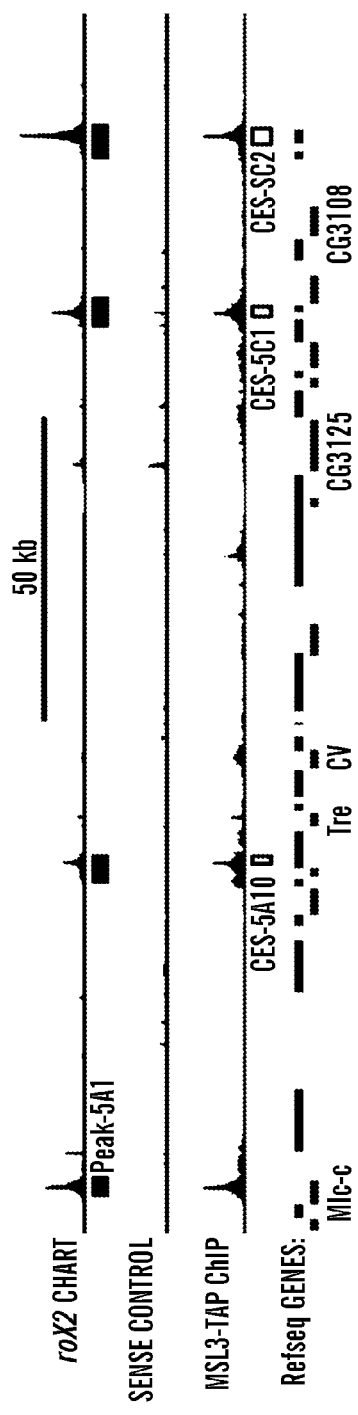
Figure 2C:
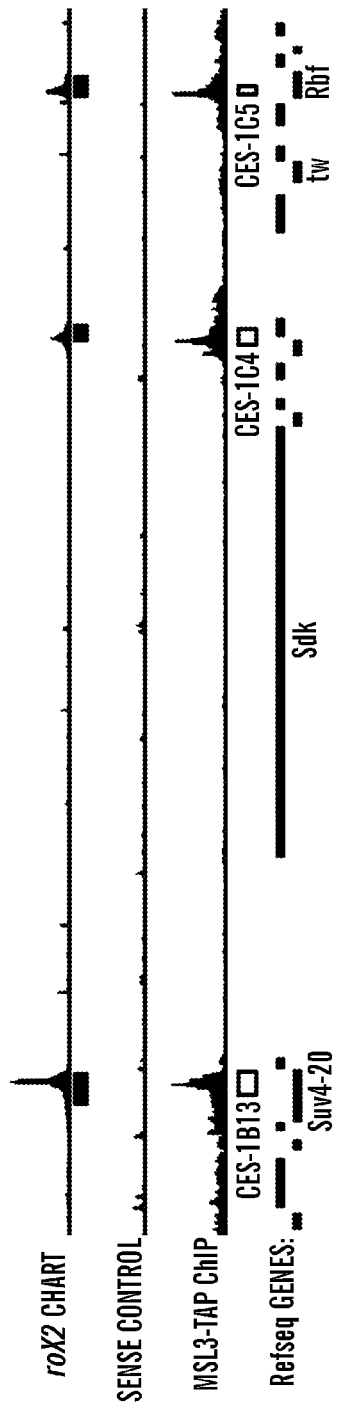
Figure 2D:
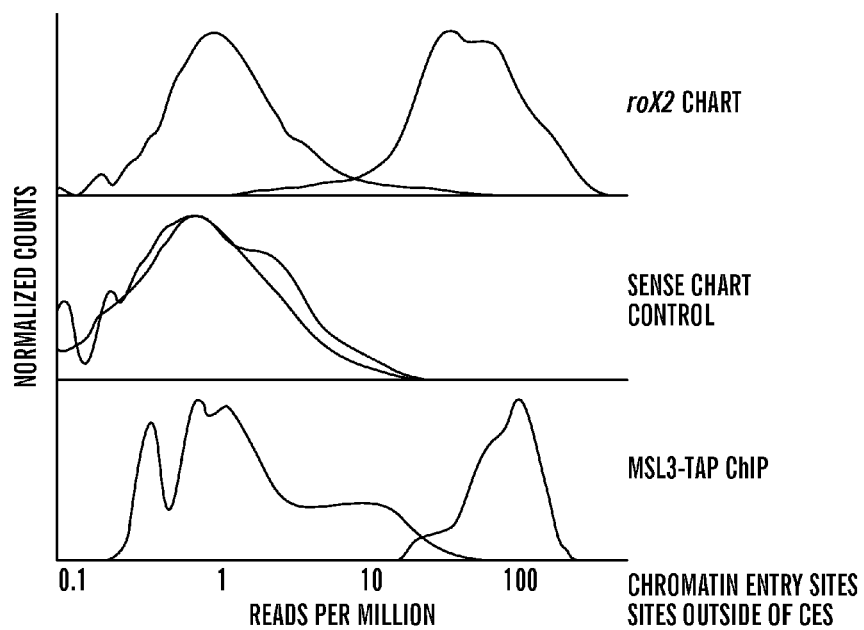

In one embodiment of the invention the CHART method is set out in FIG. 2A and comprises the following general process:
  (a) obtaining a sample that comprises the target nucleic acid sequence and one or more polypeptide, protein or RNA (including ncRNA) factors associated with the target nucleic acid sequence;
  (b) contacting the sample with one or more capture probes, wherein the capture probes comprise a nucleic acid sequence and at least one affinity label, and wherein the capture probes specifically hybridise with at least one RNA factor that is associated with the target nucleic acid sequence;
  (c) providing conditions that allow the one or more capture probes to hybridise with an exposed region of the at least one RNA factor so as to form a hybridization complex between the capture probe, the at least one RNA, the target nucleic acid sequence and the one or more other factors associated with the target nucleic acid sequence;

(d) isolating the hybridization complex by immobilising the hybridization complex via a molecule that interacts with the affinity label; and (e) analyzing the constituents of the isolated hybridization complex so as to identify the one or more factors associated with the target nucleic acid sequence.

Association of the polypeptide, protein or RNA factors with the target nucleic acid sequence can be covalent (e.g., as achieved by crosslinking, as described herein). Contacting step b) can be under the conditions of step c) (e.g., performed concurrently with step c). Conditions of step c) can be achieved using the appropriate aqueous buffer components and conditions. In one embodiment, no SDS is added or used in the aqueous assay. In one embodiment, the conditions comprise high ionic strength. In one embodiment, the conditions comprise high concentrations of denaturant.

In one embodiment, high salt concentration is achieved using one or more of sodium chloride, sodium acetate, tetra-alkylammonium salts, lithium chloride, ammonium acetate, and cesium chloride. In one embodiment, the salt concentration is greater than or equal to about 100 mM. In one embodiment, the salt concentration is in the range of about 100 mM to no more than about 1.5 M. In one embodiment, the salt concentration is greater than or equal to about 250 mM. In one embodiment, the salt concentration is no greater than about 1M. In one embodiment, the salt concentration is in the range of about 250 mM to no more than about 1M. In one embodiment, the salt concentration is about 800 mM.

In one embodiment, high denaturant concentration is achieved using one or more of urea, formamide, dimethylsuofoxide, guanidine hydrochloride, and dimethylformamide. In one embodiment, the denaturant is present at a final reaction concentration of no less than around 0.5 M. In one embodiment, the final concentration is less than or equal to about 5M. In one embodiment, the final concentration falls within the range of from about 0.5 M to about 5M. In one embodiment, the final concentration is greater than or equal to about 1M. In one embodiment, the final concentration is less than or equal to about 3 M. In one embodiment, the final concentration falls within the range of about 1M to about 3M. In one embodiment, the final concentration is about 2M.

All possible combinations of salt concentrations and denaturant concentrations described herein are envisioned.

The above stated parameters of the general process may also be applied to similar such processes described herein.

An alternative embodiment of the invention provides for capture probes that are already immobilized on a solid substrate. In this embodiment, the CHART procedure is summarised as follows:

(i) obtaining a sample that comprises the target nucleic acid sequence and one or more polypeptide, protein or RNA (including ncRNA) factors associated with the target nucleic acid sequence;

(ii) contacting the sample with one or more capture probes, wherein the capture probes comprise a nucleic acid sequence and are immobilized on a solid support, and wherein the capture probes specifically hybridise with at least one RNA factor that is associated with the target nucleic acid sequence;

(iii) providing conditions that allow the one or more capture probes to hybridise with an exposed region of the at least one RNA factor so as to form a hybridization complex between the immobilized capture probe, the at least one RNA, the target nucleic acid sequence and the one or more other factors associated with the target nucleic acid sequence; and (iv) analyzing the constituents of the isolated hybridization complex so as to identify the one or more factors associated with the target nucleic acid sequence.

The capture probes may be designed by a number of methods, one of which involves RNase H mapping of a specified ncRNA and is described in more detail below. However, it will be understood by the skilled artisan that alternative methods for designing hybridization capture probes may be based on known chemical mapping techniques or bioinformatics analysis of known or projected secondary structure of a specified RNA sequence. However, it should be noted that the CHART process is not limited to use of highly specific PICh probes because, unlike PICh, the CHART capture probes are directed towards hybridization with exposed nucleic acid sequences and not with the genomic DNA.

The capture probes utilised in CHART may be characterised by the presence of one or more affinity labels that are spaced apart from the probe oligonucleotide sequence by an intervening group—termed a spacer group. The spacers may be suitably equivalent to those extra-long groups used in PICh probes and described in detail in U.S. patent application Ser. No. 12/674,163, incorporated herein by reference. In one embodiment of the invention, spacers of at least 20 atoms in length, typically around 30 atoms in length, are suitably used.

As mentioned, the capture probe may also be immobilized prior to the hybridisation step. Immobilization of the capture probe can be achieved via covalent chemical linkage or affinity interaction (e.g. avidin-biotin interaction), by an affinity label present in the capture probe, as conventionally known in the art. The immobilized capture probe may be bound/linked to a variety of suitable substrates including beads, such as microbeads (e.g. polystyrene or other polymer beads, including magnetic microbeads) or to a solid surface (e.g. including a polymer or glass surface).

Analysis of the constituents of the hybridization complex may occur by one or more of the techniques described previously with regards to PICh. In addition, since the hybridization complex may comprise hybridized DNA-RNA, it is also possible to elute components of the complex for more detailed analysis by way of enzymatic treatment with RNase H.

Accordingly, the present invention further resides in the provision of a subset of polypeptides and nucleic acids that are newly identified as possessing chromatin association activity, and thus which potentially act as novel epigenetic factors. The invention facilitates the identification of further epigenetic factors and, importantly, the identification of novel epigenetic activity in known polypeptides.

In a specific embodiment, the present invention provides a method by which polypeptides and components of protein complexes associated with chromatin at specified sites in the genome can be characterised. It should be noted that the method of the invention is not limited to those polypeptides that are solely DNA binding, but includes associated polypeptides such as those with histone binding activity, for example.

In accordance with specific embodiments of the invention, the capture probe may be labelled with one or more suitable affinity tags/labels. Affinity tags may include immuno-tags or haptens. For example, one or more of the nucleotides contained within the probe sequence may be biotinylated (either with biotin or a suitable analogue thereof—e.g. desthiobiotin). Alternative affinity labels may include digoxigenin, dinitrophenol or fluorescein, as well as antigenic peptide 'tags' such as polyhistidine, FLAG, HA and Myc tags. For target sequences that are present in high copy number in the sample of interest, probes will typically comprise only a single type of affinity label. For targets of low concentration, such as single copy sequences in the genome of an organism, optionally the oligonucleotide probes of the invention may comprise more than one type of tag. The inclusion of more than one affinity tag in the probes of the invention can significantly increase the sensitivity of the process for targets present at low concentration.

Prior to the hybridization step, the chromatin can be partially enzymatically digested in order to increase the resolution and to facilitate the next step of the method, which involves 'pull-down' of the probe-target sequence hybrid. Alternatively, the chromatin can be fragmented by physical methods such as ultrasonication, or by a combination of physical and enzymatic approaches.

In embodiments of the invention involving a 'pull-down' step, this is facilitated by use of a binding moiety that engages the affinity tag and enables the hybridised sequences to be isolated. In case of a biotinylated probe sequence, isolation of the hybridised sequences can be effected in vitro by exposing the hybridised sequences to microbeads coated with streptavidin. In this way the hybridised sequences will bind to the beads and can be precipitated out of solution via a straightforward microcentrifugation step. Alternatively the microbeads may comprise a magnetic component allowing for immobilisation of the beads via exposure to a magnetic field (see FIG. 2A). Alternative isolation strategies include the immobilisation of the probes on a solid substrate such as a microarray support or a dipstick. In this way the 'pull down' is facilitated by localisation to a specific area on a surface, which can then be suitably adapted so as to be suitable for use in later surface-enhanced laser desorption ionization time-of-flight mass spectrometry (SELDI-TOF-MS) analysis of the associated polypeptides.

The purified, or 'pulled-down' hybridised sequences comprise affinity labelled probe hybridised to the target nucleic acid sequence, including ncRNAs, together with any associated chromatin polypeptides, proteins and polypeptide complexes that are bound to the target sequence. These associated chromatin polypeptides, proteins and polypeptide complexes can be isolated from the pulled-down material by standard protein precipitation steps and, if required, separated via electrophoretic (e.g. SDS-PAGE) or chromatographic techniques (e.g. HPLC).

The chromatin associated proteins, polypeptides and nucleic acids can be analysed to determine their identity such as via high throughput identification protocols suitably including the mass spectrometry based technique of peptide mass fingerprinting (PMF). Alternatively, qualitative changes in the composition of known chromatin associating complexes can be monitored using antibody array technologies that are directed to constituent members of the complexes of interest.

It will be appreciated that the method of the invention is not limited to a specific type of non-coding RNA (nc-RNA) and can be directed a virtually any nucleic acid target which comprises an exposed region in order to identify an associated protein, polypeptide or nucleic acid profile. In addition, for any given sequence the method can be employed at different times in development, in the cell cycle or following exposure of the cell to external stimuli. As such, the method of the invention can allow for detailed profiling of the change in factors associated with a specific target sequence to be monitored. Moreover, the method of the invention allows for the identification of novel DNA and chromatin associated proteins, polypeptide and nucleic acid factors, many of which may be known but hitherto not considered as having epigenetic, DNA binding or chromatin-associating activities. In addition to providing information on the identity of proteins and nucleic acids bound to a locus, the present invention provides information on the relative levels of abundance of factors bound to a given sequence in distinct cell types.

Identification of the protein and polypeptide factors found to be associated with the specified target sequence can be achieved through a number of routes. Typically the proteins and polypeptides are separated from the probe-target sequence hybrid by conventional protein extraction techniques. The proteins/polypeptides are then suitably purified broadly according to molecular weight. The separated proteins can be analysed by several methods to determine identity including western blotting. However, where the output of the method of the invention is expected to reveal one or more novel factors, mass spectrometry based techniques for protein identification are appropriately utilised. For instance, protein samples can be derived from SDS-PAGE and then optionally subjected to further chemical modification, such as reduction of disulfide bridges carboxymethylation of cysteine amino acid residues. The proteins/polypeptides are then cleaved into several fragments using a suitable proteolytic enzyme, such as trypsin. The proteolysis step is typically carried out overnight and the resulting cleaved peptides are then extracted with acetonitrile and dried under vacuum. The peptides are then dissolved in a small volume of distilled water and are ready for mass spectrometric analysis. Mass spectrometry can be performed on an aliquot of the purified peptide cleavage fragments via MALDI-TOF mass spectrometry. The output from the MALDI-TOF is then typically analysed in silico, using bioinformatics analytical techniques, and used to query online protein databases such as GenBank or SwissProt in order to identify and provide sequence information for the novel factor (for example, see Griffin et al. (1995) Rapid Commun. Mass Spectrom. 9(15):1546-51; and Courchesne & Patterson (1999) Methods Mol. Biol. 112: 487-511).

Typically the mass spectrometry based techniques for polypeptide identification are referred to as peptide mass fingerprinting "PMF" after Pappin et al. (Curr Biol. (1993) June 1; 3(6):327-32). PMF can identify proteins by matching the molecular masses of constituent fragments (peptide masses) to theoretical peptide masses generated for polypeptides in silico. The premise of PMF is that every polypeptide will possess a unique set of peptide fragments each with unique peptide masses. Identification of a given polypeptide is accomplished by matching the obtained peptide masses to the theoretical masses present in a PMF sequence database. PMF identification is optimised where there are several peptide fragments obtained from a given protein the mass of which is accurately known. Hence, MALDI-TOF mass spectrometry provides a particularly accurate means to determine the mass of each of these peptide fragments. Proteomic approaches can be used to determine the nature of protein complexes that are composed from the peptides and proteins identified via mass spectrometry (for example see Gingras et al. Nat Rev Mol Cell Biol. (2007) August; 8(8):645-54).

By the term "modulator" it is meant a molecule (e.g. a chemical substance/entity) that effects a change in the activity of a target molecule (e.g. a gene, enzyme etc.). The change in activity is relative to the normal or baseline level of activity in the absence of the modulator, but otherwise under similar conditions, and it may represent an increase or a decrease in the normal/baseline activity. The modulator may be any molecule as described herein, for example a small molecule drug, an antibody or a nucleic acid. In the context of the present invention, the target is a novel chromatin associated factor that has been identified according to screening method of the invention. The modulation of chromatin-associated factor may be assessed by any means known to the person skilled in the art; for example, by identifying a change in the expression of genes regulated by the chromatin associated factor.

The present invention also relates to methods and compositions for the treatment of diseases associated with modified expression of one or more of the novel chromatin associated factors identified according to the method of the present invention.

Reagents for the inhibition of expression and/or biological activity of a specified chromatin associated factor include, but are not limited to, antisense nucleic acid molecules, siRNA (or shRNA), ribozymes, small molecules, and antibodies or the antigen binding portions thereof. For a review of nucleic acid-based technologies see, for example, Kurreck, J. (2003) "Antisense technologies—Improvement through novel chemical modifications", *Eur. J. Biochem.* 270: 1628-1644. The reagents for inhibition of the chromatin associated factor may affect expression and/or biological activity indirectly; for example, by acting on a factor that affects gene expression or that modifies or inhibits the biological activity of the novel chromatin associated factor. Advantageously, the reagent for use as an inhibitor of one of the novel chromatin associated factors identified herein acts directly on the chromatin associated factor, to affect gene expression at the mRNA level (e.g. transcription or mRNA stability), or the protein level (e.g. translation or biological activity).

Antisense nucleic acid sequences can be designed that are complementary to and will hybridise with a given mRNA in-vivo. Antisense nucleic acid sequences may be in the form of single stranded DNA or RNA molecules that hybridise to all or a part of the sequence of mRNA for the specified chromatin associated factor. Typically, an antisense molecule is at least 12 nucleotides in length and at least 90%, 93%, 95%, 98%, 99% or 100% complementary to the chosen target nucleotide sequence. Antisense oligonucleotides can be of any reasonable length, such as 12, 15, 18, 20, 30, 40, 50, 100, 200 or more nucleotides, having the advantageous above-mentioned complementarity to its corresponding target nucleotide sequence.

An antisense oligonucleotide may contain modified nucleotides (or nucleotide derivatives), for example, nucleotides that resemble the natural nucleotides, A, C, G, T and U, but which are chemically modified. Chemical modifications can be beneficial, for example, in: providing improved resistance to degradation by endogenous exo- and/or endonucleases, to increase the half-life of an oligonucleotide in vivo; enhancing the delivery of an oligonucleotide to a target cell or membrane; or increasing the bioavailability of an oligonucleotide. Typically, an antisense molecule contains a mixture of modified and natural nucleotides, and in particular, the 5' most and/or the 3' most nucleotides (e.g. the two outermost nucleotides at each end of the strand) may be modified to increase the half-life of the antisense molecule in vivo. In addition, or in the alternative, the backbone of an antisense molecule may be chemically modified, e.g. to increase resistance to degradation by nucleases. A typical backbone modification is the change of one or more phosphodiester bonds to a phosphorothioate bonds. An antisense molecule may suitably also comprise a 5' cap structure and/or a poly-A 3' tail, which act to increase the half-life of the antisense molecule in the presence of nucleases.

Antisense oligonucleotides can be used to inhibit expression of one or more chromatin associated factors identified according to the method of the present invention in target tissues and cells in vivo. Alternatively, such molecules may be used in an ex vivo treatment, or in an in vitro diagnostic test.

Requirements for the design and synthesis of antisense molecules against a specific target gene (via its corresponding RNA sequence), methods for introducing and expressing antisense molecules in a cell, and suitable means for modifying such antisense molecules are known to the person of skill in the art.

For example, antisense molecules for use in therapy may be administered to a patient directly at the site of a tumour (for example, by injection into the cell mass of the tumour), or they can be transcribed from a vector that is transfected into the tumour cells. Transfection of tumour cells with gene therapy vectors can be achieved, for example, using suitable liposomal delivery systems or viral vectors (Hughes, 2004, *Surg. Oncol.,* 85(1): 28-35).

Another means of specifically down-regulating a target gene, such as a chromatin associated factor gene is to use RNA interference (RNAi). Naturally, RNAi is typically initiated by long double-stranded RNA molecules, which are processed by the Dicer enzyme into 21 to 23 nucleotides long dsRNAs having two-nucleotide overhangs at the 5' and 3' ends. The resultant short dsRNA molecules are known as small interfering RNAs (siRNAs). These short dsRNA molecules are then thought to be incorporated into the RNA-induced silencing complex (RISC), a protein-RNA complex, which acts as a guide for an endogenous nuclease to degrade the target RNA.

It has been shown that short (e.g. 19 to 23 bp) dsRNA molecules (siRNAs) can initiate RNAi, and that such molecules allow for the selective inactivation of gene function in vivo, for example, as described in Elbashir et al. (2001, *Nature,* 411: 494-498). Thus, this technique provides a means for the effective and specific targeting and degradation of mRNA encoding a chromatin associated factor in cells in vivo. Accordingly, the invention provides siRNA molecules and their use to specifically reduce or eliminate the expression in cells of one or more chromatin associated factors identified by the methods of the present invention.

As in the case of antisense and ribozyme technology, an siRNA or shRNA molecule for in vivo use advantageously contains one or more chemically modified nucleotides and/or one or more modified backbone linkages.

Pharmaceutical preparations of the invention are formulated to conform to regulatory standards and can be administered orally, intravenously, topically, or via other standard routes. The pharmaceutical preparations may be in the form of tablets, pills, lotions, gels, liquids, powders, suppositories, suspensions, liposomes, microparticles or other suitable formulations known in the art.

Thus, the invention encompasses the use of molecules that can regulate or modulate activity or expression of the novel chromatin associated factors of the invention for treating disease. Typically diseases associated with aberrant activity or expression of chromatin-associated factors will include: cancer, premature aging, inflammatory disease, autoimmune disease, virally induced diseases and infections and infertility.

Novel chromatin associated factors (polypeptides, nucleic acids or fragments thereof) identified by the methods of the invention can be recombinantly expressed individually or in combination to create transgenic cell lines and purified factors for use in drug screening. Cell lines over-expressing the chromatin associated factors or fragments thereof can be used, for example, in high-throughput screening methodologies against libraries of compounds (e.g. "small molecules"), antibodies or other biological agents. These screening assays may suitably be either cell-based assays, in which defined phenotypic changes are identified (analogous to calcium signalling in GPCR FLIPR screening), or can serve as the source of high levels of purified proteins for use in affinity-based screens such as radioligand binding and fluorescence polarisation.

It is apparent, therefore, that the information derived from the method of the present invention allows for the accurate identification of a chromatin activity for many factors in the cell. By providing a cellular context for these diverse factors, as well as information on potential co-factors and complex interactions, the present invention allows for a more focussed approach to drug discovery and target selection. The identification of the proteins and nucleic acids that interact with genomic regions of interest is also critical to the understanding of genome biology. These questions have previously been studied using genetics, biochemical characterization of soluble complexes, structural studies, chromatin immunoprecipitation, and cell biology. By establishing the 'chromatin formula' of factors bound at specific loci or to large multi-factorial complexes, the methods of the present invention significantly advance the characterization of chromosomes and epigenetics as a whole. Clearly, the methods of the present invention have the ability to identify factors that would be difficult to uncover using genetics because they either play vital roles elsewhere or are redundant (e.g. orphan receptors).

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to describe the present invention, in connection with percentages means±1%, ±5%, or ±10%.

In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

The present invention may be as defined in any one of the following numbered paragraphs.

1. A method for identifying one or more factors associated with a target nucleic acid sequence, wherein the one or more factors comprise at least one ribonucleic acid (RNA) sequence that is associated with the target nucleic acid sequence, the method comprising the steps of:
   (a) obtaining a sample that comprises the target nucleic acid sequence and the one or more factors associated with the target nucleic acid sequence;
   (b) contacting the sample with one or more capture probes, wherein the capture probes comprise a nucleic acid sequence and at least one affinity label, and wherein the capture probes specifically hybridise with the at least one RNA sequence;
   (c) providing conditions that allow the one or more capture probes to hybridise with the at least one RNA sequence so as to form a hybridization complex between the capture probe, the at least one RNA, the target nucleic acid sequence and the one or more factors associated with the target nucleic acid sequence;
   (d) isolating the hybridization complex by immobilising the hybridization complex via a molecule that interacts with the affinity label; and
   (e) analyzing the constituents of the isolated hybridization complex so as to identify the one or more factors associated with the target nucleic acid sequence.
2. The method of paragraph 1, wherein the target nucleic acid sequence is comprised within genomic DNA.
3. The method of paragraph 1, wherein the target nucleic acid sequence is comprised within chromatin.
4. The method of paragraph 1, wherein the target nucleic acid sequence is comprised within a gene.
5. The method of paragraph 1, wherein the target nucleic acid sequence is comprised within a regulatory sequence.
6. The method of paragraph 5, wherein the regulatory sequence is within a promoter.
7. The method of paragraph 5, wherein the regulatory sequence is within a coding region.
8. The method of paragraph 5, wherein the regulatory sequence is within a non-coding region.
9. The method of paragraph 1, wherein the one or more factors comprise at least one non-coding RNA (ncRNA).
10. The method of paragraph 1, wherein the one or more factors comprise at least one messenger RNA (mRNA).
11. The method of paragraph 1, wherein the one or more factors comprise at least one polypeptide.

12. The method of paragraph 1, wherein the at least one ribonucleic acid (RNA) sequence that is associated with the target nucleic acid sequence is a ncRNA.
13. The method of paragraph 1, wherein the at least one ribonucleic acid (RNA) sequence that is associated with the target nucleic acid sequence is an mRNA.
14. The method of paragraph 1, wherein the one or more capture probes comprise DNA.
15. The method of paragraph 1, wherein the one or more capture probes comprise at least one modified nucleotide analogue.
16. The method of paragraph 1, wherein the affinity label is selected from the group consisting of: biotin or an analogue thereof; digoxigenin; fluorescein; dinitrophenol; and an immunotag.
17. The method of paragraph 16, wherein the biotin analogue is desthiobiotin.
18. The method of paragraph 1, wherein the probe-target hybrid is immobilized through a molecule that binds to the at least one affinity label and which molecule is attached to a solid substrate.
19. The method of paragraph 18, wherein the solid substrate comprises a microbead.
20. The method of paragraph 19, wherein the microbead is capable of being magnetically separated from a solution.
21. The method of paragraph 1, wherein the one or more factors associated with the target nucleic acid sequence are exposed to conditions that result in crosslinking of the one or more factors prior to the step (c) of exposing the sample to the capture probe, and wherein the crosslinking is reversed prior to the step (e) of analyzing the constituents of the isolated hybridization complex so as to identify the one or more factors associated with the target nucleic acid sequence.
22. The method of paragraph 1, wherein the conditions that allow the one or more capture probes to hybridise with the at least one RNA sequence in part (c) comprise high ionic strength and high concentration of a denaturant compound.
23. The method of paragraph 22, wherein the denaturant compound is urea.
24. The method of paragraph 1, wherein the method comprises an additional pre-treatment step prior to step (a) in which the at least one ribonucleic acid (RNA) sequence that is associated with the target nucleic acid sequence is mapped in order to identify regions of the RNA that are accessible to hybridization with a capture probe.
25. The method of paragraph 24, wherein the mapping of the RNA sequence comprises exposing the RNA sequence to RNase H in the presence of one or more complementary DNA oligonucleotides, determining the location of any RNase H cleavage sites that result from hybridization of the RNA to the one or more complementary DNA oligonucleotides, and identifying the cleavage sites as regions of the RNA that are accessible to hybridization with a capture probe.
26. The method of paragraph 24, wherein mapping of the RNA sequence comprises determining whether the target RNA sequence co-purifies with chromatin when analysed in the form of a sheered chromatin extract.
27. The method of paragraph 26 where the co-purification is an anti-histone RNA-immunoprecipitation.
28. The method of paragraph 26, wherein the co-purification is from a DNA affinity epitope.
29. The method of paragraph 1, wherein the sample is from a cell.
30. The method of paragraph 1, wherein the cell is a eukaryotic cell.
31. The method of paragraph 1, wherein the cell is a mammalian cell.
32. The method of paragraph 31, wherein the mammalian cell is a human cell.
33. The method of paragraph 1, wherein the sample is obtained from human tissue.
34. A method for identifying one or more factors associated with a region of chromatin that comprises at least one genomic locus, wherein the one or more factors comprise at least one ribonucleic acid (RNA) sequence that is capable of associating with the at least one genomic locus, the method comprising the steps of:
    (a) obtaining a sample that comprises the region of chromatin and the one or more factors associated with the region of chromatin;
    (b) contacting the sample with one or more capture probes, wherein the capture probes comprise a nucleic acid sequence and at least one affinity label, wherein the affinity label is conjugated to the one or more capture probes via a spacer group, and wherein the capture probes specifically hybridise with the at least one RNA sequence;
    (c) providing conditions that allow the one or more capture probes to hybridise with the at least one RNA sequence so as to form a hybridization complex between the capture probe, the at least one RNA, the target nucleic acid sequence and the one or more factors associated with the target nucleic acid sequence, wherein the conditions comprise high ionic strength and the presence of high concentration of a denaturant compound;
    (d) isolating the hybridization complex by immobilising the hybridization complex via a molecule that interacts with the affinity label; and
    (e) analyzing the constituents of the isolated hybridization complex so as to identify the one or more factors associated with the target nucleic acid sequence.
35. The method of paragraph 34, wherein the region of chromatin comprises one or more of the group consisting of: a telomere; a centromere; euchromatin; heterochromatin; a gene; a repeat sequence; a heterologously inserted sequence; and an integrated viral genome.
36. The method of paragraph 34, wherein the at least one RNA is a non-coding RNA (ncRNA).
37. The method of paragraph 34, wherein the one or more factors comprise at least one polypeptide.
38. A method for identifying one or more factors associated with a region of chromatin that comprises at least one genomic locus, wherein the one or more factors comprise at least one ribonucleic acid (RNA) sequence that is capable of associating with the at least one genomic locus, the method comprising the steps of:
    (i) obtaining a sample that comprises the region of chromatin and the one or more factors associated with the region of chromatin;
    (ii) contacting the sample with one or more capture probes that specifically hybridise with the at least one RNA sequence, wherein the capture probes comprise a nucleic acid sequence and wherein the capture probes are immobilized on a solid substrate;
    (iii) providing conditions that allow the one or more capture probes to hybridise with the at least one RNA sequence so as to form a hybridization complex between the capture probe, the at least one RNA, the target nucleic acid sequence and the one or more factors associated with the target nucleic acid sequence, wherein the conditions comprise high ionic strength and the presence of high concentration of a denaturant compound; and (iv) analyzing the constituents of the isolated hybridization complex so as to identify the one or more factors associated with the target nucleic acid sequence.

39. The method of paragraph 38, wherein the solid substrate comprises a microbead.

40. A method for identifying one or more factors associated with a region of chromatin that comprises at least one genomic locus, wherein the one or more factors comprise at least one non-coding ribonucleic acid (ncRNA) sequence that is capable of associating with the at least one genomic locus, the method comprising the steps of:
   (a) mapping the at least one ncRNA sequence in order to identify regions of the ncRNA that are accessible to hybridization;
   (b) synthesizing one or more capture probes, wherein the capture probes comprise a nucleic acid sequence and at least one affinity label, wherein the affinity label is conjugated to the one or more capture probes via a spacer group, and wherein the capture probes are able to hybridize with the at least one ncRNA sequence in a region defined as accessible to hybridization by step (a);
   (c) obtaining a sample that comprises the region of chromatin and the one or more factors associated with the region of chromatin;
   (d) contacting the sample with one or more capture probes;
   (e) providing conditions that allow the one or more capture probes to hybridise with the at least one ncRNA sequence so as to form a hybridization complex between the capture probe, the at least one ncRNA, the target nucleic acid sequence and the one or more factors associated with the target nucleic acid sequence, wherein the conditions comprise high ionic strength and the presence of high concentration of a denaturant;
   (f) isolating the hybridization complex by immobilising the hybridization complex via a molecule that interacts with the affinity label; and
   (g) analyzing the constituents of the isolated hybridization complex so as to identify the one or more factors associated with the target nucleic acid sequence.

41. The method of paragraph 40, wherein step (a) comprises exposing the ncRNA sequence to RNase H in the presence of one or more complementary DNA oligonucleotides, determining the location of any RNase H cleavage sites that result from hybridization of the ncRNA to the one or more complementary DNA oligonucleotides, and identifying the cleavage sites as regions of the ncRNA that are accessible to hybridization.

42. An assay for identifying one or more factors associated with a target nucleic acid sequence, wherein the one or more factors comprise at least one RNA sequence that is associated with the target nucleic acid sequence, the assay comprising:
   (i) one or more capture probes, wherein the capture probes comprise a nucleic acid sequence and at least one affinity label, and wherein the nucleic acid sequence of the capture probes is complementary to and will specifically hybridize with at least a part of the at least one RNA sequence;
   (ii) a hybridization buffer solution for providing conditions that allow the one or more capture probes to hybridise with the at least one RNA sequence so as to form a hybridization complex between the capture probe, the at least one RNA, the target nucleic acid sequence and the one or more factors associated with the target nucleic acid sequence, wherein the conditions comprise high ionic strength and the presence of high concentration of a denaturant; and
   (iii) a label comprising set of instructions on how to perform the assay.

43. The assay of paragraph 42, wherein the affinity label is conjugated to the one or more capture probes via a spacer group.

44. The assay of paragraph 42, further comprising:
   (iv) a solid substrate that comprises a molecule that is capable of binding to the at least one affinity label and which molecule is attached to the solid substrate.

45. The assay of paragraph 44, wherein the solid substrate comprises a microbead.

46. The assay of paragraph 45, wherein the microbead comprises magnetic particles so that it is capable of being magnetically separated from a solution.

47. The assay of paragraph 42, further comprising a solution of RNase H.

48. An assay for identifying one or more factors associated with a target nucleic acid sequence, wherein the one or more factors comprise at least one RNA sequence that is associated with the target nucleic acid sequence, the assay comprising:
   (i) one or more capture probes, wherein the capture probes comprise a nucleic acid sequence and wherein the capture probes are immobilized on a solid substrate, and wherein the nucleic acid sequence of the capture probes is complementary to and will specifically hybridize with at least a part of the at least one RNA sequence;
   (ii) a hybridization buffer solution for providing conditions that allow the one or more capture probes to hybridise with the at least one RNA sequence so as to form a hybridization complex between the capture probe, the at least one RNA, the target nucleic acid sequence and the one or more factors associated with the target nucleic acid sequence, wherein the conditions comprise high ionic strength and the presence of high concentration of a denaturant; and
   (iii) a label comprising set of instructions on how to perform the assay.

49. The assay of paragraph 48, wherein the solid substrate comprises a microbead.

50. The assay of paragraph 49, wherein the microbead comprises magnetic particles so that it is capable of being magnetically separated from a solution.

51. The assay of paragraph 48, further comprising a solution of RNase H.

52. A method for identifying one or more genomic DNA target nucleic acids of a non-coding RNA sequence (ncRNA), comprising,
   a) treating a chromatin extract comprising the ncRNA, to thereby reversibly cross-link the ncRNA present in the extract to an associated genomic DNA target nucleic acid(s) present in the extract;
   b) contacting the extract from step a) with one or more capture probes specific to the ncRNA under conditions that allow the capture probes to specifically hybridize with the ncRNA to thereby form a hybridization complex comprised of the capture probe(s), the ncRNA and the associated genomic DNA target nucleic acid(s);

c) isolating the hybridization complex by immobilizing the one or more capture probes in the context of the hybridization complex; and
d) analyzing DNA in the hybridization complex to thereby identify the genomic DNA target nucleic acid(s).
53. The method of paragraph 52, wherein analyzing the hybridization complex comprises:
a) treating the hybridization complex to uncross-link the ncRNA and associated genomic DNA target nucleic acid(s); and
b) sequencing the genomic DNA target nucleic(s) acid present in the hybridization complex.
54. The method of paragraph 53, further comprising amplifying the genomic DNA target nucleic acid present in the hybridization complex prior to sequencing.
55. A method for identifying one or more factors associated with a non-coding RNA sequence (ncRNA), comprising,
a) treating a genomic DNA extract comprising the ncRNA, to thereby reversibly cross-link the ncRNA present in the extract to one or more associated genomic DNA target nucleic acids present in the extract;
b) contacting the extract from step a) with one or more capture probes specific to the ncRNA under conditions that allow the capture probes to specifically hybridize with the ncRNA to thereby form a hybridization complex comprised of the capture probe(s), the ncRNA and the associated genomic DNA target nucleic acid(s);
c) isolating the hybridization complex by immobilizing the one or more capture probes in the context of the hybridization complex; and
d) analyzing the hybridization complex for the presence of associated proteins or RNAs, to thereby identify factors associated with the ncRNA.
56. The method of paragraph 55, wherein analyzing step d) comprises performing western blot analysis of proteins present in the hybridization complex to thereby analyze the hybridization complex for the presence of associated proteins.
57. The method of paragraph 55, wherein analyzing step d) comprises performing PCR on RNA present in the hybridization complex to thereby analyze the hybridization complex for the presence of RNAs.
58. The method of paragraph 57, wherein analyzing step d) further comprises performing sequencing of the RNA present in the hybridization complex.
59. The method of any one of paragraphs 52-58, wherein the capture probes are DNA oligonucleotides.
60. The method of paragraph 59, wherein the capture probes comprise an affinity label and the hybridization complex is immobilized by binding of the affinity label to a specific binding partner.
61. The method of paragraph 60, wherein the affinity label is biotin.
62. A method for determining one or more oligonucleotide sequences for use in a capture probe for a specific ncRNA, for use in Capture Hybridization Analysis of RNA Targets (CHART), comprising:
a) preparing a reversibly cross-linked chromatin extract;
b) providing candidate oligonucleotides;
c) separately combining each of the candidate oligonucleotides of step b) to the reversibly cross-linked chromatin extract, the presence of RNase H, under conditions suitable for RNA hydrolysis of RNA-DNA hybrids, to thereby produce a chromatin-oligonucleotide mixture;
d) performing RT-qPCR on the chromatin-oligonucleotide mixture to detect RNAse H sensitivity; and
e) identifying a candidate oligonucleotide as a sequence for use as a capture probe for CHART when RNAse H sensitivity in step d) is detected.
63. The method of paragraph 62, wherein the reversibly cross-linked chromatin extract of step a) is prepared by formaldehyde cross-linking.
64. The method of paragraph 62, wherein the candidate oligonucleotides are between 15 and 25 nucleotides in length.
65. The method of paragraph 62, wherein the candidate oligonucleotides are 20 nucleotides in length.
66. The method of paragraph 62, wherein the RT-qPCR is performed with a primer set that amplifies a region of the target cDNA that includes the oligo probe, a control primer set for an unrelated RNA, and a control primer set designed to hybridize to a region representative of the ncRNA that is not RNAse H sensitive.
67. A kit comprising one or more capture probes optimized for use in Capture Hybridization Analysis of RNA Targets (CHART) for a specific ncRNA.
68. The kit of paragraph 67, wherein the capture probes are optimized for a specific stage of development within a cell.
69. The kit of paragraph 67, wherein the capture probes are optimized for a specific cell type.

The invention is further illustrated by the following non-limiting example.

EXAMPLES

Example 1

Capture Hybridization Analysis of RNA Targets (CHART)

This Example describes an affinity purification strategy of one aspect of the invention that allows the specific enrichment of RNAs, including non-coding RNAs (ncRNAs) and mRNAs, along with their associated factors.

The CHART process is exemplified in more detail below.

Materials and Methods

Cell Culture. Drosophila S2 cells stably transfected with a plasmid expressing MSL3-TAP (Alekseyenko et al. High-resolution ChIP-chip analysis reveals that the Drosophila MSL complex selectively identifies active genes on the male X chromosome. Genes & Development (2006) vol. 20 (7) pp. 848-57) were grown in shaker flasks in serum-free CCM3 medium (Hyclone). HeLa cells were grown in suspension under standard conditions using DMEM supplemented with 10% Calf Serum.

Initial cross-linking. Cells were harvested by centrifugation (500 g, 15 min), rinsed once with cold PBS and resuspended in PBS (200 mL for $10^{10}$ S2 cells or $5\times10^8$ HeLa cells). Formaldehyde was added to 1% final concentration, and the suspension was allowed to rotate end-over-end for 10 min at room temperature. The cells were captured by centrifugation, rinsed three times with cold PBS and used immediately or aliquoted ($1\times10^8$ HeLa cells or $2\times10^9$ S2 cells), flash frozen in liquid N2 and stored at −80° C.

Extract preparation. On ice, each cell pellet as resuspended in 4 mL of cold sucrose buffer (SB, 0.3 M sucrose, 10 mM HEPES•KOH pH 7.5, 100 mM KOAc, 0.5 mM spermidine, 0.15 mM spermine, 1% Triton-X, 1 mM DTT, 10 units/mL SUPERasIN, 1× Roche complete EDTA-free protease inhibitor cocktail), subjected to 10 strokes with a tight pestle in a dounce homogenizer (15 mL, Weaton). After 5 min incubation on ice, the mixture was subjected to 10 additional strokes. Then an equal volume of cold glycerol buffer (GB, 25% glycerol, 10 mM HEPES pH 7.5, 100 mM KOAc, 1 mM EDTA, 0.1 mM EGTA, 0.5 mM spermidine, 0.15 mM spermine, 1 mM DTT, 10 units/mL SUPERasIN, 1× Roche complete EDTA-free protease inhibitor cocktail), was added to the cell material, and this mixture was layered over GB (4 mL) in a 15 mL conical tube. Enriched nuclei were collected by centrifugation (1000 g, 15 min) and the supernatant discarded. This pellet of enriched nuclei was resuspended in SB (4 mL), dounced, layered over GB and centrifuged as before.

For RNase H mapping, the nuclei were either processed directly without further crosslinking, or crosslinked further. For CHART, the pellet was crosslinked further as follows. The enriched nuclei were rinsed twice with nuclei rinse buffer (NRB, 50 mM HEPES pH 7.5, 75 mM NaCl, 10 units/mL SUPERasIN). This pellet was then resuspended in NRB (40 mL) and of concentrated formaldehyde added (10 mL of 16% w/v, MeOH free). This mixture was incubated with rotation at room temperature for 30 min. After crosslinking, the enriched nuclei were rinsed two times with NRB, and once with either wash buffer with 100 mM NaCl (WB100, 100 mM NaCl, 50 mM HEPES pH 7.5, 0.1% SDS, 0.05% N-lauroylsarcosine) or sonication buffer (for RNase H mapping, 50 mM Tris 8.2, 75 mM KCl, 0.5% N-lauroylsarcosine, 0.1% sodium deoxycholate, 1 mM DTT, 10 units/mL SUPERasIN, 1× Roche complete EDTA-free protease inhibitor cocktail). The pellet was resuspended to 3 mL total volume in the same buffer and the chromatin solubilized using a Misonix 3000 sonicator (microtip, 10 min treatment, 15 sec on, 45 seconds off, power level between 4-7 to maintain 35-45 W power) on ice. After sheering, the extract was cleared by centrifugation (16,100 g, 10 min, rt). The extract was either used immediately for CHART or flash frozen and stored at −80° C. For nuclei that were used without further crosslinking, instead of sonication, the nuclei were solubilzed using a Covaris instrument (30 min., 10% duty cycle, intensity of 5).

RNase H mapping. Crosslinked chromatin extract was thawed on ice and supplemented with SUPERasIN (1 unit/μL), MgCl2 (3 mM), DTT (10 mM) and RNase H (0.5 units/μL, NEB). The extract was dived into 10 μL reactions in strips of PCR tubes, and to each tube a different oligonucleotide was added (1 μL of 100 μM). The reactions were allowed to proceed for 30 min at 37° C. in a PCR block. Then DNase (1 μL RQ, Promega) and $CaCl_2$ (0.1 μL of 60 mM) were added. The reaction proceeded for an additional 10 min at 37° C. before adding proteinase K (2 μL of 10 mg/mL Proteinase K, 125 mM EDTA, 2.5% SDS). The reactions were incubated at 55° C. for 1 h, then 65° C. for 30 min. RNA from the reactions were purified using PureLink RNA purification kit (Invitrogen) according to the manufacturer's directions including an on-column DNase treatment step. The RNA (7 μL from 30 μL eluant) was reverse-transcribed using VILO (Invitrogen) and analyzed by qPCR on an ABI 7500 instrument. The RNase H sensitivity was determined according to the formula:

$$\text{Ratio} = (\text{Efficiency}_{target\ RNA})^{(oligo\ Ct-control\ Ct)} / (\text{Efficiency}_{control\ RNA})^{(oligo\ Ct-control\ Ct)}$$

Capture oligonucleotide design and synthesis. All oligonucleotides were designed modified on the 3' termini with four oligoethyleneglycol spacers residues preceding desthiobiotin all bridged by phosphodiesters. Synthesis was accomplished using an Expidite DNA synthesizer using resin pre-charged with desthiobiotin tetraethyleneglycol phosphoramidite (Glen Research, cat. 20-2952-41) and C18-spacer phosphoramidite (Glen Research, cat. 10-1918-02) in addition to the conventional DNA phosphoramidites. After synthesis and cleavage from resin, the oligonucleotides were purified by virtue of their final DMT-protecting group using PolyPak II cartridges (Glen Research, 60-3100-10) according to the manufacture's directions.

Enrichment. Two thawed aliquots of extract (500 μL) were supplemented with SUPERasIN (5 μL of 200 u/μL), DTT (2.5 μL of 1M) and complete protease inhibitors. To each tube, 125 μL of urea buffer (8M urea, 200 mM NaCl, 100 mM HEPES pH 7.5, 2% SDS) was added followed by 750 μL of hybridization buffer (150 mM NaCl, 10×Denhardt's, 1.12 M Urea, 10 mM EDTA). This material was pre-cleared with 100 μL of ultralink streptavidin resin (Pierce, cat. 53117) for 30 min at rt in four total screw-cap spin columns (900 μL, Pierce). The liquids were collected by centrifugation (1200 g, 30 sec). Capture oligonucleotides were added and the solution aliquoted into PCR strips for hybridization. The liquids were subjected to heating to 55° C. for 20 min, 37° C. for 10 min, 45° C. for 60 min, 37° C. for 30 min and then rt for at least 10 min. The appropriate tubes were pooled and cleared by centrifugation (16,000 g, 10 min, rt). Pre-rinsed streptavidin-coated magnetic beads (150 μL, MyOne Dynabeads C1, Invitrogen, cat 650.02) were resuspended in ddH2O (100 μL) and urea buffer (50 μL) and combined with the hybridized extract. This mixture was allowed to incubate on a roller at room temperature overnight. The bead mixture was transferred to a fresh tube and captured with a magnet, rinsed 5 times with WB250 (250 mM NaCl, 50 mM HEPES pH 7.5, 0.1% SDS, 0.05% N-lauroylsarcosine) and eluted with 200 μL of biotin elution buffer (50 μL of 50 mM biotin diluted in 150 μL WB250) for 1 h at room temperature with shaking.

Analysis of nucleic acids. The eluant from the enrichment reaction was supplemented with SDS (1% final), Tris•HCl pH 7.2 (100 mM final) and proteinase K (0.5 mg/mL final). The reactions were heated at 55° C. for at least 1 h and then the temperature was raised to 65° C. for 30 min. For DNA analysis, the material was purified using a QIAquick kit and then treated with RNase A (NEB). For RNA analysis the material was purified using PureLink RNA purification kit (Invitrogen).

Sequence analysis. DNA fragments were isolated, further sheered (Lieberman-Aiden et al. Science 326, 289 (2009)), and sequenced (Illumina GAIIx) and uniquely mapped to the Drosophila genome (for example see Langmead et al. Genome Biol. 10, R25 (2009)). Peaks were identified using overlapped and filtered calls from MACS (Zhang et al. Genome Biol., 9, R137 (2008)) and BayesPeak (Cairns et al. Bioinformatics, 27, 713 (2011)).

qPCR analysis. CHART enriched material was assayed in comparison with supernatant from a no-oligo control (as a control for handling loss instead of input). In FIG. 4E the signals were normalized to supernatant signal and to signal for Act-5C:

$$\text{Fold enrichment} = \left( \frac{\text{efficiency}_{TARGET\ PRIMERS}^{C_{T,CHART}-C_{T,INPUT}}}{\text{efficiency}_{ACT-5C\ PRIMERS}^{C_{T,CHART}-C_{T,INPUT}}} \right)$$

In FIG. 5B-C, the yields are reported relative to supernatant signal without further normalization:

$$\text{Yield} = \left( \frac{\text{Input dilution factor}}{\text{efficiency}_{PRIMERS}^{C_{T,CHART}-C_{T,INPUT}}} \right)$$

In cases where the CT was not reached within 45 cycles, a value of 40 was assigned for purposes of analysis, thereby conservatively underestimating enrichment. Error bars represent the standard deviations of three replicates.

Analysis of proteins and polypeptides. The eluant from enrichment reaction was supplemented with SDS (1% final) and Tris•HCl pH 8.2 and heated to 95° C. for 30 min. Analysis was performed as for the PICh reaction as described previously.

Results

Design of Capture Oligonucleotides for CHART Analysis

Figure 4:
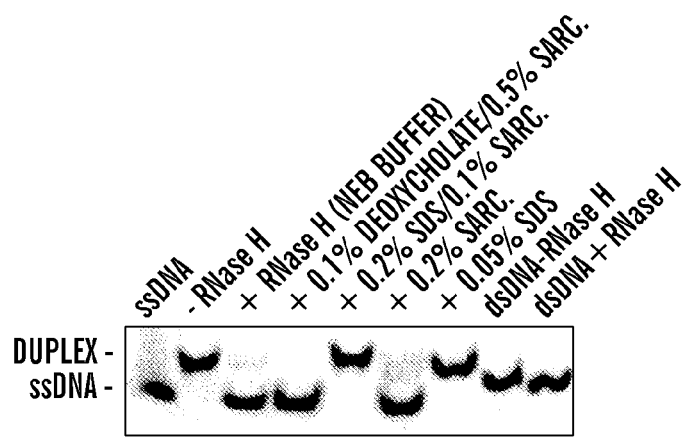
FIG. 4 shows an autoradiograph of an analysis of RNase H activity using synthetic nucleotides analyzed by native PAGE. A fluorescently labeled RNA-DNA duplex was incubated with RNase H under the various buffer conditions as labeled above the gel. As controls, the ssDNA, and lane without RNase H and two dsDNA controls are also shown.

To identify regions of the ncRNA accessible for hybridization, an RNase H mapping protocol was developed wherein accessible sites in the target ncRNA are assayed by their sensitivity to cleavage by RNase H in the presence of candidate complementary oligonucleotides. Since RNase H only cleaves DNA-RNA hybrids, the target RNA is only cleaved in the presence of DNA oligonucleotides capable of hybridizing to the target RNA. This strategy has been used to map sites of ncRNAs available for hybridization in native extracts. Since CHART is performed on formaldehyde crosslinked chromatin extracts, the RNase H mapping protocol needed to be adapted to identify sites available for hybridization in crosslinked extracts. To accomplish this, it was necessary to determine suitable conditions where the RNase H enzyme was active and the sheered chromatin extract was also soluble. Since the CHART strategy is based upon PICh, we first attempted to use the same extract and buffer conditions. However, PICh was performed with SDS present, and it was found that even low levels of SDS inhibited RNase H activity on model substrates. However, from screening the inventors identified conditions of high ionic strength and high levels of denaturation, such as with N-lauroylsarcosine and sodium deoxycholate, that both maintained chromatin solubility and did not interfere with RNase H activity (FIG. 4).

Figure 3A:
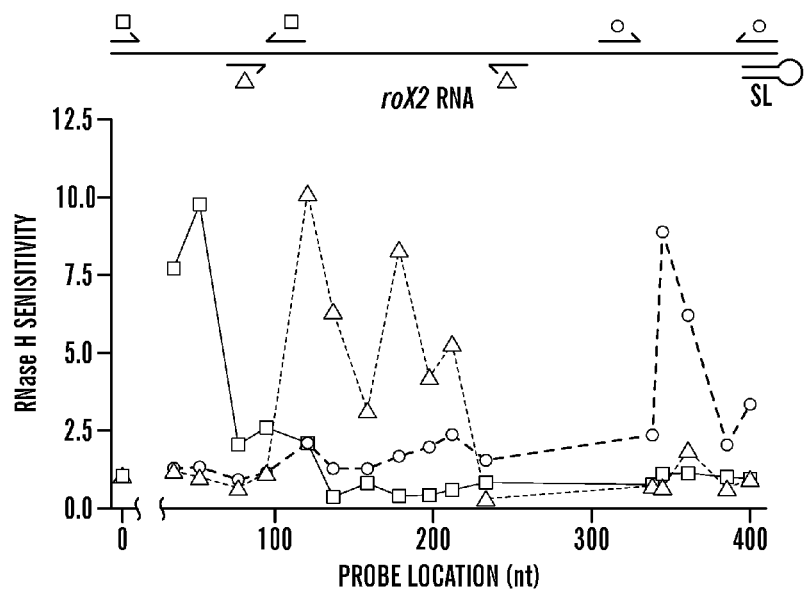
FIG. 3A shows enrichment of the indicated RNAs from HeLa chromatin extracts by either N, NEAT1 CHART; M, MALAT1 CHART; or O, a mock (no C-oligo) control as measured by RT-qPCR.
Figure 3B:
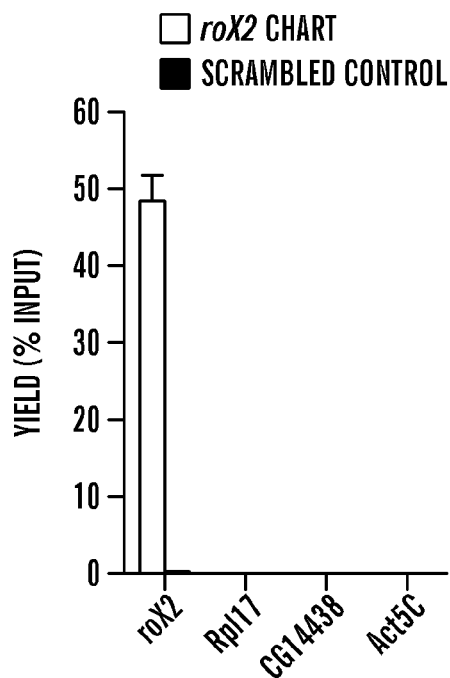
FIG. 3 shows (A) RNaseH mapping roX2 ncRNA was assayed with three primer sets by RT-qPCR, triangles (Δ) demarcate C-oligo sites, SL refers to a previously identified stem loop structure. Regions of high sensitivity were found to be sensitive only within appropriate primer sets. (B) Yields or roX2 RNA and control RNAs assayed by RT-qPCR (input normalized, SOM). (C) Yields relative to input of DNA from the indicated genomic loci for two negative loci, and two roX2 target loci. (D) Left: normalized reads (as FIG. 4B-C); right: view showing shape correspondence between roX2 CHART and MSL3-TAP ChIP data (without normalization). (E) Using the same peak-calling parameters, roX2 peaks are found to overlap largely with annotated CESs and MSL3-TAP ChIP-seq peaks.

As the first target, it was decided to focus on roX2 RNA. This approximately 500 nt ncRNA is an important regulator of dosage compensation in Drosophila and has been shown to function through a protein-nucleic acid complex referred to as the MSL complex. This ncRNA was chosen because it is abundant, has known protein binding partners and expected sites of interaction with the X-chromosome in a well established cell culture system (Gelbart and Kuroda. Drosophila dosage compensation: a complex voyage to the X chromosome. Development (2009) vol. 136 (9) pp. 1399-410). To map the regions of the roX2 ncRNA accessible for hybridization, 20mer DNA oligonucleotides were designed that tile the majority of the RNA. Upon the treatment of extract with individual 20mer oligonucleotides in the presence of RNase H, the cleavage of the roX2 target RNA was measured by RT-qPCR (FIG. 3A). Rnase H sensitivity was measured across the roX2 RNA. The cleavage was assayed both by primers that span the site of cleavage and ones that do not. Peaks of sensitivity were only observed using primers spanning the expected sites.

Figure 5:
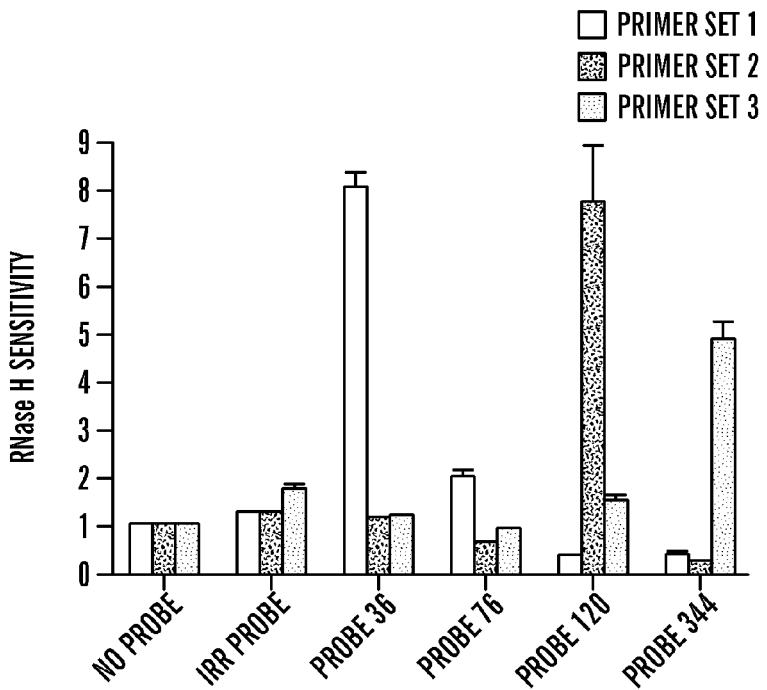
FIG. 5 shows results similar to the experiment in FIG. 3A but repeated in triplicate for several oligonucleotides.

To verify that these results were reproducible, sites of accessibility (e.g., probes 36, 120 and 134) and inaccessibility (e.g., probe 76) were verified in triplicate (FIG. 5). Furthermore, the cleavage was clearly site specific; the sensitivity was observed between the appropriate primer pairs, but not using primers that covered other regions of the RNA.

Furthermore, the cleavage was clearly site specific; the sensitivity was observed between the appropriate primer pairs, but not using primers that covered other regions of the RNA. The peaks in the RNase H sensitivity were used to design capture oligonucleotides complementary to roX2 RNA (see Table 1). The design of these oligonucleotides was initially based on the LNA-bearing ones used in PICh. However, after extensive optimization trying different nucleotide composition including locked nucleic acids (LNAs) or 2'-O-methyl modified RNAs, best results for the roX2 target were obtained from using a cocktail of three oligonucleotides where the nucleotide portion was composed of only DNA building blocks, but otherwise maintaining an analogous design to the PICh capture oligos including a linker group and a desthiobiotin moiety for affinity purification. It should be noted that for other ncRNA or mRNA targets of lower abundance, probes comprising one or more modified nucleotides (such as including locked nucleic acid, peptide nucleic acid, or 2'-O-alkyl-modified base analogues) may be more suited in order to obtain improved hybridization or yield.

TABLE 1

Capture oligonucleotides used in this Example. All sequences are listed 5' to 3'.

| | | |
|---|---|---|
| R2.1:   | TAA CAC CAA TTT ACC CTT TCG ATG LLL L-DSB | SEQ ID NO: 1 |
| R2.2:   | TCT CAC TGT CCG TAA GAC AAT TCA ALL LL-DSB | SEQ ID NO: 2 |
| R2.3:   | CTC TTG CTT GAT TTT GCT TCG GAG ALL LL-DSB | SEQ ID NO: 3 |
| CNTL:   | TAA TGG CTC CTA CAT ACT ACA TCT LLL L-DSB | SEQ ID NO: 4 |
| R2.AS1: | CAT CGA AAG GGT AAA TTG GTG TTA LLL L-DSB | SEQ ID NO: 5 |
| R2.AS2: | TTG AAT TGT CTT ACG GAC AGT GAG ALL LL-DSB | SEQ ID NO: 6 |
| R2.AS3: | TCT CCG AAG CAA AAT CAA GCA AGA GLL LL-DSB | SEQ ID NO: 7 |
| N1.1:   | GCT AGG ACT CAC ACT GGC CAG GGA CLL LL-DSB | SEQ ID NO: 8 |
| N1.2:   | TCC ATG TCT CCC GGT TCC ATC TGC TLL LL-DSB | SEQ ID NO: 9 |
| N1.3:   | CAT GAA GCA TTT TTG TAA CTT TCA GLL LL-DSB | SEQ ID NO: 10 |
| M1.1:   | GGA CTC TGG GAA ACC TGG GCT CCC GLL LL-DSB | SEQ ID NO: 11 |

TABLE 1-continued

Capture oligonucleotides used in this Example. All sequences are
listed 5' to 3'.

M1.2:  GAG GCG TCA GAG GGG ACC TGC CTT CLL LL-DSB  SEQ ID NO: 12

M1.3:  GCT GCT CCC CGC CTG AGC CCC GGG GLL LL-DSB  SEQ ID NO: 13

L indicates the spacer C18 residue. DSB stands for desthiobiotin--TEG.

Enrichment of roX2 by CHART

Optimization of the pull down was accomplished using the S2 Drosophila cell culture line that had been stably transfected with MSL3-TAP, a tagged protein with well-established interactions with the roX2 ncRNA. Upon affinity purification, the enriched material was assayed for enrichment of the roX2 RNA by RT-qPCR, expected genomic binding sites of the RNA (e.g., CES-5C2, Alekseyenko et al. A sequence motif within chromatin entry sites directs MSL establishment on the Drosophila X chromosome. Cell (2008) vol. 134 (4) pp. 599-609) and enrichment of the tagged MSL3 protein by western blot. Initial results using low salt PICh-like hybridization conditions proved unsuccessful due to low yields, high background or both. To accomplish high yields and purity several variables were optimised to increase yields, high salt (such as sodium chloride) and inclusion of crowding agents were favoured. Where high sodium chloride is used this is typically present in the hybridization buffer at a concentration of greater than about 100 mM and no more than around 1.5M, suitably no less than around 250 mM and no more than 1M, more suitably around 800 mM. However, these reagents also led to high background and precipitation of the chromatin extract. It was possible to maintain high yields but lower background and retain solubility by using high concentrations of denaturant (for example, urea) which serves both to solubilize the extract and decrease non-specific hybridization. Where urea is used as the denaturant it is typical that it should be present at a final reaction concentration of no less than around 0.5M and up to about 5M, suitably no less than around 1M and no more than about 3M, more suitably around 2M. It will be appreciated that the reaction conditions may be varied between the above mentioned parameters depending on the nature of the target sequence (e.g. the relative abundance of target in the sample material).

Figure 6A:
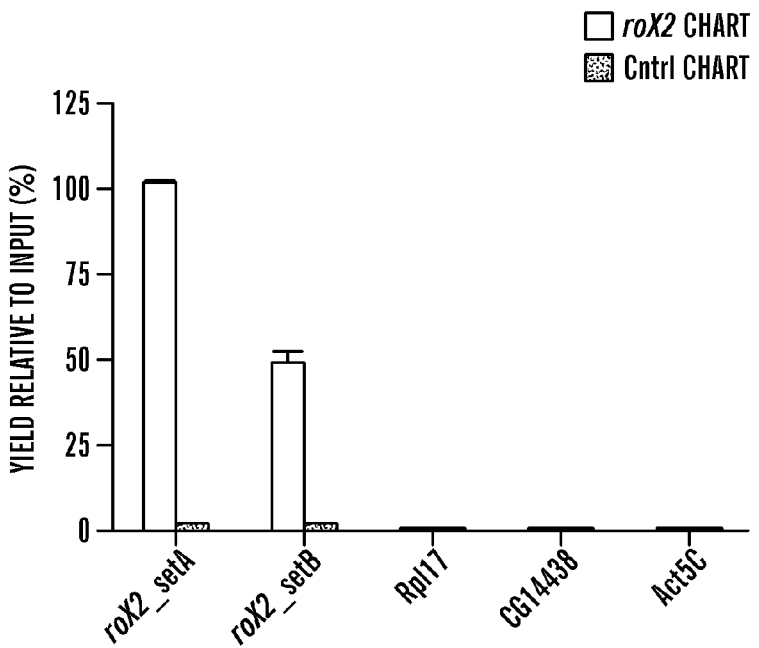
FIG. 6 shows (A) an analysis of RNA enriched by CHART using either capture oligos targeting roX2 (roX2 CHART) or a control CHART using a scrambled sequence (Cntrl CHART). The RNA enrichment was measured by RT-qPCR with primers against roX2 (two sets, A and B) and three other RNAs (Rp117, CG14438 and Act5C); and (B) a graph of qPCR validation of DNA enrichment from roX2 CHART normalized to genomic Actin-5C(SOM).
Figure 6B:
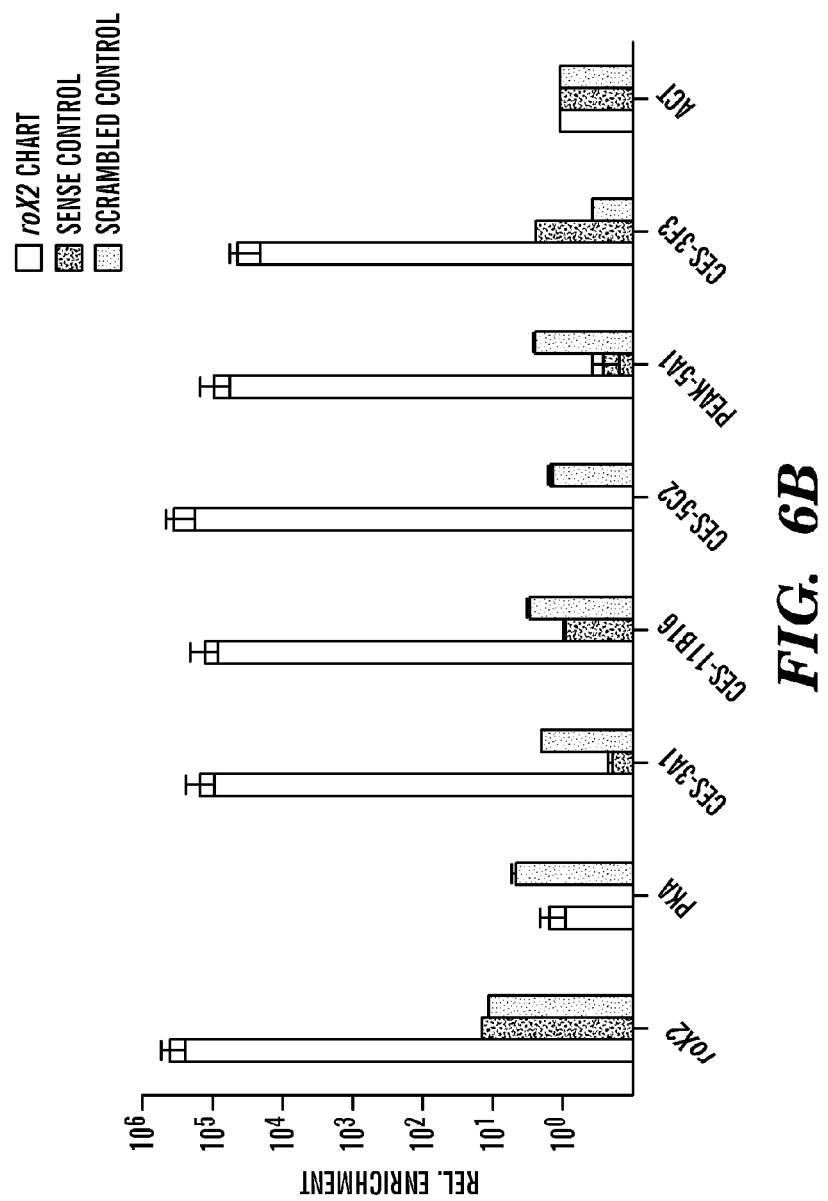

After optimization, the yields of RNA were high, showing 50% to near quantitative recovery of the roX2 target RNA, but not other RNAs (FIG. 6). Furthermore, this enrichment was only observed using probes specific for the roX2 RNA; a control, scrambled oligonucleotide did not significantly enrich the roX2 RNA demonstrating that the CHART protocol is highly specific for the targeted RNA.

Enrichment of roX2 Associated Proteins by CHART

Figure 7:
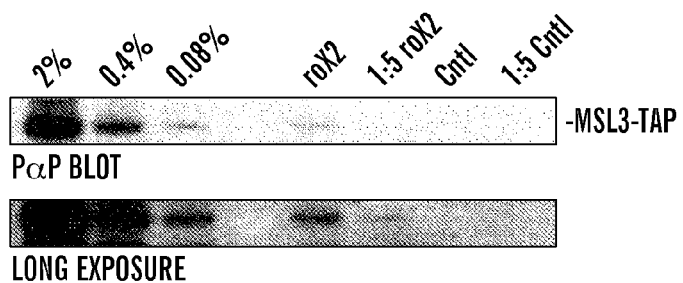
FIG. 7 shows an autoradiograph of a Western blot analysis of proteins co-purifying by CHART. Upper panel: the first three lanes represent the equivalent amount of a 2%, 0.4% or 0.08% yield, respectively. The enriched material was run along with a 1:5 dilution for either roX2 CHART or a control CHART experiment. The TAP-tag was visualized using a peroxidase•anti-peroxidase complex (PαP). Lower panel: is the same blot overexposed to visualize weaker bands.

Enrichment of the purified proteins was assayed by western blot. CHART led to the specific enrichment of the MSL3-TAP protein (FIG. 7). The pull down is specific, as the control scrambled CHART did not enrich for MSL3-TAP. Hence, roX2 targeted CHART is clearly able to enriche an associated protein. This appears to be general since another MSL protein, MLE was also specifically enriched by roX2 CHART. It is also possible to isolate associated ncRNAs and analyse these via techniques described, inter alia, in the inventors' co-pending international patent application published as WO-A-2010/093860, the contents of which are herein incorporated by reference.

Determining the Genomic Localization of roX2 Using CHART

Figure 8:
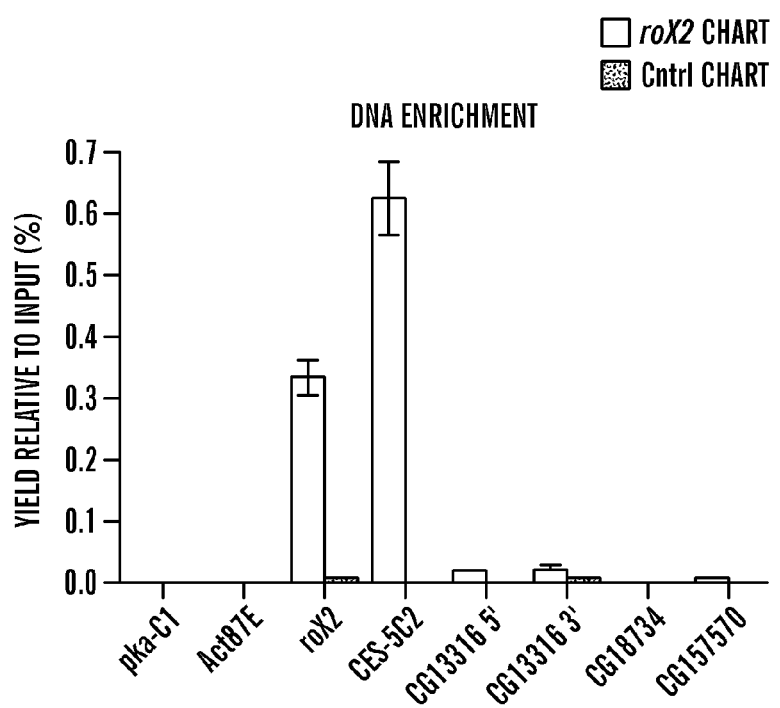
FIG. 8 shows a graphical analysis of the enrichment of DNA loci by CHART. Enriched material from either roX2 or control CHART was analyzed by qPCR using primers for either unrelated genes (pka-C1 and Act87E) the roX2 endogenous locus (roX2), a known chromatin entry site (CES-5C2), the 5' and 3' ends of a gene known to be dosage compensated (CG13316) and a gene on an autosome (CG15570) that is known to escape dosage compensation.

To determine where in the genome the roX2 ncRNA localises, the CHART enriched material was assayed by qPCR in a manner analogous to a ChIP experiment for a protein to look for enrichment of specific loci of the genome, especially known sites of MSL protein function. Indeed, roX2 was found to be enriched both at its own locus as well as at a well-characterized chromatin entry site (CES-5C2) as shown in FIG. 8. This enrichment was specific since other loci (pka-C1 and Act87E) and genes known to escape dosage compensation (CG15570) were not substantially enriched by roX2 CHART.

To further analyze the genomic localization of roX2 using CHART, the DNA resulting from the pull down was analyzed by deep sequencing to determine roX2 binding sites genome wide. These results were compared with a control CHART experiment, and the previous results of a MSL3-TAP ChIP experiment. A representative example from these data is shown in FIG. 2 (B-C). Sequencing of the DNA enriched by roX2 CHART revealed high-intensity peaks spread across the X-chromosome that were not present in control experiments (84% peaks on chrX), consistent with roX2's role in dosage compensation. These peaks were not due to direct capture of DNA by the C-oligos, as the peaks were not observed in a sense control. Further analysis of these peaks demonstrated high correspondence with targets of a subunit of the MSL-complex (MSL3) known to affect dosage compensation (FIG. 4D). Binding of roX2 was prominent at high affinity MSL-binding sites (e.g., Peak-5A1, FIGS. 2B & 6D) including chromatin entry sites (CESs). e.g., CES-5C2, FIG. 4B-E), which are thought to be the initial points of assembly of the complex before it spreads into flanking chromatin to regulate active genes. The roX2 CHART results demonstrate that the roX2 binding pattern is very similar to that of the protein components of the MSL complex, demonstrating that the CHART experiment can be used to study RNAs in a directly analogous way to a ChIP experiment.

Generality of CHART

Figure 9:
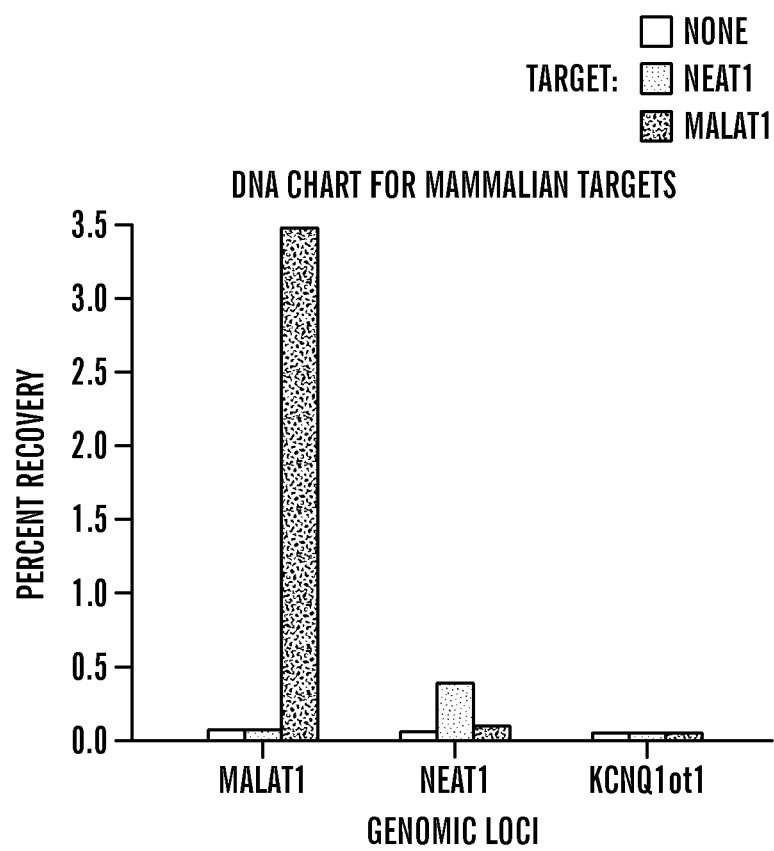
FIG. 9 shows a graphical analysis of DNA enrichment from NEAT1 or MALAT1 CHART experiments, compared with a no pull down control (None). qPCR primers specific for three different loci, including one unrelated loci (KCNQ1ot1) were used for analysis of the enriched DNA.

To examine if the protocol developed for roX2 will extend to other RNAs in other contexts, two mammalian RNAs were targeted from HeLa extracts (i.e. human cells), NEAT1 and MALAT1. These two ncRNAs neighbor each other in the genome, yet localize to distinct nuclear bodies. MALAT1 localizes to nuclear speckles whereas NEAT1 localizes to nuclear paraspeckles. While little is known about their interaction with chromatin and their expected interacting loci, all expressed RNAs are likely to be found at their site of transcription. Indeed, when CHART oligos were mapped using the protocol described here for each of these two targets (the oligos used are listed in Table 1 as SEQ ID Nos: 10-15). Using these capture oligos led to the enrichment of the appropriate endogenous loci for each target (FIG. 9), demonstrating the generality of CHART for different RNAs in different organisms as well as the ready applicability of the process to use in human cells. Furthermore since each RNA was dramatically enriched only at its own loci, this experiment also underscores the remarkable specificity of CHART.

Discussion

This protocol provides a systematic means of developing probe oligonucleotides that can function for RNAs in a manner similar to how antibodies have been used for proteins. While previously developed and now well-established technologies have used oligonucleotides to perform northern blots (in experiments analogous to western blots for proteins), and in situ hybridization (analogous to IF for proteins), other experiments that can currently be performed with protein targets such as co-IP, RIP and ChIP have not been generally available for RNAs. As demonstrated here, CHART provides the necessary technology to bridge this gap. CHART was demonstrated capable of enriching roX2 RNA along with its associated proteins and nucleic acids. As one exemplary application, CHART was used to create a genome wide map of the chromatin loci where roX2 ncRNA binds.

Importantly, CHART is not restricted to roX2 in flies; two mammalian RNAs have also been enriched with their associated factors using CHART. In its current state, it is possible to analyze candidate interacting protein and nucleic acid factors, and for nucleic acids CHART can already be used to discover new interactions. This technology could be useful also for mRNA analysis too, specifically for looking at localized mRNAs, the machinery that transports mRNAs and any other RNAs that are bound in the same complexes. With the use of proteomic techniques such as SILAC (stable isotope labeling by/with amino acids in cell culture), CHART can be extended to discover new protein factors that interact with a given target RNA. The experiments described herein were performed using cell numbers consistent with those routinely used in experiments such as ChIP; no special infrastructure is required and therefore any lab that currently performs ChIP experiments should be able to perform CHART. While the above-described protocol demonstrates success with an RNase H mapping step, certainly there is the potential for other methods including computational ones, or chemical mapping techniques, for example to inform design of capture oligo probes. In at least one embodiment of the invention capture oligos can be rationally designed based on a repeat structure.

In view of its currently demonstrated utility and generality, CHART can facilitate the understanding of the role of RNAs, including ncRNAs, in cellular biology.

Although particular embodiments of the invention have been disclosed herein in detail, this has been done by way of example and for the purposes of illustration only. The aforementioned embodiments are not intended to be limiting with respect to the scope of the appended claims, which follow. The choice of nucleic acid starting material, the clone of interest, or types of libraries used are believed to be a routine matter for the person of skill in the art with knowledge of the presently described embodiments. It is contemplated by the inventors that various substitutions, alterations, and modifications may be made to the invention without departing from the spirit and scope of the invention as defined by the claims.

Example 2

Background

Generating cellular diversity from genetic information requires the regulatory interplay between cis-acting elements encoded at specific loci in chromatin and trans-acting factors that bind them (1). Although the importance of trans-acting proteins (e.g., transcription factors) has long been appreciated, there is growing interest in the role of long noncoding RNAs (lncRNAs) (2) as factors that can regulate specific chromatin loci. This interest is enhanced by the recent discovery that the majority of eukaryotic genomes are transcribed (3) and that many of the resulting transcripts are developmentally regulated (4) but do not encode proteins. Although the functional scope of these RNAs remains unknown (5-7), several lncRNAs play important regulatory roles at the level of chromatin (8). Determining where these ncRNAs bind on the genome is central to determining their function.

Examples of lncRNAs that influence chromatin include the roX ncRNAs in flies and Xist in mammals, both having well-established roles in dosage compensation (8, 9); Kcnq1ot1 and Air ncRNAs, which are expressed from genomically imprinted loci and affect chromatin silencing (10-13); Evf2, HSR1, and other ncRNAs that positively regulate transcription (14-16); lncRNAs that target the dihydrofolate reductase promoter and the rDNA promoters through triplex formation (17, 18); and the human HOTAIR and HOTTIP lncRNAs, which regulate polycomb-repressed and trithorax-activated chromatin, respectively (19, 20). Dysregulation of several of these lncRNAs has been associated with disease (21, 22). Current understanding of the biochemical roles of these RNAs comes largely from their interactions with specific proteins—insights gained from classical biochemical techniques developed for studying translation and RNA-processing complexes and also more recent technological advances using RNA immunoprecipitation (23) and cross-linking and immunoprecipitation (24-26). These experiments suggest that several lncRNAs specifically interact with chromatin-modifying machinery and may act as scaffolds for multiple complexes (27) or as targeting modules to direct these complexes to specific chromatin loci (reviewed in refs. 28 and 29). There are various modes by which an RNA can interact with a chromatin locus, including direct interactions with the DNA (through canonical Watson-Crick base pairing or nonconical structures such as triple helices) or indirect interactions mediated through a nascent RNA or protein (28).

Determining the direct functions of lncRNAs requires knowledge of where they act. This requirement motivates the development of technology to generate genomic binding profiles of lncRNAs in chromatin that is analogous to chromatin immunoprecipitation (ChIP) for proteins. Ideally, this technology would (i) provide enrichments and resolution similar to ChIP, (ii) use cross-linking conditions that are reversible and allow for analysis of RNA, DNA, and protein from the same enriched sample, and (iii) provide adequate controls to distinguish RNA targets from the background signal. Although there are several techniques that localize RNAs on chromatin, none fulfill all these criteria. For example, both fluorescence in situ hybridization (FISH) (30) and a related biochemical approach (31), which relies on indirect biotinylation of biomolecules near the target RNA, are important techniques that localize RNAs to genomic loci, but neither has demonstrated high resolution across the genome. The ability of nucleic-acid probes to retrieve lncRNAs from cross-linked extracts has been shown (32), but it is unclear if the signal was RNA-mediated or rather due to direct interactions of the long capture oligos with complementary regions found in nearby DNA. Either way, the efficiency and specificity of these technologies have not allowed the precision required for high-resolution genome-wide profiling.

The development of CHART (capture hybridization analysis of RNA targets), a hybridization-based purification strategy that can be used to map the genomic binding sites for endogenous RNAs is reported herein. CHART is used to purify lncRNAs and their associated protein and DNA targets and to determine the genome-wide localization of roX2 RNA in chromatin. The work began by identifying regions of the target RNA available for hybridization to short, complementary oligonucleotides. Affinity-tagged versions of these oligonucleotides were then designed to retrieve the target RNA along with its associated factors from reversibly cross-linked chromatin extracts under optimized CHART conditions. By isolating and purifying the CHART-enriched DNA fragments, analogous to ChIP, CHART allows the identification of the genomic binding sites of endogenous RNAs (FIG. 1). These data definitively demonstrate that a lncRNA, roX2, localizes to the same sites across the genome as the chromatin-modifying protein complex with which it is proposed to act. Together, these data demonstrate the utility of CHART as a tool in the study of RNAs.

Results

Design and Development of CHART

Figure 10:
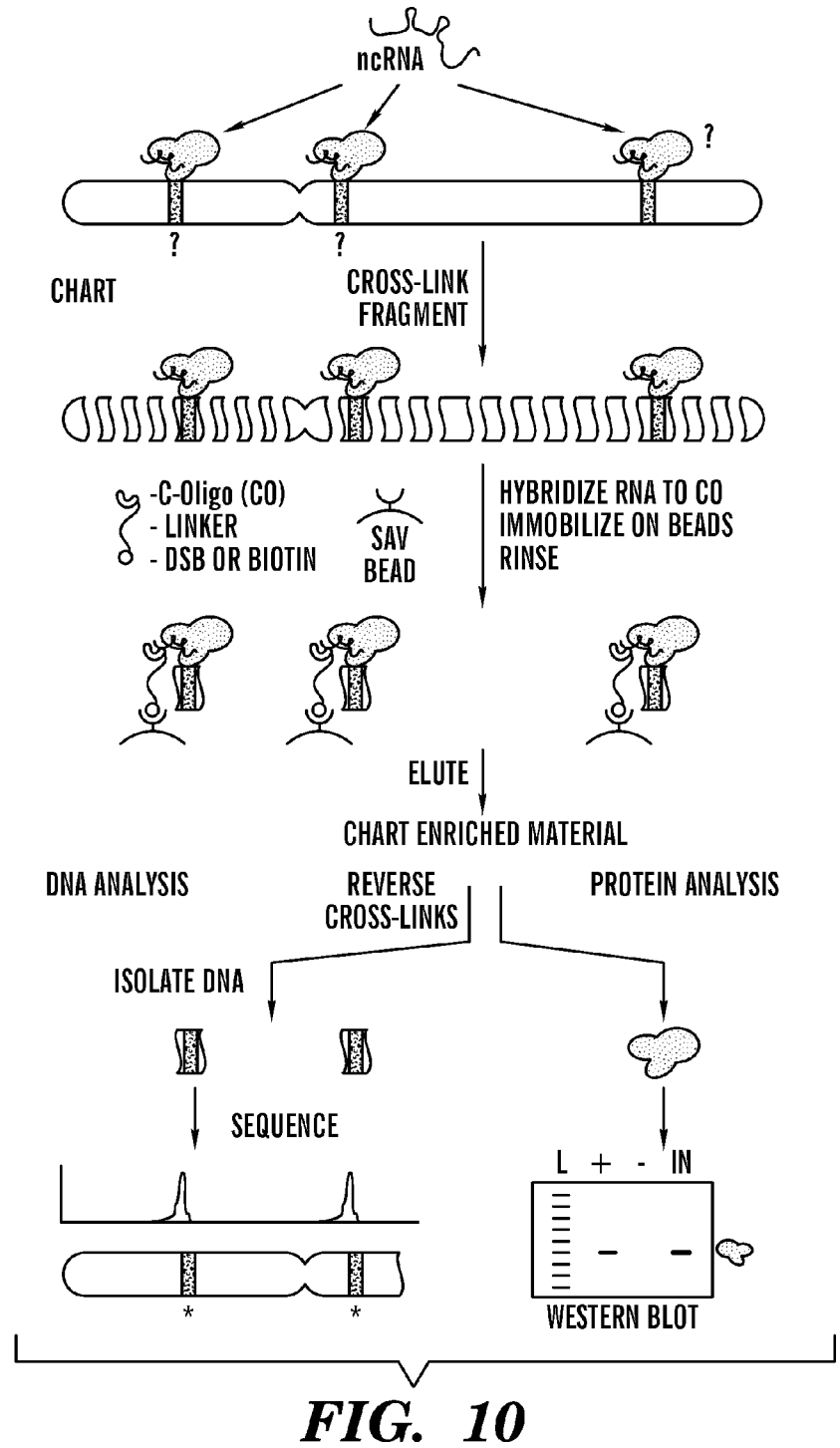
FIG. 10 shows a schematic of CHART, a hybridization-based strategy that uses complementary oligonucleotides to purify the RNA together with its targets from reversibly cross-linked extracts. The cartoon here shows the scenario where the RNA is bound in direct contact with the DNA together with proteins, but other configurations are also possible (see the text). CHART-enriched material can be analyzed in various ways; the two examples depicted here are (Left) sequencing the DNA to determine genomic loci where the RNA is bound and (Right) analyzing the protein content by Western blot analysis.

Affinity purification of an RNA together with its targets was attempted by using oligonucleotides that are complementary to the RNA sequence and developed this technology for roX2, an approximately 600-nt ncRNA that regulates dosage compensation in Drosophila (9). Guided by the success of a chromatin-purification strategy that uses short, affinity-tagged oligonucleotides (C-oligos) to enrich genomic loci through hybridization to DNA in cross-linked extracts (33), a similar strategy was pursued using C-oligos to capture endogenous roX2 RNA along with its associated targets in reversibly cross-linked extracts (FIG. 10).

Figure 14A:
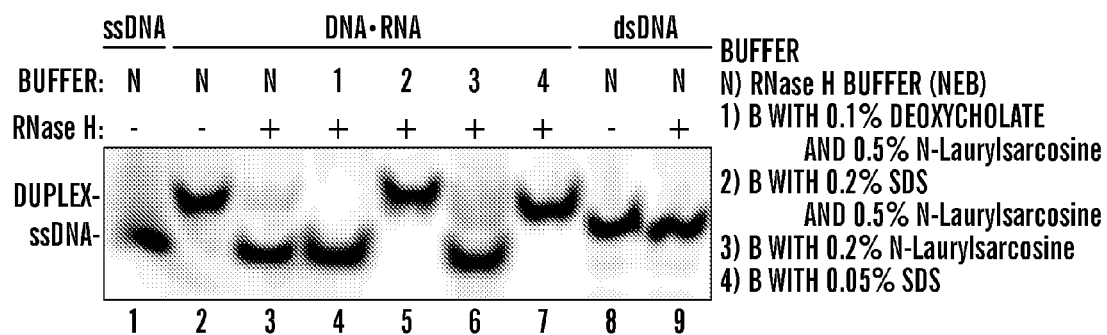
FIG. 14A shows analysis of RNase-H activity using synthetic nucleotides analyzed by native PAGE. A Cy5-fluorescently labeled DNA oligonucleotide was hybridized to either a complementary RNA (lanes 2-7) or DNA (lanes 8 and 9) or run without hybridization as a control (lane 1). These oligonucleotides were incubated with RNase H (5 U) under the indicated buffer conditions. Buffer B is 50 mM Hepes pH 7.5, 75 mM KCl, 3 mM MgCl2, 0.1 mM EGTA, 20 u/mL SUPERasIN, 5 mM DTT, 7.5% glycerol to which the indicated detergents were added. The reaction was incubated at 30° C. for 30 min and quenched with EDTA and Proteinase K. The products of the reaction were resolved by 10% native polyacrylamide gel and the gel scanned for Cy5-fluorescence on a Typhoon imager. From this analysis, buffer 1 conditions were chosen because these conditions were found to be compatible with RNase-H activity.
Figure 14B:
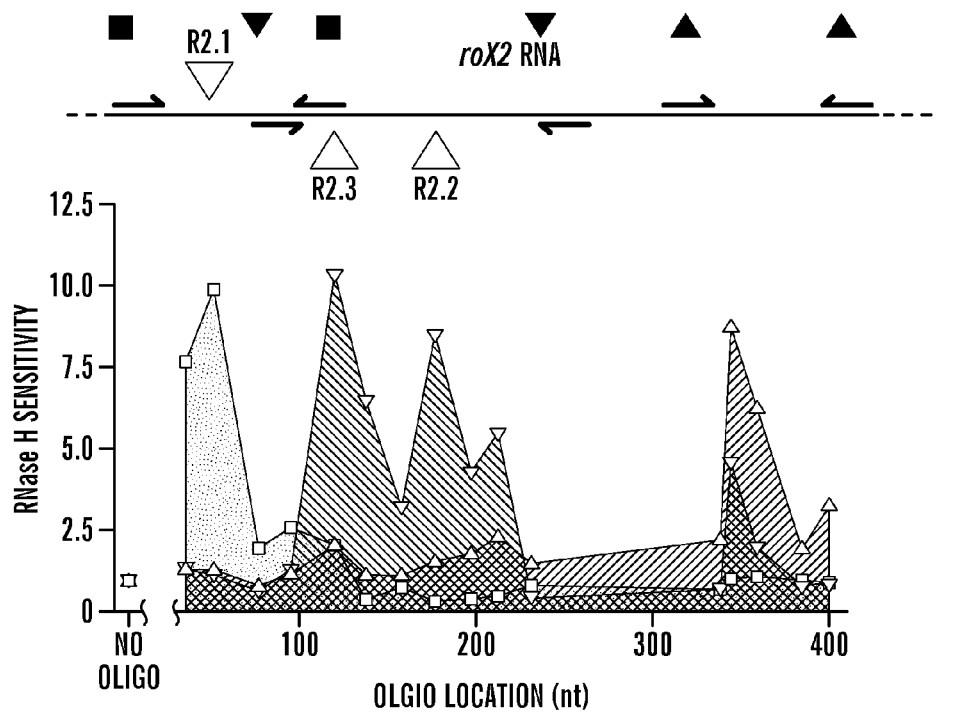
Figure 14C:
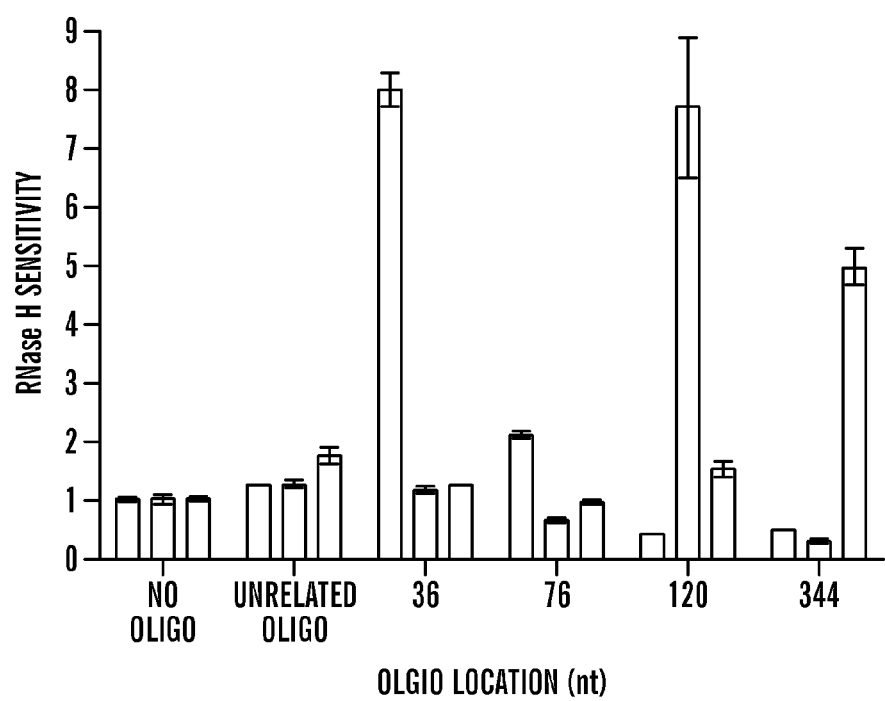
FIG. 14C shows the same as FIG. 14B but repeated in three independent experiments for each oligo shown. Error bars represent ±SEM.

Work was performed to first ensure that these C-oligos would target stretches of roX2 RNA available for hybridization and not occluded by protein binding or secondary structure. An RNase-H mapping assay (34-36) was adapted to probe sites on roX2 available to hybridization in the context of cross-linked chromatin extracts. RNase-H specifically hydrolyzes the RNA strand of a DNA-RNA hybrid (37). As RNase-His not active when exposed to the detergents present in many chromatin extraction procedures, assay conditions ideal for both solubilization of the chromatin and RNase-H mapping (Figure S1A) were determined. Exposing chromatin extracts to 20-mer DNA oligonucleotides one at a time and measuring hybridization to roX2 by sensitivity to RNase-H revealed regions of roX2 that were significantly and reproducibly more available for C-oligo hybridization than others (FIGS. 14B and C). These differences could be due to differences in accessibility of roX2 or to factors independent of roX2, such as other competing sequences in the extract. Because both roX2-dependent and roX2-independent mechanisms that lead to low RNase-H sensitivity could also interfere with efficient hybridization to C-oligos in the context of CHART enrichment, we focused on accessible sites with high RNase-H sensitivity for C-oligo design.

Figure 11A:
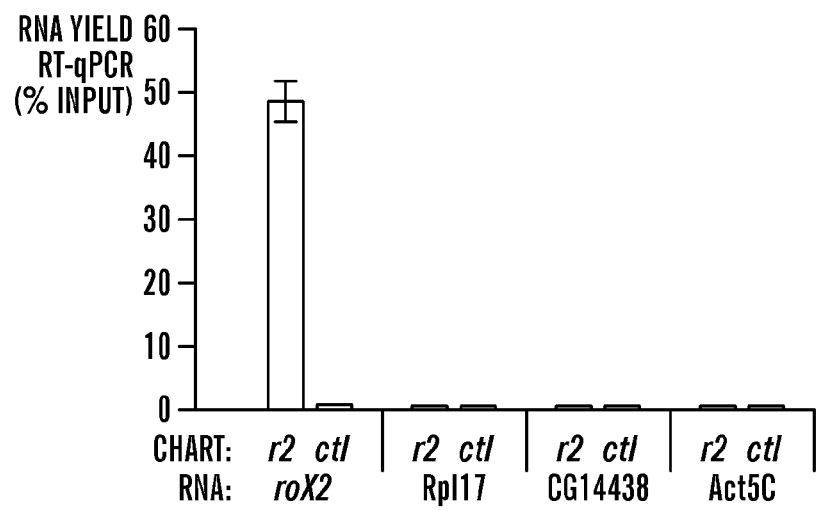
FIG. 11A-FIG. 11C show results from experiments that indicate CHART allows specific enrichment of roX2 along with its associated targets.
Figure 14D:
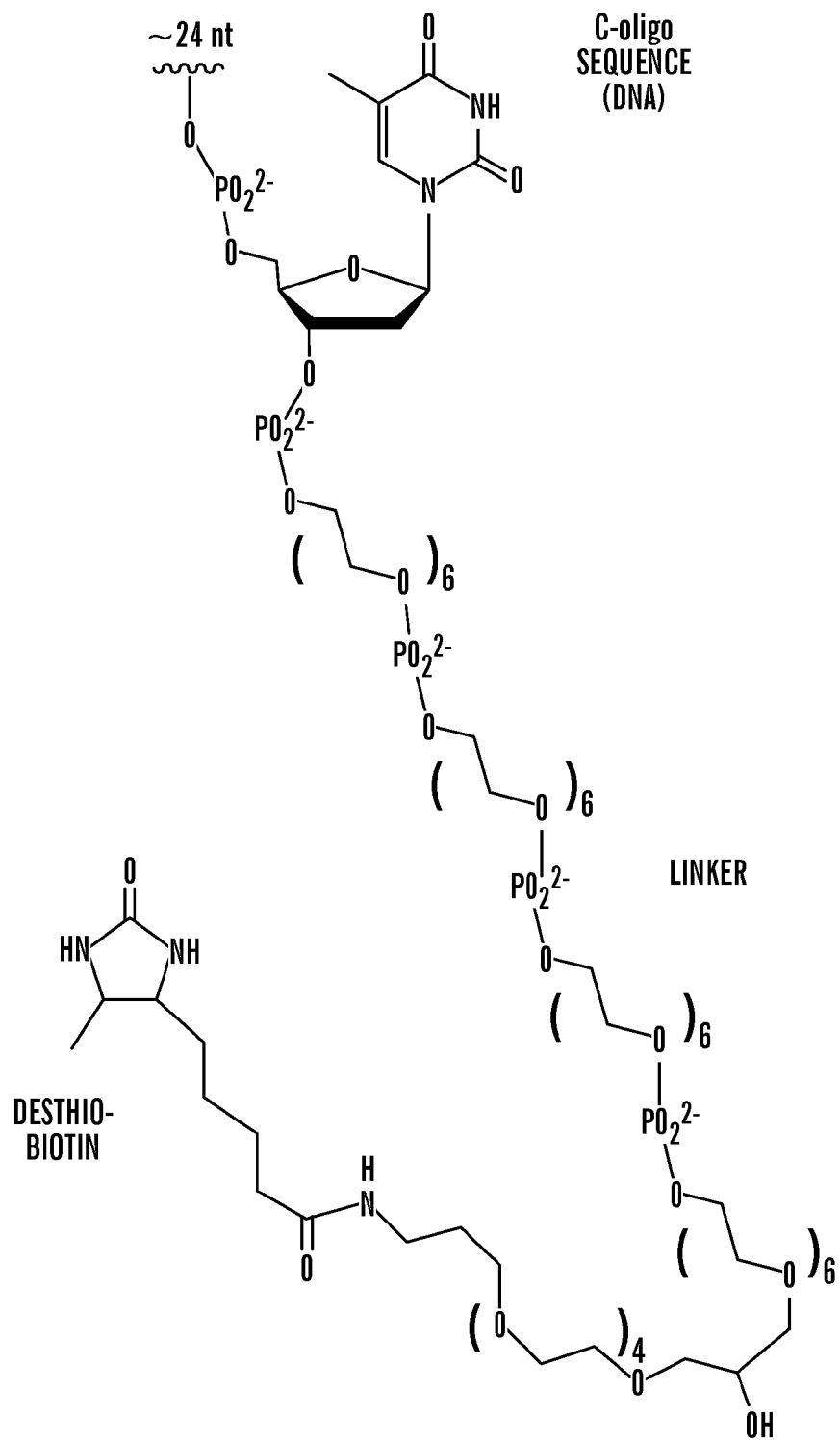

Conditions to specifically enrich roX2 RNA together with its associated targets were then developed by testing a range of hybridization conditions and C-oligo chemistries (including O2'-methylated ribonucleotides and locked nucleic acids) on the basis of related applications (33, 35, 38, 39). In these experiments, desthiobiotin-conjugated C-oligos (FIG. 14D), which allow for gentle biotin elution (33, 40) were used. Determining CHART hybridization conditions required balancing the solubility of the chromatin extract, the stability of duplex formed upon C-oligo binding to RNA, and the stringency required to directly capture only the desired RNA. Using the design illustrated in FIG. 14D, a cocktail of three approximately 25-mer DNA-based C-oligos was found to provide a low background signal and high specific yields of roX2 in a buffer with high ionic strength and high concentrations of denaturants (FIG. 11A). Approximately half of roX2 RNA input could be retrieved from the cross-linked chromatin extract. This enrichment was specific; CHART using a scrambled control C-oligo did not enrich roX2, and control RNAs were not enriched by roX2 CHART. It was concluded that DNA-based C-oligos hybridizing to RNase-H-sensitive locations on a target RNA can specifically enrich the RNAs from a cross-linked chromatin extract.

CHART Enrichment of roX2 Targets

Figure 11B:
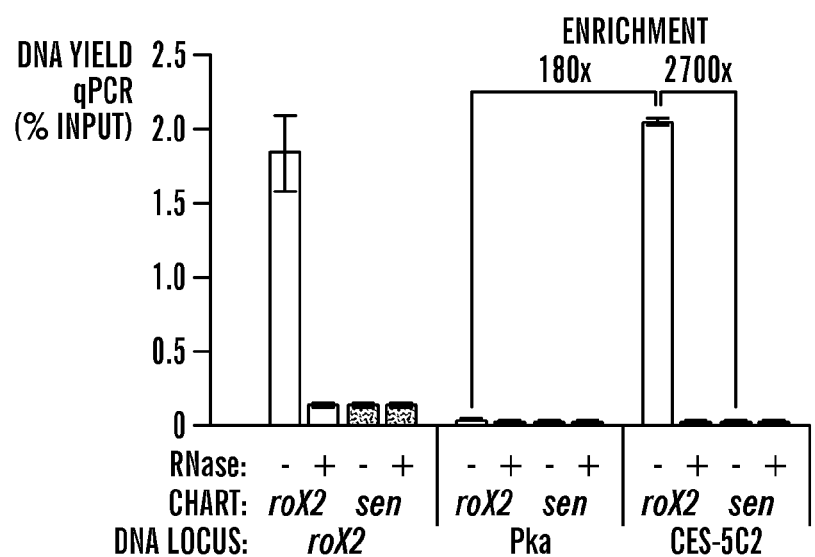

Having established CHART enrichment of roX2 RNA itself, whether proteins and DNA loci associated with roX2 were also enriched was then tested. Candidate genomic sites of roX2 binding were first examined. DNA was found to be enriched for both the endogenous roX2 locus and a known regulatory site of dosage compensation, chromatin entry site 5C2 (CES-5C2) (41) but not control sites (FIG. 11B). To test whether the CHART-enrichment of DNA was RNA-dependent, and not an artifact caused by hybridization of the C-oligos with cognate genomic DNA, the extract was treated with RNase prior to C-oligo hybridization. The majority of the enrichment at the endogenous locus (approximately 93%), and essentially all of the enrichment at the trans-acting locus (>99%), was RNA-mediated (FIG. 11B); only a minority of the DNA enriched at the endogenous roX2 locus (approximately 7%) could be accounted for by direct binding of the C-oligos to DNA. The RNA-mediated enrichment of the regulatory site (CES-5C2) was substantial (>100-fold over a control locus and >1000-fold over the sense-oligo control), and the yields (approximately 1-2%) were similar to those retrieved by ChIP.

Figure 15:
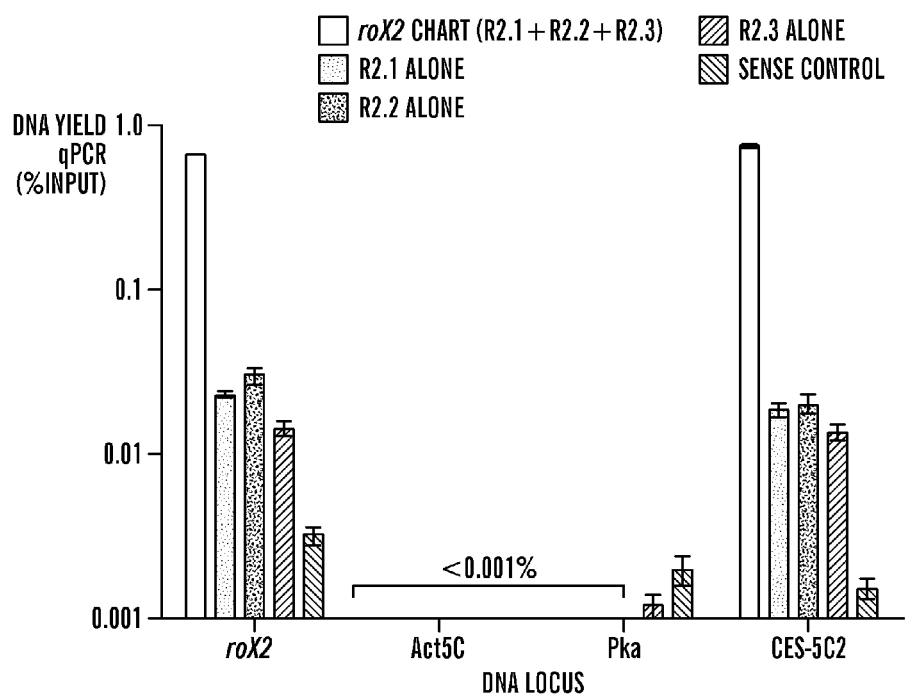
FIG. 15 shows data from experiments that indicate the C-oligos used in roX2 CHART each independently enrich roX2 binding sites and act synergistically. roX2 CHART was performed either with the standard mixture of three C-oligo nucleotides (white) or with the individual C-oligos (red, yellow, and blue). As a control, a mixture of three sense oligos corresponding to each of the roX2 C-oligo cocktail was used (gray). The results are plotted on a log 10 scale relative to input. The individual C-oligos each have yields greater than threefold lower (40-, 37-, and 56-fold lower, respectively) than the combined cocktail, demonstrating that the C-oligos act synergistically. Where indicated, the two negative-control loci (Pka and Act5C) amplified but did not achieve 0.001% yield (corresponding to a qPCR CT value of >35 with input CT values of approximately 20 for all four loci). Error bars represent ±SEM of three qPCR replicates.

As further support of the specificity of CHART, a control experiment using sense oligos (therefore not complementary to roX2 RNA) did not enrich the DNA locus where roX2 binds in trans and displayed low levels of enrichment of the endogenous roX2 locus (consistent with the levels of direct DNA binding observed in the RNase control). Also, individual C-oligos were each successful at specifically enriching the appropriate loci (FIG. 15). Using individual C-oligos led to substantially lower yields, however, demonstrating that the cocktail of three C-oligos acts synergistically (FIG. 15).

Figure 11C:
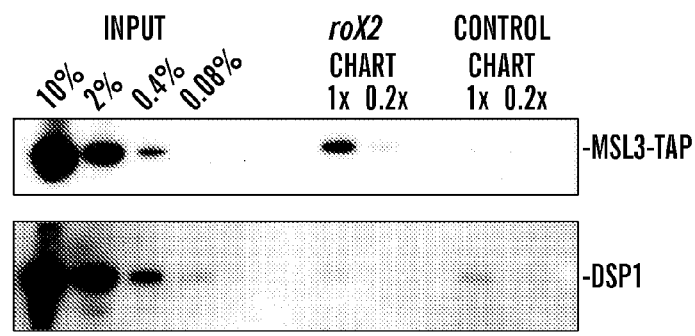

In addition to DNA, the proteins enriched by roX2 CHART were analyzed and found that a subunit of the male-specific lethal complex (MSL3) was enriched relative to a scrambled control by roX2 CHART (FIG. 11C). The yield of MSL3 protein (approximately 1%) was similar to the enrichment observed for the DNA targets and significantly greater than the yield of a negative control protein, DSP1 (yield<0.1%), which was not enriched in the roX2 CHART compared with a scrambled control CHART. It was concluded that enrichment of roX2 by CHART simultaneously enriches protein and DNA representing roX2 targets, and this enrichment is specific.

Extending CHART to a Mammalian RNA

Figure 12A:
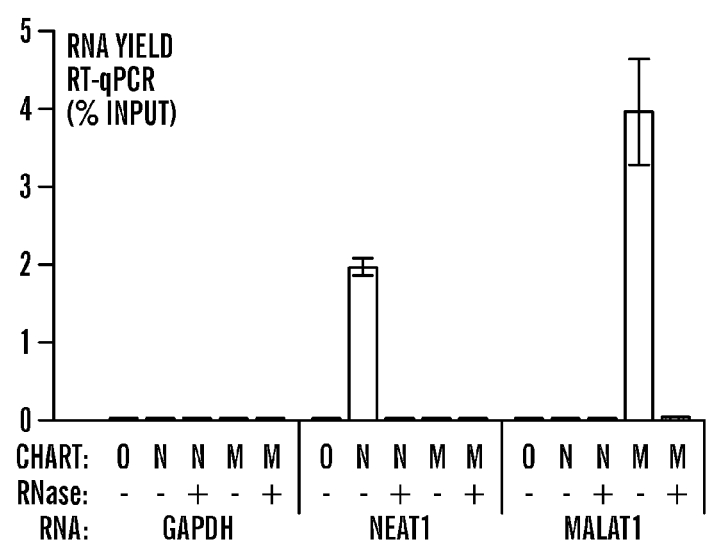
FIG. 12A-FIG. 12C show results from experiments that indicate NEAT1 CHART, but not MALAT1 CHART, specifically enriches NEAT1 RNA along with its protein and DNA targets.
Figure 16A:
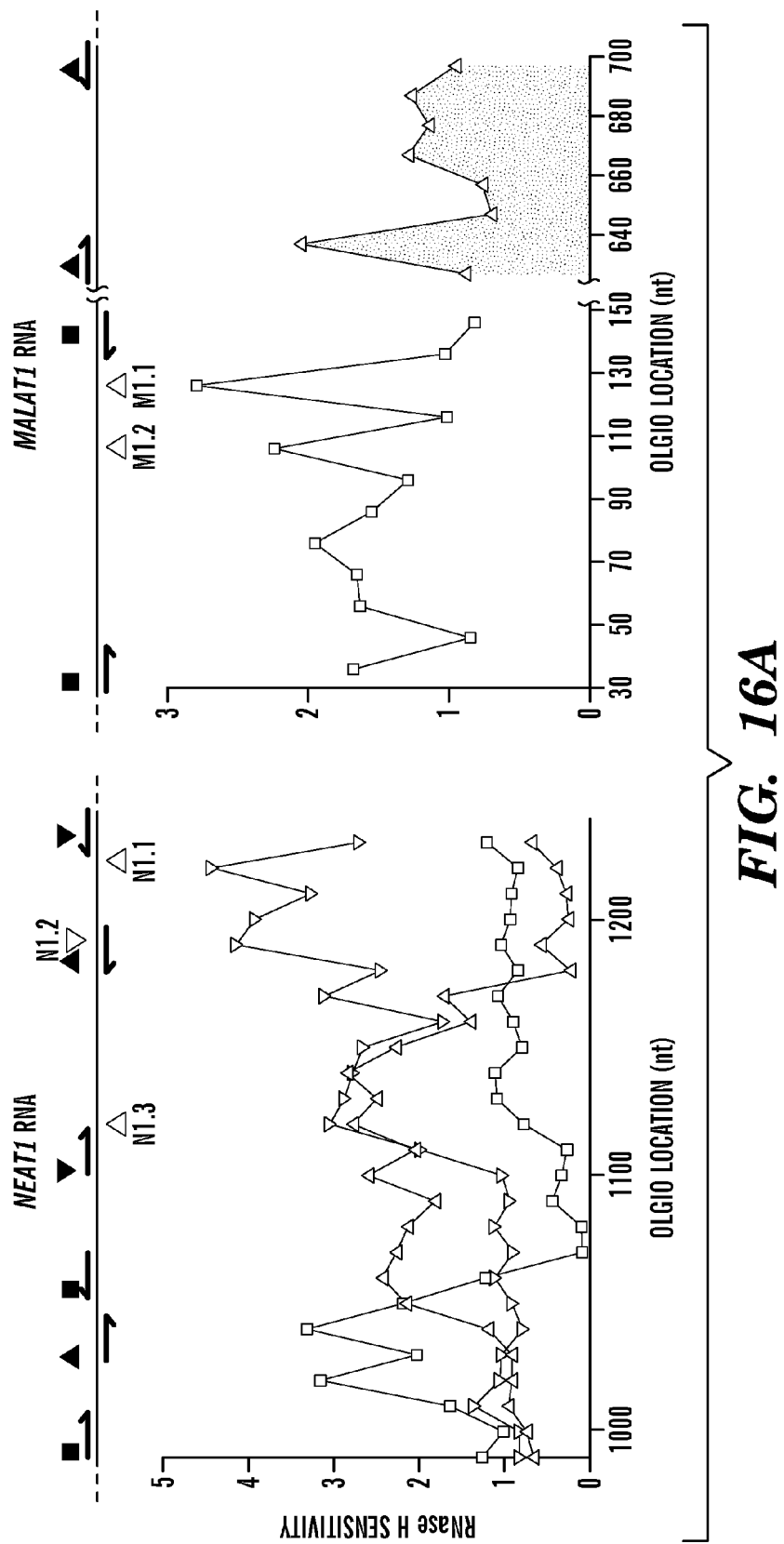
FIG. 16A-FIG. 16C shows experimental design and results.
Figure 16B:
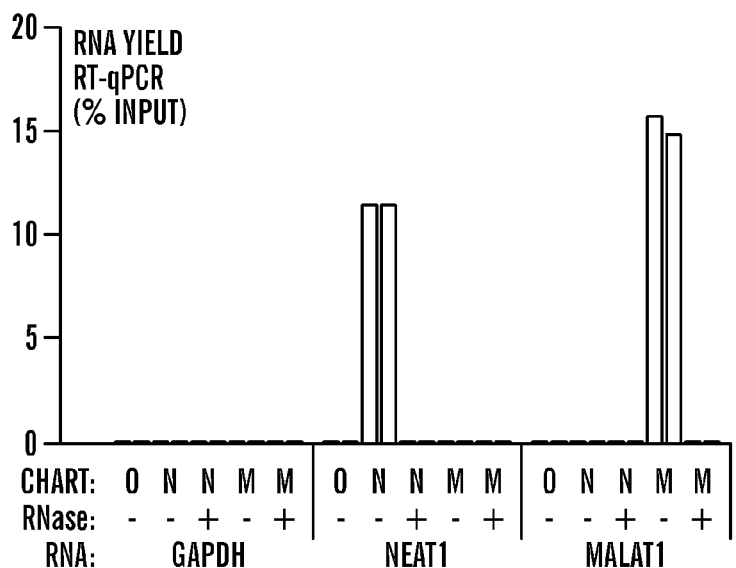

Because roX2 CHART successfully enriched roX2-associated targets, whether these same conditions are general for enrichment of other RNAs was tested, including longer mammalian lncRNAs. CHART was applied to endogenous NEAT1 (3.8 kb), a lncRNA found in human cells, and compared the enrichment to another human lncRNA, MALAT1 (>6.5 kb) in two different cell lines (42-48). Although these lncRNAs are both retained in the nucleus, undergo similar processing, and are encoded next to each other in the genome, they have distinct localizations in the nucleus, NEAT1 localizing to paraspeckles and MALAT1 to nuclear speckles (49, 50). By RNase-H mapping these RNAs from HeLa cells to reveal regions available for hybridization (FIG. 16A) and applying the CHART protocol developed for roX2, it was found that both RNAs could be enriched from cross-linked chromatin extracts derived from two human cell lines (FIG. 12A and FIG. 16B). These RNA yields were lower than observed for roX2, which may be due to differences in vetting of C-oligos (only subregions of these RNAs were mapped by RNase-H), shearing of longer RNAs, or in the complexity or age of the chromatin extract. Regardless of the reason for the modest (approximately threefold) differences in RNA yield, both extracts led to similar CHART enrichment of MALAT1- and NEAT1-associated DNA (discussed below).

Figure 3C:
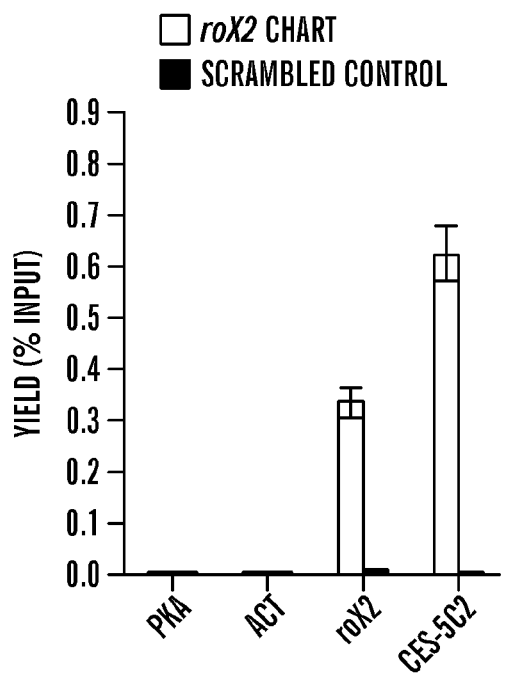
Figure 3D:
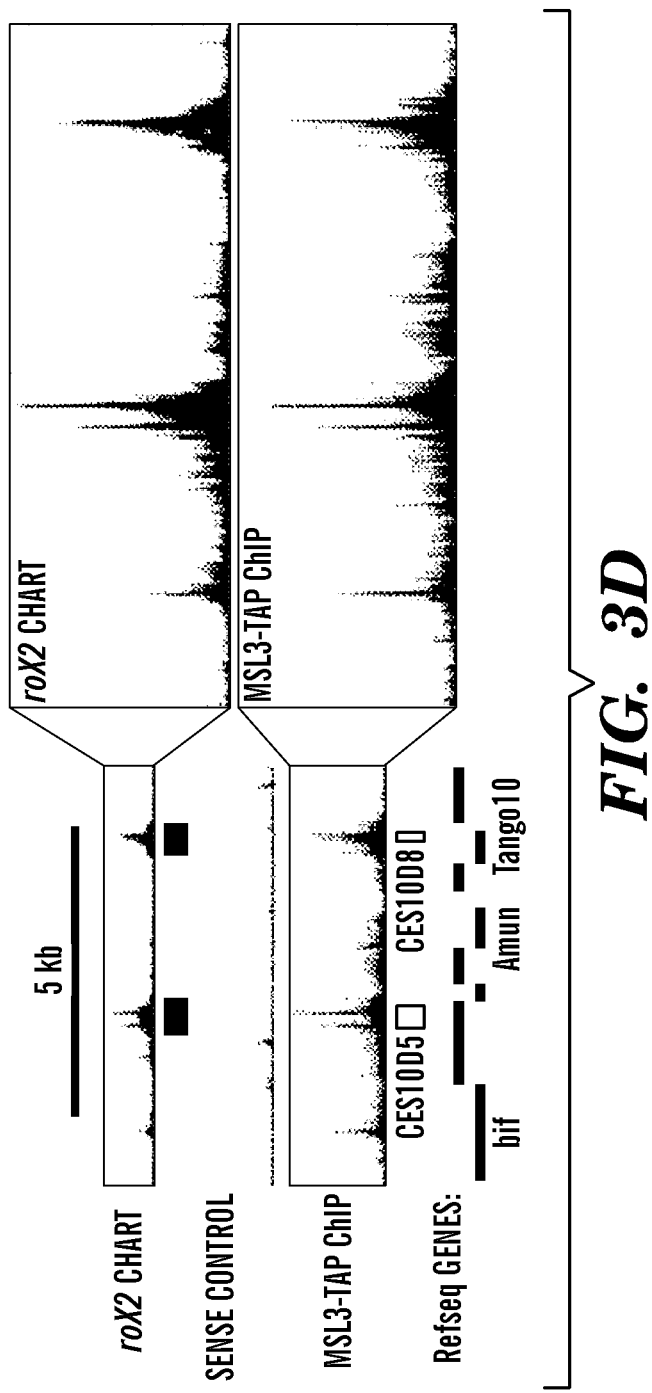
Figure 3E:
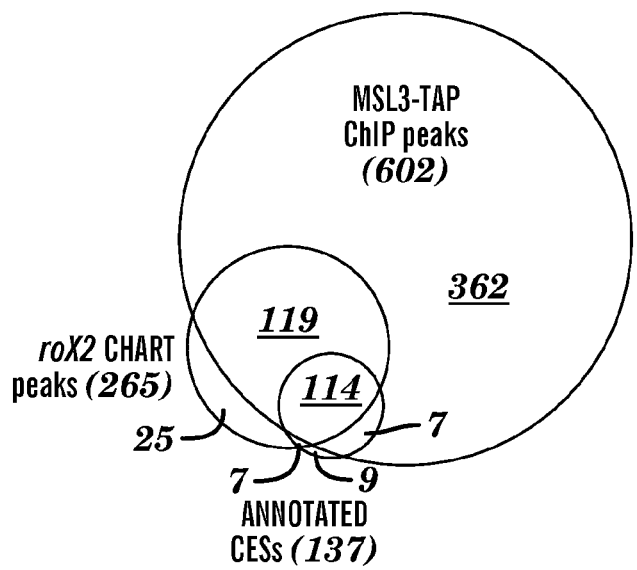
Figure 12B:
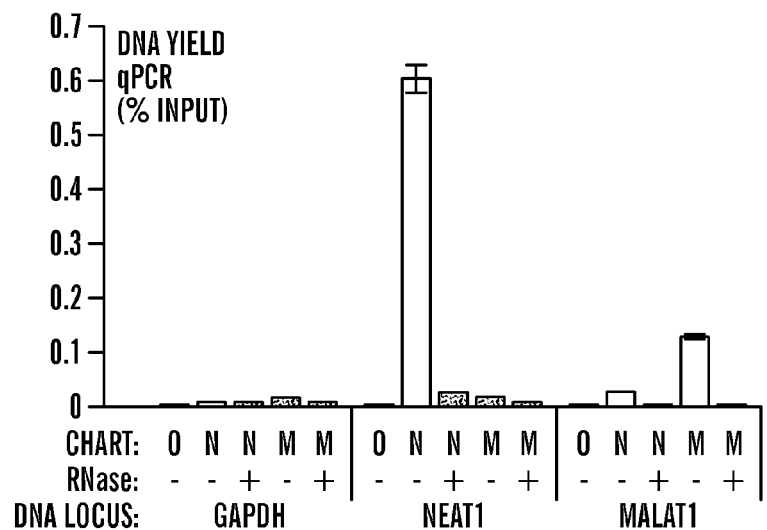
Figure 16C:
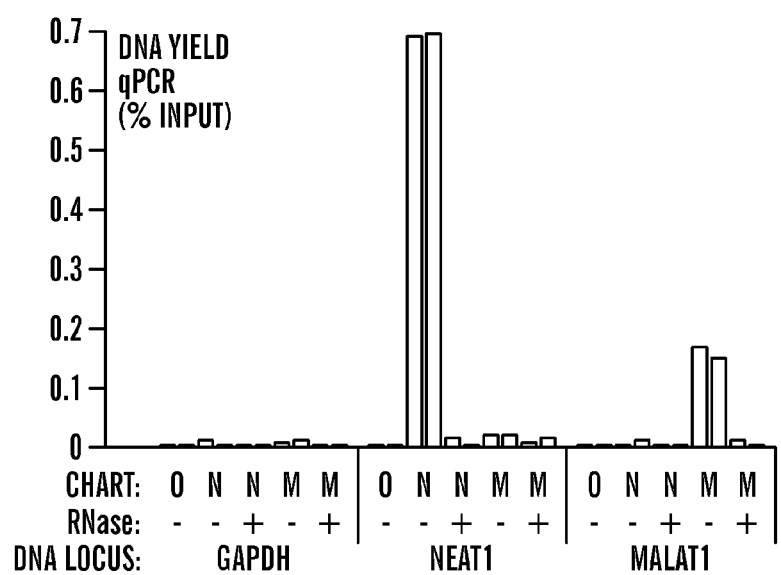

NEAT1 assembles cotranscriptionally with paraspeckle proteins, and fluorescence-imaging experiments suggest that NEAT1 is retained at its endogenous locus (51). Both NEAT1 and MALAT1 CHART demonstrated specific enrichment of their own endogenous genomic loci but not the other's (FIG. 12B and FIG. 16C). Pretreatment of the extract with RNase abrogates the CHART signal (FIG. 12B and FIG. 16C), demonstrating that CHART enrichment is RNA-mediated. In addition to retrieving the endogenous NEAT1 locus, we expected NEAT1 CHART to enrich paraspeckle proteins. Indeed, robust and specific RNA-dependent enrichment of both PSPC1 and p54/nrb (FIG. 3C), two proteins found in paraspeckles that interact with NEAT1 (43, 46, 47) was found. Thus, the analysis of the DNA and proteins enriched by NEAT1 CHART demonstrates that the conditions developed for roX2 CHART also work for a longer endogenous lncRNA from human cells, supporting the generality of CHART.

The observed enrichment of RNAs together with their targets indicate that CHART might be combined with high-throughput sequencing to determine the genome-wide binding profile of an RNA. We tested this conjecture by sequencing the DNA enriched by roX2 CHART to study its genome-wide localization.

Extension of roX2 CHART to Genome-Wide Analysis

The roX2 CHART-enriched DNA was sequenced to generate a genome-wide binding profile for roX2. roX2 is known to localize to the X chromosome (chrX) (52-54), where it acts together with the MSL complex (including protein subunits MSL1, MSL2, MSL3, MLE, and MOF) (9). The MSL complex affects dosage compensation, at least in part, by regulating acetylation of histone H4 lysine 16 (H4K16) in the bodies of active genes (55-60) and influencing transcriptional elongation (61). Therefore strong enrichment of the roX2 CHART-seq signal on chrX was expected, and roX2 was further investigated by examining its distribution in comparison with ChIP results for proteins and modifications associated with dosage compensation.

Figure 17A:
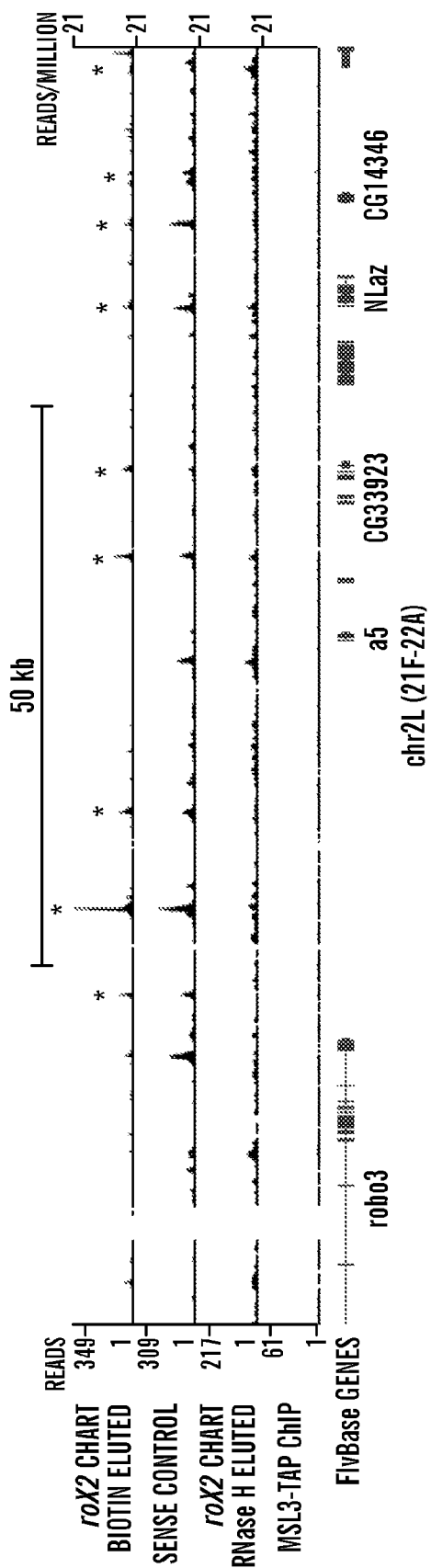
FIG. 17A-FIG. 17D shows data from experiments.
Figure 17B:
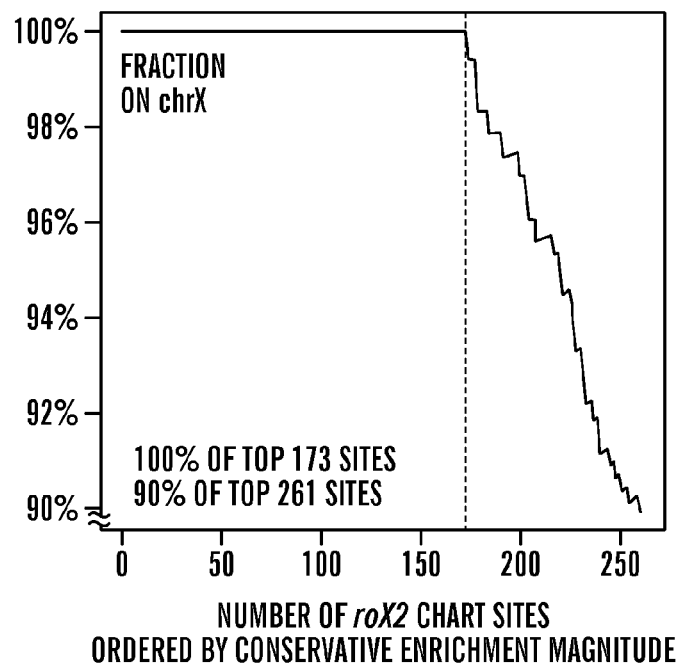

Upon aligning the sequenced reads to the fly genome, the predominant signals from roX2 CHART-seq were a series of intense peaks on chrX (FIG. 13A), consistent with FISH data (52, 53). Some roX2 CHART signals, however, coincide with the peaks in the control sense-oligo profiles (for examples, see FIG. 13A and the autosomal signals in FIG. 17A). These peaks are interpreted as sites where the C-oligos directly enrich DNA. When normalized by the sense-oligo control and ordered by significance, the top 173 roX2 CHART peaks were all found on chrX (FIG. 17B). This strong enrichment of roX2 CHART signals on chrX is consistent with the role of roX2 in dosage compensation.

The enrichment of peaks on chrX was encouraging, but the autosomal signals revealed that CHART eluant contains contaminants from nonspecific hybridization. Many of the artifactual peaks could be filtered by using extra controls and post hoc computational approaches. In this case, setting the appropriate thresholds was viable given the strong expectation of chrX enrichment, but ideally CHART could be performed and interpreted for lncRNAs without such expectations. Minimization of retrieval of these contaminants by increasing the biochemical specificity of CHART, thereby increasing the interpretability of the raw mapped CHART reads, was attempted.

Figure 14E:
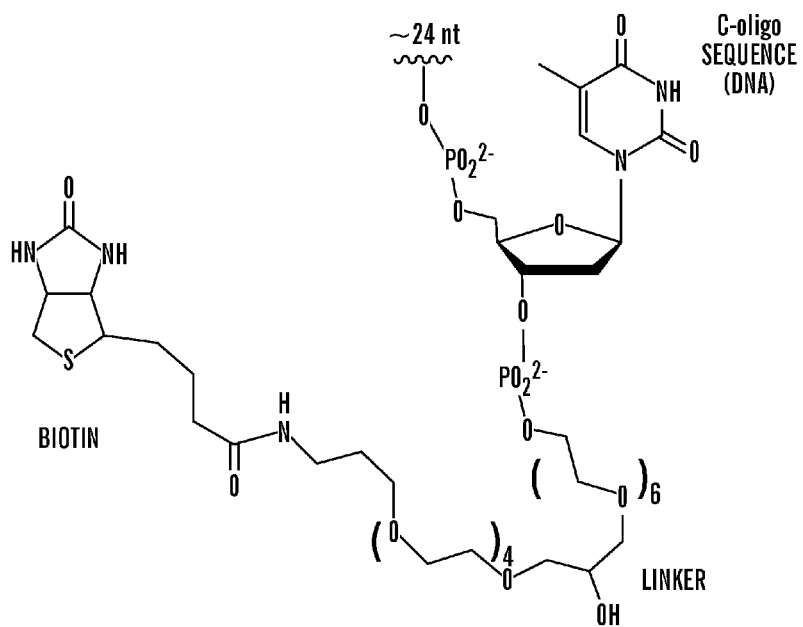
-FIG. 14E shows the development of C-oligos for CHART.
Figure 17C:
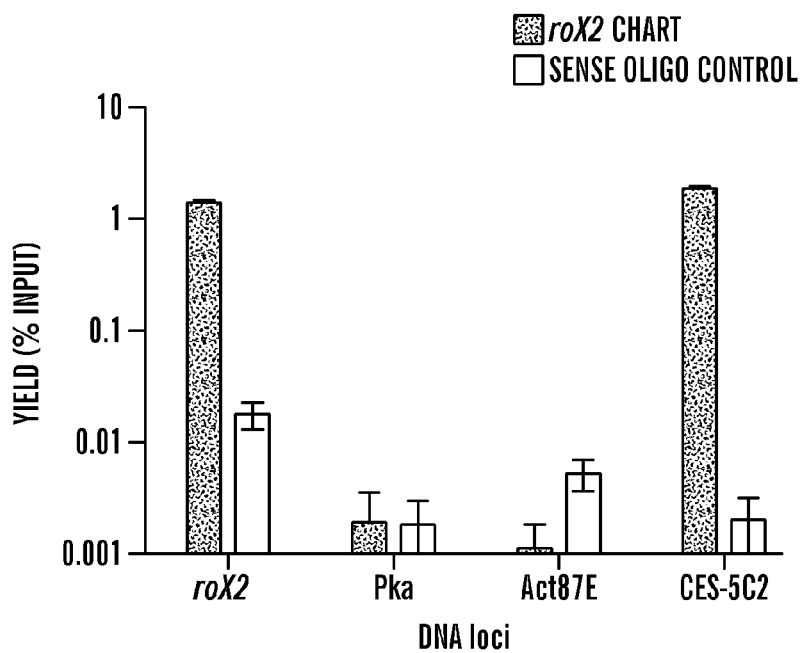

To improve the CHART protocol and minimize purification of products from direct binding of C-oligos to DNA, the heated hybridization step was removed to avoid denaturing the DNA and eluted the roX2 CHART material enzymatically with RNase-H. In this alternative to biotin elution, the DNA bound via roX2 RNA should elute from the resin, but DNA directly bound to the C-oligo should not elute. Because a biotin elution was no longer being used, a biotinylated rather than desthiobiotinylated C-oligos were used (FIG. 14E). These modifications maintained the specific enrichment of the endogenous roX2 locus and CES-5C2 (FIG. 17C), leading to the sequencing of two independent RNase-H-eluted roX2 CHART replicates.

Figure 13A:
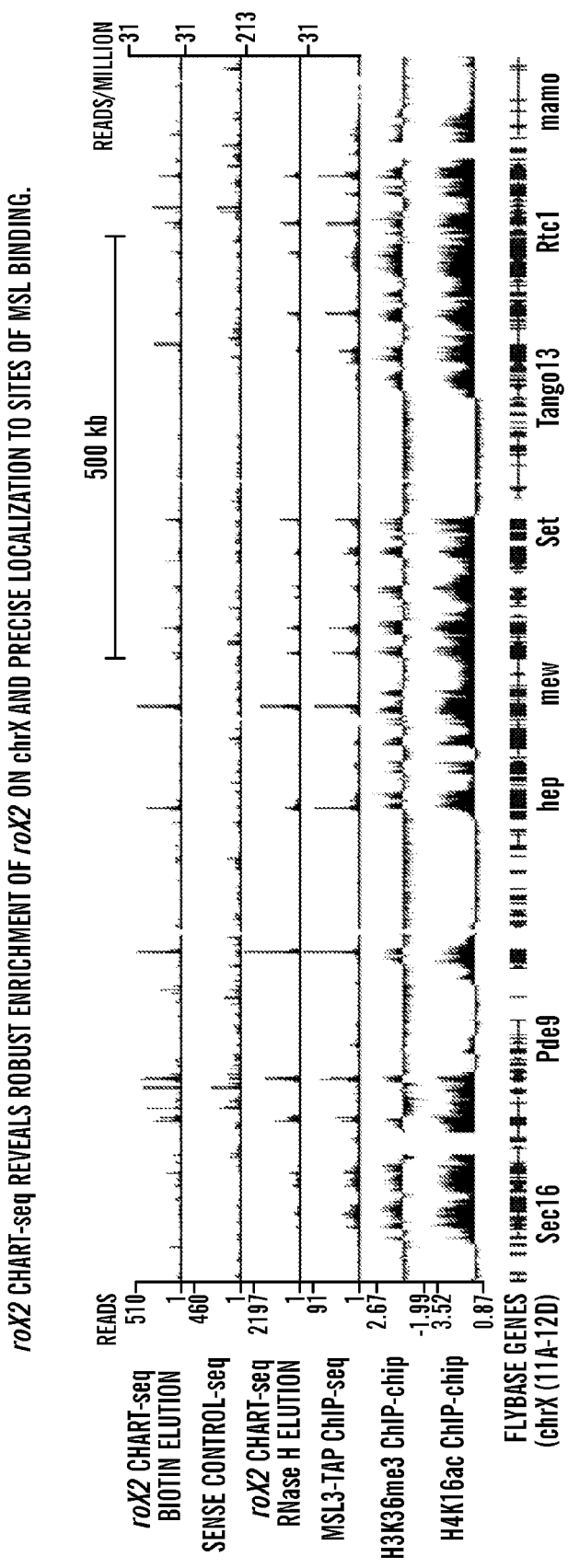
FIG. 13A-FIG. 13D shows results from experiments that indicate roX2 CHART-seq reveals robust enrichment of roX2 on chrX and precise localization to sites of MSL binding.
Figure 17D:
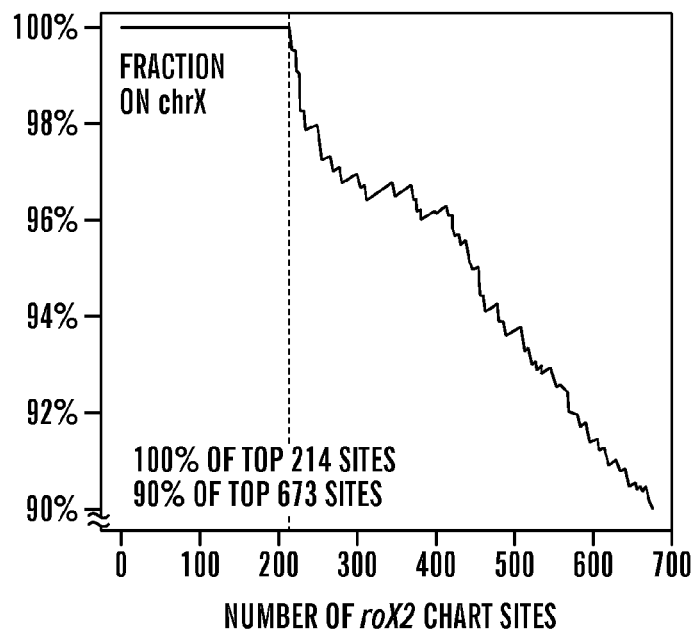

It was immediately evident from the raw, mapped sequencing reads that the RNase-H-eluted CHART samples greatly reduced background from nonspecific hybridization (FIG. 13A). This conclusion is supported by statistical analyses that reveal a decrease in raw autosomal read intensities in comparison to the previous biotin-eluted CHART sample. The two RNase-H-eluted CHART samples showed excellent agreement, and ordering the peaks by input-normalized significance (i.e., without other CHART controls) demonstrated that the top 214 peaks from these data are on chrX (FIG. 17D).

These data demonstrate that roX2 CHART can be combined with sequencing to map the binding sites of a lncRNA, as exemplified by the robust, RNA-mediated enrichment of a series of sites highly enriched on chrX found by roX2 CHART. To further validate the CHART-seq technology and explore the localization of roX2, these data were used to test at molecular resolution whether roX2 localization coincides with specific features of dosage-compensated chromatin, especially sites bound by the MSL complex.

Analysis of roX2 CHART-seq-Enriched Sites

Figure 13B:
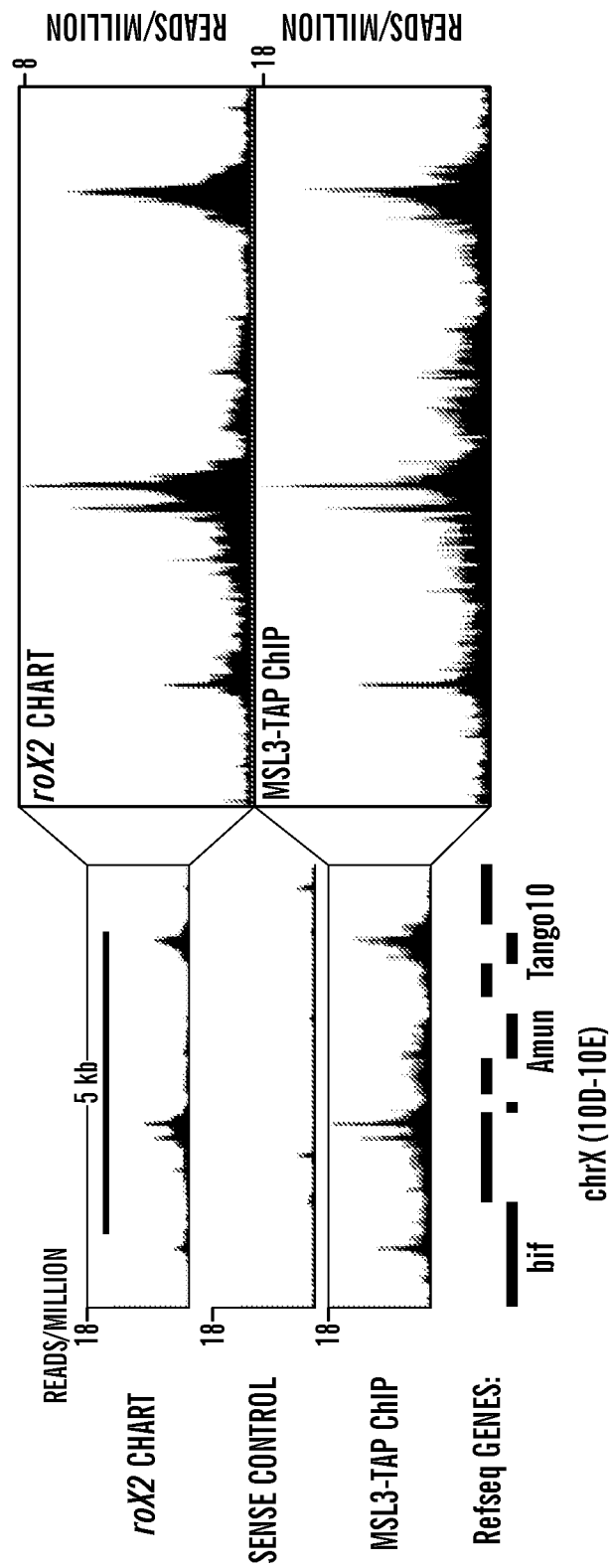
Figure 13C:
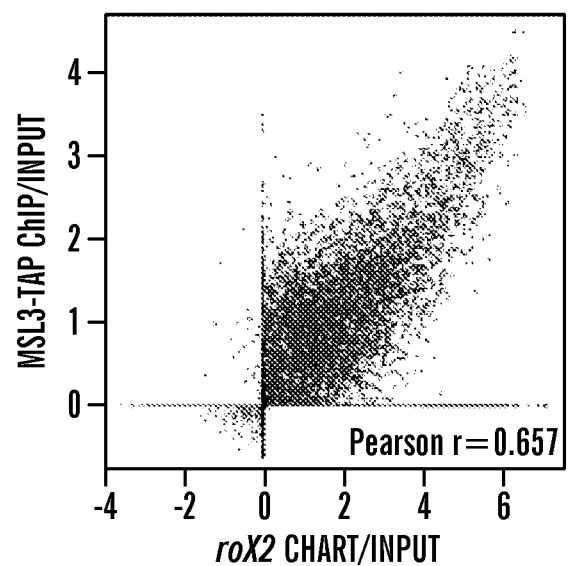
Figure 18A:
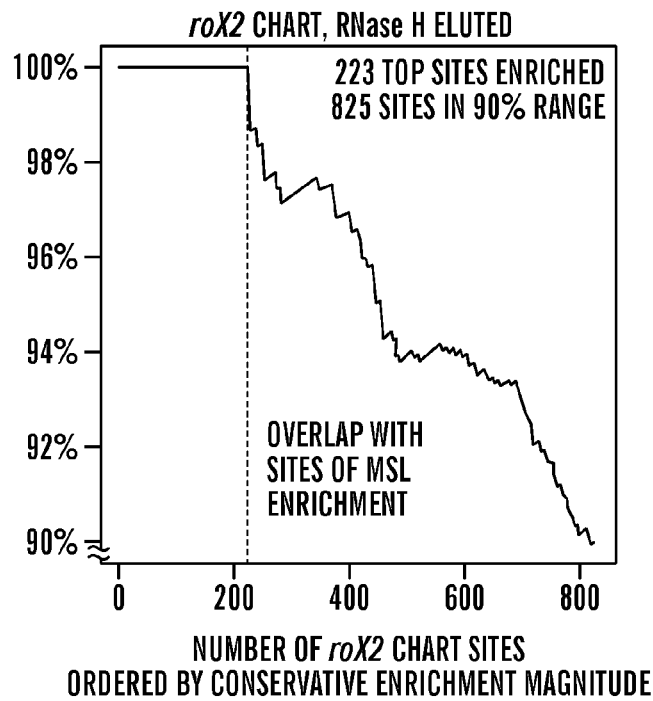
FIG. 18A indicates the top sites of roX2 CHART enrichment are all sites of MSL enrichment. Similar to the analysis in FIG. 13F, roX2 CHART sites were ordered by significance. The plot shows the cumulative fraction of the top peaks that have at least twofold enrichment of MSL3-TAP ChIP (Alekseyenko A A, et al. (2008) Cell 134:599-609). The dashed line represents the cutoff at 223 peaks above which 100% of top peaks are found to have MSL enrichment.
Figure 18B:
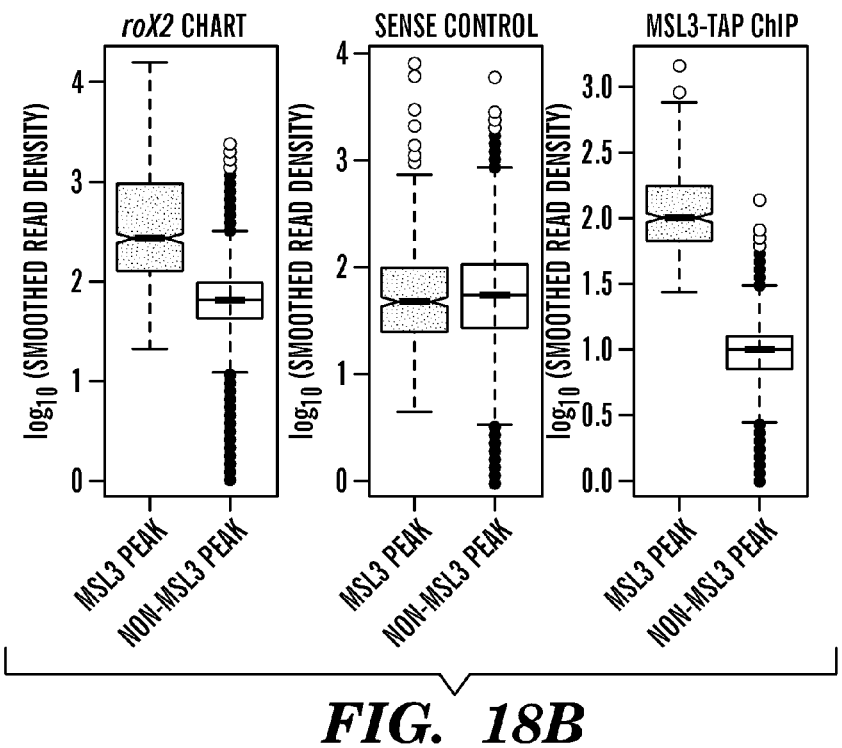
FIG. 18B is a box plot comparing the distribution of read densities for each dataset for either the top MSL3-enriched sites (blue, based on ref. 1; red, 1,000 non-MSL3 enriched sites chosen at random).
Figure 18C:
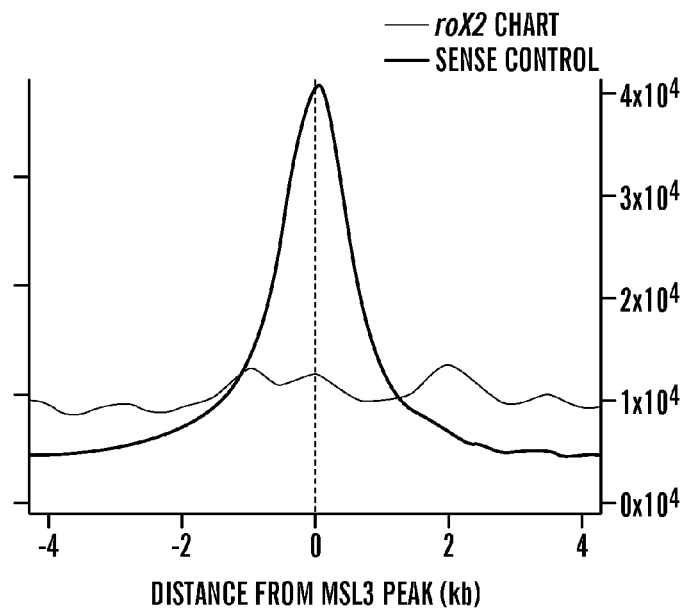
FIG. 18C shows average roX2 CHART data (the line with the highest peak represents the biotin-eluted) and sense-oligo CHART data (the flatter line) aligned around sites of MSL3 enrichment (top 625 peaks used based on FIG. 17B).

The MSL complex is thought to find its binding sites through at least two different mechanisms. Genetic and molecular experiments have revealed a set of 150-300 high-occupancy sites containing a GA-rich sequence motif (41, 62). These sites may act as chromatin entry sites for initial, sequence-specific recognition, followed by spreading to sites on the chrX located in active genes (9). This second class of sites is thought to be recognized through general marks of active transcription, such as H3K36me3, because active autosomal genes can acquire MSL binding when inserted on X (63). Genome-wide CHART of roX2 allowed us to test whether roX2 RNA has the same preference for chromatin entry sites as the MSL complex. When compared to ChIP-chip or ChIP-seq for chromatin modifications associated with dosage compensation (H4K16ac and H3K36me3) or with the ChIP signal observed for a tagged version of MSL3, the roX2 CHART signal was notable for its coincidence with MSL high-occupancy sites (FIGS. 13 A and B). The lower significance autosomal signals did not line up with previously proposed MSL binding sites (62) and were not enriched for MSL binding, which suggests they are unlikely to be real roX2 binding sites. Statistical analyses demonstrated that the top roX2 CHART peaks are all enriched for MSL binding (FIG. 18A), and known MSL binding sites have a higher roX2 CHART signal than non-MSL-binding sites (FIG. 18B). Not only does the roX2 CHART signal overlap with the MSL-ChIP signal, but also the datasets correlate (FIG. 4C) and the intense peaks align precisely (FIG. 18C). Inspection of the data also reveals that the CHART signal typically mirrors the contours of the MSL3-ChIP signal (FIG. 13B). These data are consistent with roX2 acting as an integral subunit of the MSL complex while the complex is bound to chromatin.

Figure 13D:
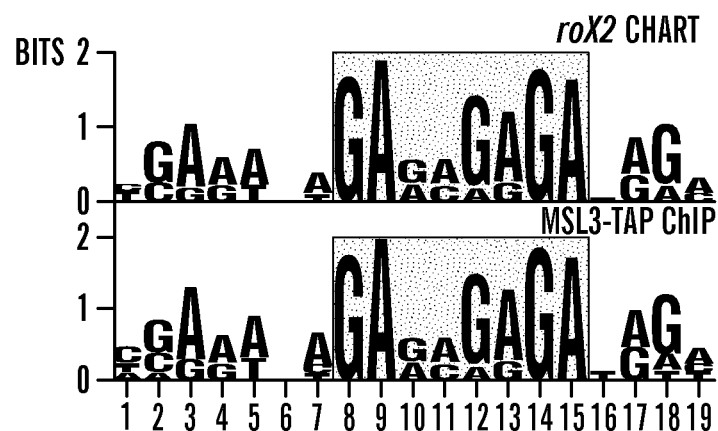

If roX2 is binding to the same spectrum of chromatin entry sites as MSL3, one prediction is that the locations of roX2 CHART peaks can be used to find a DNA motif associated with roX2 binding, and this motif should be similar to the motif previously derived for sites of MSL3 binding. Indeed, motif analysis of the CHART data for roX2 yields a nearly identical motif to that derived from the ChIP analysis of MSL3 (FIG. 13D). This sequence can attract local MSL activity when inserted onto an autosome (41). In sum, these data demonstrate that CHART allows the determination of the genome-wide binding sites of a ncRNA.

Discussion

Although recent advances have demonstrated the importance of lncRNAs as regulatory factors and revealed that many of these lncRNAs can act in concert with chromatin-modifying machinery, our understanding of where these lncRNAs directly act on chromatin has progressed more slowly. CHART was developed and use to examine the genomic binding sites of a 1ncRNA. Because this approach is analogous to ChIP, a comparison of these techniques is presented. Depending on the antibody, useful ChIP enrichments range from a fewfold to up to 3 orders of magnitude for the best antisera. roX2 CHART achieves enrichments on the high end of this range, at times exceeding 3 orders of magnitude (FIG. 11B). In theory, the resolution of CHART-seq could have proven significantly worse than ChIP-seq because CHART requires a higher degree of cross-linking. In practice, any loss of resolution observed for CHART-seq is minor as can be seen by comparing MSL3-TAP (where TAP is a tandem affinity purification epitope tag) ChIP-seq signals to roX2 CHART-seq signals (FIGS. 13A and B). Therefore CHART appears similar to ChIP in enrichment and resolution.

The limitations of CHART also overlap with those of ChIP. Neither provides information regarding the stoichiometry of binding at each genomic locus-only enrichment values. Also like ChIP, there is no guarantee that different target loci will be enriched with equal efficiency, because at some loci the C-oligos may have less access (e.g., if they are occluded from binding, similar to epitope masking with ChIP). Given the utility and importance of ChIP despite these caveats, it is reasonable to expect similar utility from CHART. Importantly, both ChIP and CHART provide information about the localization of the factor to chromatin loci but do not reveal the molecular basis of the interaction; CHART-enriched targets could either be directly bound to the RNA or bound through other factors such as bridging proteins or RNAs. No evidence that roX2 binding sites are enriched for sequences with Watson-Crick complementarily to roX2 was found (Table 2), which suggests that the interactions between roX2 and these loci are indirect, very short, or based on non-Watson-Crick interactions.

Also similar to ChIP, CHART-enriched material can be used to examine either candidate genomic loci or genome-wide binding profiles. Both were applied to roX2 and roX2 was found localized to dosage-compensated regions on chrX, as expected. Comparison of the high-resolution map from roX2 CHART with published data for the MSL complex achieved by using ChIP revealed that roX2 binds at the same sites in chromatin as the MSL complex. Because many lncRNAs are thought to act together with chromatin-modifying machinery, this comparison allowed validation of the previously untested inference that a lncRNA can act at the same sites on chromatin across the genome as its associated chromatin-modifying complex.

CHART was used successfully for a longer mammalian ncRNA from two different cell lines (FIG. 12 and FIG. 16). Few lncRNAs are known to bind to specific genomic sites, but RNAs can be retained near their endogenous loci, serving as a positive control for CHART enrichment without previous knowledge of trans-acting sites. It was found that CHART analysis of endogenous loci can be complicated by the direct DNA binding of the C-oligos, but using RNase-pretreated extract allows this artifactual signal to be distinguished from the desired RNA-mediated CHART signal. Analysis of the RNAs examined here shows that CHART may be successfully applied to RNAs of different lengths and origin.

Despite the successful mapping of genomic binding sites using roX2 CHART-enriched samples, it is not yet clear how roX2 compares to other chromatin-bound lncRNAs in binding mode and stoichiometry, and therefore the generality of CHART will be determined as it is applied to more RNAs. Although the strength of roX2 CHART signals allows them to be easily distinguished from nonspecific background, the use of oligonucleotides as affinity reagents will always raise the potential of direct or indirect off-target hybridization. From analysis of the autosomal biotin-eluted roX2 CHART peaks, particular caution was found to be required when interpreting sharp peaks (<600 bp) and peaks that contain motifs with homology to the target RNA; this pattern is indicative of likely artifacts and therefore requires further experimentation. In the case of roX2 CHART, the CHART-identified binding sites were not found to have homology to the RNA, which demonstrates that these potential artifacts were avoided.

Figure 12C:
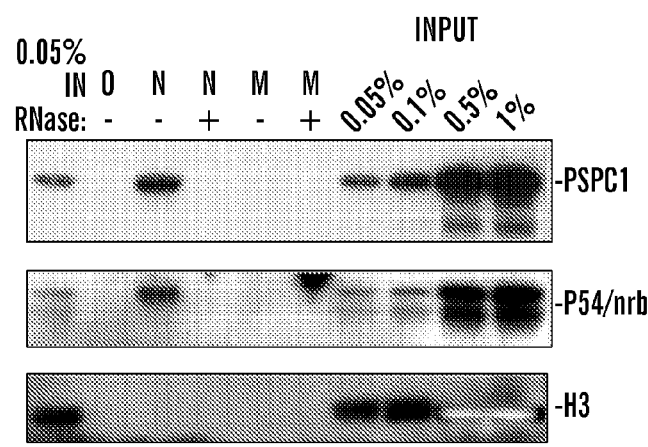

In addition to locating the genomic targets of an RNA, CHART can also be used to examine other RNA associated factors; we have demonstrated this point by analyzing CHART-enriched material by Western blot for protein targets (FIGS. 11C and 12C). Because CHART involves reversible cross-linking, the enriched material can be used for the reciprocal of an RNA-IP; instead of pulling down protein and looking for RNA, CHART allows enrichment of the RNA and examination of which proteins copurify by Western blot. Therefore, although this work focused on the use of CHART to examine DNA targets, CHART-enriched material can also be analyzed for other factors, and the extension of CHART to proteomic analyses is also expected to uncover RNA-associated proteins.

In summary, the development of CHART, a technique that allows determination of RNA targets, is reported herein. CHART was successfully applied to lncRNAs of different lengths from two different organisms. CHART was able to be extended to robust genome-wide analysis and from this analysis the previously untested inference that a 1ncRNA can act across the genome at the same sites as an associated chromatin-modifying complex was addressed. Given the intense interest in the functionality of lncRNAs, including their roles regulating chromatin structure and gene expression, CHART provides a valuable tool to identify the genomic loci directly regulated by an RNA, as exemplified here with roX2.

Materials and Methods

To accomplish CHART enrichment, extract (250 µL, 8×10⁷ cell equivalent) was adjusted to hybridization conditions (20 mM Hepes pH 7.5, 817 mM NaCl, 1.9 M urea, 0.4% SDS, 5.7 mM EDTA, 0.3 mM EGTA, 0.03% sodium deoxycholate, 5×Denhardt's solution) and precleared with ultralink-streptavidin resin (Pierce). C-oligos (800 nM each R2.1-3) were added and hybridized (55° C. for 20 min; 37° C. for 10 min; 45° C. for 60 min; 37° C. for 30 min). The bound material was captured by using streptavidin beads [(MyOne C1; Invitrogen, overnight, room temperature (RT)], rinsed five times with WB250 (250 mM NaCl, 10 mM Hepes pH 7.5, 2 mM EDTA, 1 mM EGTA, 0.2% SDS, 0.1% N-lauroylsarcosine), and eluted with 12.5 mM biotin in WB250 for 1 h at RT. For RNase-pretreated extract, RNase (Roche, DNase-free, 1 µL) was added to the initial extract and allowed to incubate for 10 min at RT prior to adjusting to hybridization conditions. RNase-H-eluted CHART was performed similarly, except we omitted the prebinding to ultralink-streptavidin resin and used higher concentrations C-oligos (1.3 µM each). For the RNase-H elution, the final rinse was with RNase-H rinse buffer (50 mM Hepes pH 7.5, 75 mM NaCl, 3 mM MgCl2, 0.125% N-lauroylsarcosine, 0.025% sodium deoxycholate, 20 u/mL SUPERasIN, 5 mM DTT). The CHART-enriched material was then resuspended in RNase-H rinse buffer (100 µL) and RNase H (10 U) was added. The elution was allowed to proceed for 10 min with gentle shaking at RT. The beads were captured and the reaction stopped with EDTA before proceeding to analyze the CHART-enriched proteins or nucleic acids.

To test whether roX2 CHART targets show prevalence of sequences complementary to roX2 RNA we have extracted all nmers from roX2 RNA and compared the number of direct and reverse-complement occurrences between a set of roX2 CHART target regions and a set of randomly selected control regions. Each cell in the table shows the average number of n-mer matches for roX2 CHART targets, followed by the average number of matches observed in control sequences (separated by /). Around each roX2 CHART target site, 300-bp regions were analyzed. A tenfold set of control regions was chosen randomly from the X chromosome. The results suggest that the roX2 CHART target regions do not show increased frequency of nmers complementary to either full roX2 RNA product (first row) or the 72-nt step loop (second row) critical for the roX2 function (Park S W, et al. (2007) Genetics 177:1429-1437). In fact the overall match frequency appears to be slightly below that of randomly selected controls. Comparison with control regions selected from entire genome yields analogous results.

Preparation of Cross-linked Nuclei. Drosophila S2 cells expressing male-specific lethal complex (MSL3-TAP, where TAP is a tandem affinity purification epitope tag) (Alekseyenko et al. (2006) Genes Dev 20:848-857) were grown in shaker flasks in serum-free CCM3 media (HyClone). Cells (approximately 10¹⁰ cells) were harvested by centrifugation (500×g, 15 min, 4° C.), rinsed once with PBS, resuspended to 200 mL with PBS, and cross-linked [1% formaldehyde, 10 min, room temperature (RT)], rinsed three times with PBS, and stored at −80° C. or carried forward directly to prepare nuclei. Nuclei were enriched essentially as described (Dennis J H, et al. (2007) Genome Res 17:928-939). Briefly, cells (approximately 10⁹ cells) were washed with PBS and nuclei were enriched by disrupting cells with a Dounce homogenizer in sucrose buffer (0.3 M sucrose, 1% Triton X-100, 10 mM Hepes pH 7.5, 15 mM KOAc, 0.1 mM EGTA, 0.5 mM spermidine, 0.15 mM spermine, 1× Roche protease inhibitor tablet, 1 mM DTT, 10 u/mL SUPERasIN), diluted with an equal volume of glycerol buffer (25% glycerol, 10 mM Hepes pH 7.5, 100 mM KOAc, 1 mM EDTA, 0.1 mM EGTA, 0.5 mM spermidine, 0.15 mM spermine, 1× Roche protease inhibitor tablet, 1 mM DTT, 10 u/mL SUPERasIN), and layered on top of glycerol buffer (4 mL). The crosslinked nuclei were collected by centrifugation (1;000×g, 15 min, 4° C.). This protocol was also used to prepare cross-linked nuclei from HeLa cells, except by using tenfold fewer cells for the same volumes (i.e., preparing 10⁸ nuclei).

Chromatin Extract for RNase-H Mapping. Chromatin extract for RNase-H mapping was prepared by rinsing nuclei with shearing buffer (50 mM Hepes pH 7.5, 75 mM NaCl, 0.1 mM EGTA, 0.5% N-lauroylsarcosine, 0.1% sodium deoxycholate, 20 u/mL SUPERasIN, 5 mM DTT) and resuspending into 4 mL buffer/10⁹ nuclei for S2 cells or 4 mL buffer/10⁸ HeLa nuclei. This material was sheered using a Covaris S2 instrument (30-min program, 10% duty cycle, intensity of 5, 4° C.) and then cleared by centrifugation (16; 100×g, 10 min, RT). The cleared extract was divided into aliquots, flash frozen with N2, and stored at −80° C. or used directly for RNase-H mapping reactions.

RNase-H Mapping. Cross-linked extract was divided into individual 10 µL reactions supplemented with MgCl2 (3 mM final), DTT (10 mM final), SUPERasIN (10 u), and RNase H (5 U). To each reaction a different oligonucleotide (100 pmol) was added and the reaction was allowed to proceed for 30 min at 30° C. The DNA was hydrolyzed by adding RQ1 DNase (1 µL, Promega) and CaCl2 (500 µM final) and incubating for an additional 10 min at 30° C. The reaction was stopped by adding quenching buffer (2 µL of 125 mM EDTA, 250 mM Tris•HCl pH 7.2, 0.5 mg/mL Proteinase K, 5% SDS), incubated for 1 h at 55° C., and then 30 min at 65° C. RNA was recovered using a PureLink RNA purification kit (Invitrogen) and analyzed by qPCR for Rnase H sensitivity.

$$RNase\text{-}H \text{ sensitivity} = \left( \frac{\text{efficiency}_{TARGET\ PRIMERS}^{C_{T,olgio}-C_{T,no\ oligo}}}{\text{efficiency}_{CONTROL\ PRIMERS}^{C_{T,olgio}-C_{T,no\ oligo}}} \right).$$

Capture Oligonucleotides. Peaks from RNase-H mapping were identified and used to design 24-25 nt C-oligos using BLAST to avoid complementarity to other RNA sequences. The resulting C-oligos were synthesized on an Expidite DNA synthesizer with 3'-desthiobiotin (DSB-TEG) and four oligoethyleneglycol spacers. The oligonucleotides were synthesized 4,4'-dimethoxytrityl-on for purification using Poly-Pak II cartridges (Glen Research). C-oligos used for RNase-H-eluted capture hybridization analysis of RNA targets (CHART) were 3'-modified by a single oligoethyleneglycol spacer and biotin-TEG.

Preparation of Chromatin Extract for CHART. Rinsed, cross-linked nuclei were further cross-linked with formaldehyde (10⁹ S2 nuclei in 50 mL of PBS supplemented with 3% formaldehyde, 30 min, RT). The nuclei were rinsed with PBS and then resuspended in WB100 (100 mM NaCl, 10 mM Hepes pH 7.5, 2 mM EDTA, 1 mM EGTA, 0.2% SDS, 0.1% N-lauroylsarcosine). This material was sheared using a Bransen sonicator to 2-3 kb average DNA fragment sizes and then cleared by centrifugation (16; 100×g, 10 min, RT). The cleared extract was divided into aliquots, flash frozen with N2, and stored at −80° C., or used directly for CHART. HeLa and MCF7 (a breast adenocarcinoma cell line) extracts were made following the same protocol, except using 108 nuclei and shearing with a Covaris S2 instrument (15-min program, 10% duty cycle, intensity of 5, 4° C.).

Nucleic Acid Analysis. CHART-enriched samples were deproteinized with proteinase K and cross-links were reversed with Proteinase K (1 mg/mL), SDS (0.5%), and Tris pH 7.4 (100 mM) at 55° C. for 1 h and then 65° C. for 30 min.

qPCR Analysis. Nucleic acids were purified with QIAGEN columns according to the manufacturer's directions. CHART-enriched material was assayed in comparison with supernatant from a nooligo control (to control for handling loss, hereafter referred to as input). The yields are reported relative to input signal without further normalization:

$$\text{Yield} = \left( \frac{\text{Input dilution factor}}{\text{efficiency}_{PRIMERS}^{C_{T,CHART}-C_{T,INPUT}}} \right)$$

In cases where the CT was not reached within 40 cycles, a value of 40 was assigned for purposes of analysis, thereby conservatively underestimating enrichment.

Protein Analysis. CHART samples were treated with SDS (1.0%), Tris pH 8.8 (100 mM), and β-mercaptoethanol (1 M) for 1 h at 95° C. These samples were resolved by SDS PAGE, transferred to PVDF, and analyzed using peroxidase antiperoxidase (to detect MSL3-TAP, Sigma), anti-DSP1 antisera (Mosrin-Huaman et al., (1998) Dev Genet. 23:324-334), anti-PSPC1 antisera (sc-84577), anti-p54/nrb (sc-67016), or anti-histone H3 (ab1791).

Sequence Analysis. DNA fragments were isolated, further sheared (Lieberman-Aiden E, et al. (2009) Science 326:289-293), sequenced (Illumina GAIIx or HiSeq) and mapped to the Drosophila genome (dm3, Bowtie aligner, Langmead et al., (2009) Genome Biol 10:R25), recording positions of uniquely mappable reads. The enrichment of the biotin-CHART signal was determined relative to the sense-oligo controls and the RNase-H-eluted CHARTsignal was determined relative to input. Conservative enrichment profiles were determined using the SPP (Solexa Processing Pipeline) package (Kharchenko et al., (2008) Nat Biotechnol 26:1351-1359) (lower bound of enrichment was determined based on a Poisson model, with a confidence interval of p=0.001). Positions of top CHART sites were determined as peaks of the conservative enrichment profiles (with minimum separation of 3 kb). The top peaks were selected for subsequent analysis based on 90% specificity to chrX (FIGS. 17B and F). To determine sequence motifs corresponding to the top CHART peaks (FIG. 13D), 200-bp sequences flanking the peaks were analyzed using MEME (Multiple EM for Motif Elicitation) (Bailey et al., (2006) Nucleic Acids Res 34:W369-373).

TABLE 2

Watson-Crick complementarity between roX2 RNA and genomic sequence of roX2 CHART targets

|  | 5-mers | 7-mers | 10-mers |
| --- | --- | --- | --- |
| Full roX2-RA | 190.0/196.9 | 30.3/34.4 | 0.48/0.87 |
| roX2-RA 72nt loop | 38.8/43.1 | 4.21/4.90 | 0.169/0.160 |

TABLE 3

Capture oligonucleotides used in this study

| | |
| --- | --- |
| R2.1: | TAA CAC CAA TTT ACC CTT TCG ATG LLL L-DSB (SEQ ID NO: 1) |
| R2.2: | TCT CAC TGT CCG TAA GAC AAT TCA ALL LL-DSB (SEQ ID NO: 2) |
| R2.3: | CTC TTG CTT GAT TTT GCT TCG GAG ALL LL-DSB (SEQ ID NO: 3) |
| CNTL: | TAA TGG CTC CTA CAT ACT ACA TCT LLL L-DSB (SEQ ID NO: 4) |
| R2.AS1: | CAT CGA AAG GGT AAA TTG GTG TTA LLL L-DSB (SEQ ID NO: 5) |
| R2.AS2: | TTG AAT TGT CTT ACG GAC AGT GAG ALL LL-DSB (SEQ ID NO: 6) |
| R2.AS3: | TCT CCG AAG CAA AAT CAA GCA AGA GLL LL-DSB (SEQ ID NO: 7) |
| N1.1: | GCT AGG ACT CAC ACT GGC CAG GGA CLL LL-DSB (SEQ ID NO: 8) |
| N1.2: | TCC ATG TCT CCC GGT TCC ATC TGC TLL LL-DSB (SEQ ID NO: 9) |
| N1.3: | CAT GAA GCA TTT TTG TAA CTT TCA GLL LL-DSB (SEQ ID NO: 10) |
| M1.1: | GGA CTC TGG GAA ACC TGG GCT CCC GLL LL-DSB (SEQ ID NO: 11) |
| M1.2: | GAG GCG TCA GAG GGG ACC TGC CTT CLL LL-DSB (SEQ ID NO: 12) |

TABLE 4

Primer sequences used in this study (All sequences are listed 5' to 3')

RNASE H MAPPING

| | |
| --- | --- |
| R2.GREEN.F | AGCTCGGATGGCCATCGA (SEQ ID NO: 14) |
| R2.GREEN.R | CGTTACTCTTGCTTGATTTTGC (SEQ ID NO: 15) |

TABLE 4-continued

Primer sequences used in this study (All sequences are listed 5' to 3')

| | |
|---|---|
| R2.BLUE.F | CATTGATAATCGTTCGAAACGTTC (SEQ ID NO: 16) |
| R2.BLUE.R | GACAAGCGCGTCAACC (SEQ ID NO: 17) |
| R2.RED.F | TGTCTTGGAACGCAACATT (SEQ ID NO: 18) |
| R2.RED.R | GCATATATATTTGCTTAATTTGCAACAT (SEQ ID NO: 19) |
| N1.RED.F | GTGGGCCTGCAGCCATCCAG (SEQ ID NO: 20) |
| N1.RED.R | GCGGGCTCTCTCCTCCAGGG (SEQ ID NO: 21) |
| N1.YELLOW.F | GGGGCGGATCGGTGTTGCTT (SEQ ID NO: 22) |
| N1.YELLOW.R | CCCGGTTCCATCTGCTCGCC (SEQ ID NO: 23) |
| N1.BLUE.F | AGCCCGGGACAGTAAGCCGA (SEQ ID NO: 24) |
| N1.BLUE.R | TCCCCACCCTCTCTGCAGGC (SEQ ID NO: 25) |

QPCR/RT-QPCR

| | |
|---|---|
| ACT5C.F | CAGCTCCTCGTTGGAGAAGT (SEQ ID NO: 26) |
| ACT5C.R | AAGCCTCCATTCCCAAGAAC (SEQ ID NO: 27) |
| CES-11B16.F | TCGCCGAACCCCAACACCAA (SEQ ID NO: 28) |
| CES-11B16.R | GCGCGGTGTTCATCGGCCAT (SEQ ID NO: 29) |
| CES-3A1.F | GTTGGCGGAGTGCTTGCCCT (SEQ ID NO: 30) |
| CES-3A1.R | CGGACGCAGAAGTCCTCGCC (SEQ ID NO: 31) |
| CES-3F3.F | CCGCTTGCGATGCAAACGCC (SEQ ID NO: 32) |
| CES-3F3.R | ATGTGGCGGTACGCGGATGC (SEQ ID NO: 33) |
| CES-5C2.F | AGAGCGAGATAGTTGGAAG (SEQ ID NO: 34) |
| CES-5C2.R | TCAAGTTGAGATCGCTTCG (SEQ ID NO: 35) |
| CG14438.F | GACCGGATTACTGGGTTTCGC (SEQ ID NO: 36) |
| CG14438.R | CATATGGCCGATCAAGTGCTC (SEQ ID NO: 37) |
| PEAK-5A1.F | AACGGCGTAGTGGGAGGCCA (SEQ ID NO: 38) |
| PEAK-5A1.R | CCGCCCACCACAGCTGTCTG (SEQ ID NO: 39) |
| PKA.F | CAATCAGCAGATTCTCCGGCT (SEQ ID NO: 40) |
| PKA.R | AGCCGCACTCGCGCTTCTAC (SEQ ID NO: 41) |
| ROX2.F | AGCTCGGATGGCCATCGA (SEQ ID NO: 42) |
| ROX2.R | CGTTACTCTTGCTTGATTTTGC (SEQ ID NO: 43) |
| RPL17.F | TCAGTAGTTGTCACCGGCTTG (SEQ ID NO: 44) |
| RPL17.R | CCCGCCAAGAAGAAGCTCTC (SEQ ID NO: 45) |
| GAPDH.F | AAGGTGAAGGTCGGAGTCAA (SEQ ID NO: 46) |
| GAPDH.R | GGAAGATGGTGATGGGATTT (SEQ ID NO: 47) |
| MALAT1.F | CGCAACTGGCCTCTCCTGCC (SEQ ID NO: 48) |
| MALAT1.R | CTCGTCGCTGCGTCCCAAGG (SEQ ID NO: 49) |
| NEAT1.F | GGGGCGGATCGGTGTTGCTT (SEQ ID NO: 50) |
| NEAT1.R | CCCGGTTCCATCTGCTCGCC (SEQ ID NO: 51) |

References Example 2

References

1. Jacob F, Monod J (1961) J Mol Biol 3:318-356.
2. Guttman M, et al. (2009) Nature 458:223-227. CrossRef-MedlineWeb of Science
3. Birney E, et al. (2007) Nature 447:799-816.
4. Mercer TR, et al., (2008) Proc Natl Acad Sci USA 105:716-721.
5. Ponting CP, Oliver P L, Reik W (2009) Cell 136:629-641.
6. Clark MB, et al. (2011) PLoS Biol 9:e1000625.
7. van Bakel H, et al., (2010) PLoS Biol 8:e1000371.
8. Lee JT (2009) Genes Dev 23:1831-1842
9. Gelbart ME, Kuroda M I (2009) Development 136:1399-1410.
10. Murakami K, et al., (2007) J Hum Genet. 52:926-933
11. Mohammad F, et al. (2008) Mol Cell Biol 28:3713-3728.
12. Pandey RR, et al. (2008) Mol Cell 32:232-246.
13. Nagano T, et al. (2008) Science 322:1717-1720.
14. Feng J, et al. (2006) Genes Dev 20:1470-1484
15. Shamovsky I. et al., (2006) Nature 440:556-560
16. Orom UA, et al. (2010) Cell 143:46-58
17. Martianov I, et al. (2007) Nature 445:666-670.
18. Schmitz KM, et al. (2010) Genes Dev 24:2264-2269
19. Rinn JL, et al. (2007) Cell 129:1311-1323.
20. Wang KC, et al. (2011) Nature 472:120-124.
21. Prasanth KV, et al., (2007) Genes Dev 21:11-42.
22. Taft RJ, et al., (2010) J Pathol 220:126-139
23. Gilbert C, Svejstrup J Q (2006) Curr Protoc Mol Biol, Chapter 27: Unit 27 24.
24. Darnell RB (2010) Interdiscip Rev RNA, HITS-CLIP: Panoramic views of protein-RNA regulation in living cells (Wiley, New York), Vol 1, pp 266-286.
25. Ule J, et al., (2005) Methods 37:376-386.26. Ule J, et al. (2003) Science 302:1212-1215
27. Tsai MC, et al. (2010) Science 329:689-693
28. Koziol MJ, Rinn J L (2010) Curr Opin Genet Dev 20:142-148.
29. Nagano T, Fraser P (2011) Cell 145:178-181.
30. Levsky JM, Singer R H (2003) J Cell Sci 116:2833-2838.
31. Carter D, et al., (2002) Nat Genet. 32:623-626.
32. Mariner PD, et al. (2008) Mol Cell 29:499-509.
33. Dejardin J, Kingston R E (2009) Cell 136:175-186.
34. Rinke J, et al., (1984) Nucleic Acids Res 12:4111-4126.
35. Wassarman D A, Steitz J A (1991) Mol Cell Biol 11:3432-3445.
36. Lingner J, et al. (1994) Genes Dev 8:1984-1998.
37. Stein H, Hausen P (1969) Science 166:393-395.
38. Ryder U, et al., (1990) Nucleic Acids Res 18:7373-7379.
39. Lingner J, Cech T R (1996) Proc Natl Acad Sci USA 93:10712-10717.
40. Hirsch JD, et al. (2002) Anal Biochem 308:343-357
41. Alekseyenko AA, et al. (2008) Cell 134:599-609.
42. Chen LL, Carmichael G G (2009) Mol Cell 35:467-478.
43. Clemson CM, et al. (2009) Mol Cell 33:717-726
44. Hutchinson JN, et al. (2007) BMC Genomics 8:39.
45. Saha S, et al., (2007) Brain Res 1148:38-42.
46. Sasaki YT, et al (2009) Proc Natl Acad Sci USA 106:2525-2530.
47. Sunwoo H, et al. (2009) Genome Res 19:347-359
48. Wilusz JE, et al., (2008) Cell 135:919-932.
49. Fox AH, Lamond A I (2010) Cold Spring Harb Perspect Biol 2:a000687
50. Spector DL, et al., (2011) Cold Spring Harb Perspect Biol 3:a000646
51. Mao YS, et al., (2010) Nat Cell Biol 13:95-101
52. Franke A, Baker B S (1999) Mol Cell 4:117-122.
53. Kelley RL, et al. (1999) Cell 98:513-522.
54. Meller VH, et al. (2000) Curr Biol 10:136-143.
55. Alekseyenko AA, et al., (2006) Genes Dev 20:848-857.
56. Gelbart ME, et al., (2009) Nat Struct Mol Biol 16:825-832.
57. Gilfillan GD, et al. (2006) Genes Dev 20:858-870.
58. Kind J, et al. (2008) Cell 133:813-828.
59. Smith ER, et al., (2001) J Biol Chem 276:31483-31486.
60. Hilfiker A, et al. (1997) EMBO J. 16:2054-2060
61. Larschan E, et al. (2011) Nature 471:115-118.
62. Straub T, et al., (2008) PLoS Genet. 4:e1000302.
63. Gorchakov AA, et al., (2009) Genes Dev 23:2266-2271.
64. Mosrin-Huaman C, et al., (1998) Dev Genet. 23:324-334.
65. Kharchenko PV, et al. (2011) Nature 471:480-485.
66. Chu C, et al. (2011) Mol Cell 44:667-648.

Example 3

Genome Yields Analogous Results

In differentiated female mammalian cells, the two X-chromosomes are not identical; one is coated by the Xist RNA and inactivated (referred to as the Xi) and one is not coated by Xist and is active (referred to as the Xa). Many studies have demonstrated that the Xist RNA is important for this process (reviewed in Lee et al. PMC2725936). While it is clear that the Xist RNA plays a role in X-chromosome inactivation and this role is connected to the localization of Xist on the X-chromosome, molecular characterization of the interactions of Xist with the X-chromosome have not been examined at the molecular level. Xist CHART would allow this level of characterization.

Give the role of Xist in establishment of the Xi, one would expect Xist CHART to enrich only sites on the Xi but not on the Xa. This notion was tested using a hybrid cell line that distinguishes the two copies of the X (the Xi and Xa) using allele specific variation. Xist CHART was performed under conditions very similar to those described for roX2 above. Briefly, the hybrid mouse embryonic fibroblast cell line was grow and crosslinked with formaldehyde. Nuclei were isolated from the crosslinked cells, and the chromatin was solubilzed (via Covaris). Capture oligonucleotides were designed using RNase H mapping that target regions of the Xist RNA within 5 kb of the 5'-end of the RNA. This region had been previously demonstrated to be important for Xist RNA localization. Using these capture oligonucleotides and conditions that were developed for roX2 CHART described above, Xist-associated DNA was enriched and analyzed.

Figure 19A:
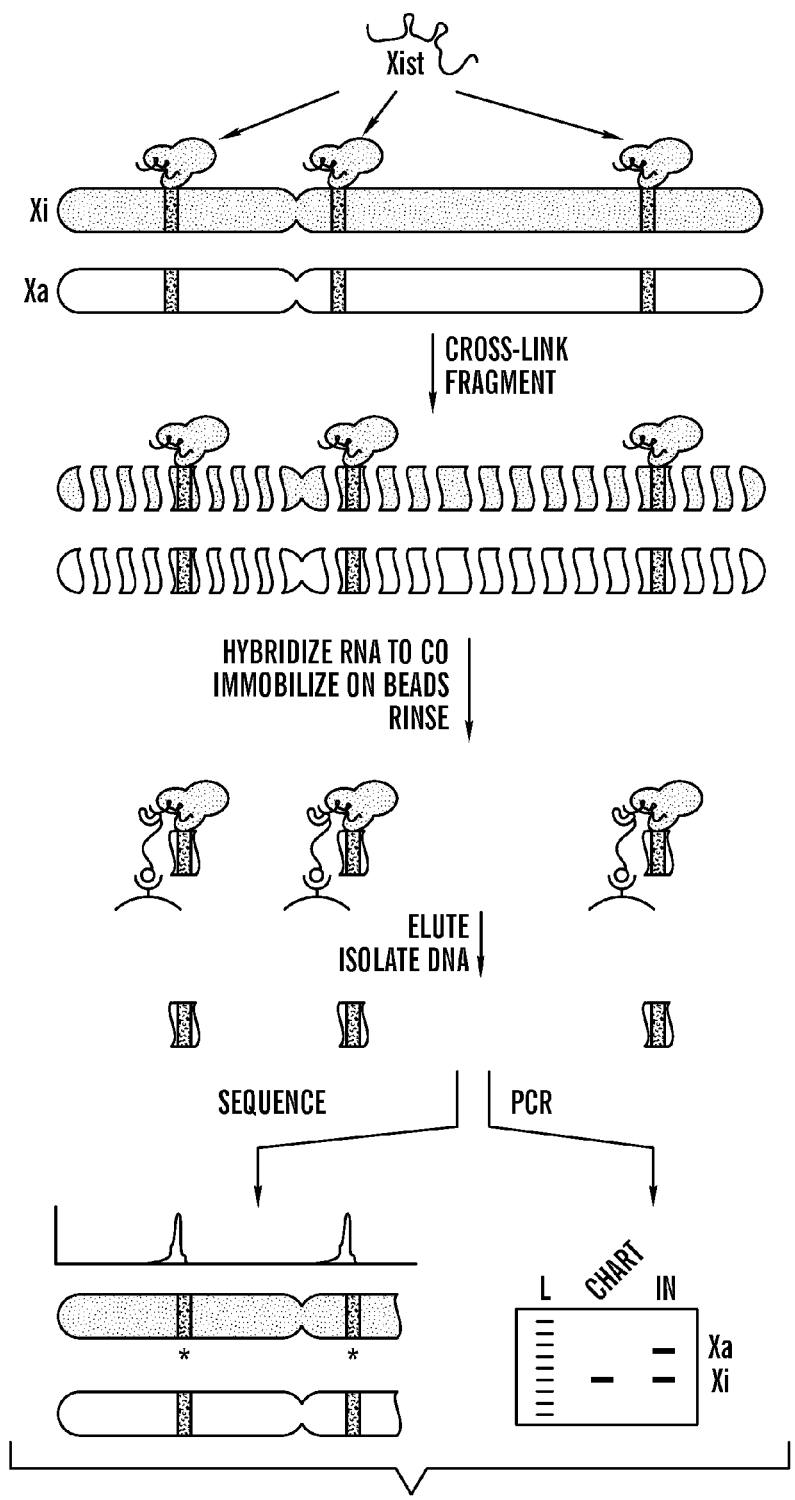

From these studies, we found that Xist CHART does indeed enrich for sites on the X-chromosome (FIG. 19), as expected given the role of Xist in dosage compensation. Furthermore, Xist CHART enriched regions on the Xi but not the Xa (FIG. 19) as could be found by performing PCR using primers that span a length polymorphism, thereby distinguishing sites on the Xi from the Xa. In support of the results shown here, deep sequencing of the samples generated in this experiment also demonstrated the expected enrichment across the X-chromosome.

This data verifies the advancement of the CHART technology into mammalian cells. These findings verify that in mammalian cells CHART is able to enrich sites on DNA where the RNA is bound (in this case Xist) that are far from the place in the genome where the RNA is transcribed. The data represents a reduction to practice of CHART on a mammalian RNA at trans-acting sites.

Based on the NEAT1 CHART discussed above, using NEAT1 and MALAT1, deep sequencing libraries were made from the CHART enriched samples. This further supports the notion that CHART is useful for enriching trans-acting sites of mammalian RNAs, as originally demonstrated in the above discussed data from Xist CHART.

2) The sequences of the capture oligos used (Xist CHART) were:

```
                                         (SEQ ID NO: 52)
X1.1:  CGC CAT TTT ATA GAC TTC TGA GCA GL-BIO (SEQ ID NO: 53)
X1.2:  CCC TTA AAG CCA CGG GGG ACC GCG CL-BIO (SEQ ID NO: 54)
X1.3:  CTC GGT CTC TCG AAT CGG ATC CGA CL-BIO
```

The design of the capture oligos above, including the single linker (L) and the TEG-Biotin (BIO) on these oligos were the same as was used above in the RNase H CHART experiments of example 2. C-oligos used for RNase-H-eluted capture hybridization analysis of RNA targets (CHART) were 3'-modified by a single oligoethyleneglycol spacer and biotin-TEG.

Example 4

The following describes various examples of the herein described methodology to map the location of these RNAs on the genome, a key step in understanding the function of these RNAs.

The genome is regulated by trans-acting factors that bind to specific loci in chromatin. In addition to protein factors, it has become clear that large non-coding RNAs can also act on chromatin at sites distant from where they are transcribed. This protocol describes a means of identifying the genomic targets of those large non-coding RNAs. To accomplish this, the endogenous RNA of interest (here Drosophila roX2 is used as an example) is enriched from crosslinked chromatin extracts using short biotinylated complementary oligodeoxyribonucleotides. The targets of the RNA can be determined by examining the proteins and DNA that are enriched under these conditions. This analysis can be extended genome-wide by subjecting the enriched DNA to deep sequencing.

Performing Capture Hybridization Analysis of RNA Targets (CHART)

This unit describes CHART (Capture Hybridization Analysis of RNA Targets), an experiment used to analyze RNA targets that is analogous to chromatin immunoprecipitation (ChIP, Unit 21.19) for proteins. Similar to a ChIP experiment, the factor of interest is enriched from crosslinked chromatin extracts. Whereas ChIP employs antibodies that recognize an accessible region on the protein of interest, CHART employs capture oligonucleotides are designed to specifically hybridize to the RNA of interest. Using these capture oligonucleotides, the RNA is enriched together with its targets. Similar to a ChIP experiment, the CHART-enriched DNA can be analyzed to determine where the RNA was bound in the genome.

While the principles that underlie CHART are general for large non-coding RNAs (lncRNAs), for clarity the protocol is presented here for purifying a specific RNA, roX2, from Drosophila cell extracts. BASIC PROTOCOL 1 describes the isolation of nuclei from Drosophila S2 cells but can also be applied to mammalian cell lines. BASIC PROTOCOL 2 describes using these nuclei to map the accessible regions of the RNA for the design of capture oligonucleotides. BASIC PROTOCOL 3 describes the use of these capture oligonucleotides to enrich roX2 along with its associated targets. To analyze these targets, BASIC PROTOCOL 4 describes the analysis of CHART-enriched DNA and proteins.

Basic Protocol 1.

Preparing Crosslinked Nuclei

CHART enrichment is performed using reversibly crosslinked (e.g., formaldehyde crosslinked) chromatin extracts. Formaldehyde serves to covalently connect the RNA to its biological targets at the time of crosslinking while the cells are still intact. As the chromatin-bound RNAs are found in the nucleus, it is beneficial (although not strictly necessary) to purify the nuclei from the cells prior to CHART analysis. Later in the protocol the nuclei will be subjected to further crosslinking with higher levels of formaldehyde (see BASIC PROTOCOL 3). If this higher degree of crosslinking were performed initially, it could interfere with isolation of nuclei. Therefore, the first steps described in this protocol are to perform low levels of formaldehyde crosslinking and to enrich the cell nuclei.

Materials

CCM3 medium (Hyclone, cat. SH30065.02).
Phosphate Buffered Saline (PBS)
Formaldehyde (16% w/v, 10 mL ampule, Thermo Scientific, cat. 28908)

Sucrose Buffer (see recipe)
Glass dounce homogenizer with tight pestal (15 mL)
Glycerol Buffer (see recipe)

Protocol

1. Grow Drosophila S2 cells in shaker flasks in serum-free CCM3 medium.

CHART experiments require similar quantities of starting material as ChIP experiments. Whether using insect cells such as the S2 cells described here, or mammalian cells, it is convenient to grow enough material to generate several cell pellets of $10^8$ cells/aliquot for mammalian cell lines, or $10^9$ cells/aliquot of insect cell lines. The minimum material required for a successful CHART experiment is around $2.5 \times 10^6$ cells but using $10^7$-$10^8$ cells per CHART enrichment is preferable, especially for deep sequencing of the enriched DNA.

2. Harvest by centrifugation (~$10^{10}$ cells, 500×g, 15 min), rinse once with PBS and resuspended in PBS (200 mL). For mammalian cell lines, it is convenient to crosslink $10^8$-$10^9$ cells.

3. Add formaldehyde to 1% final concentration and allow the suspension to rotate end-over-end (10 min, rt).

Other crosslinking protocols, including those that involve the addition of formaldehyde directly to the medium of a mammalian cell culture dish have also proven successful for CHART.

4. Capture the cells by centrifugation, rinse three times with cold PBS and use immediately or aliquot ($1 \times 10^9$ cells/aliquot). Prior to freezing, decant the PBS and flash freeze the pellet with liquid nitrogen and store at −80° C.

5. Resuspend one pellet ($1 \times 10^9$ S2 cells or $1 \times 10^8$ mammalian cells) in Sucrose Buffer (4 mL, on ice).

6. Transfer the suspension to an ice-cold dounce homogenizer. Dounce ten times with a tight pestle. Wait five minutes. Then dounce ten more times.

7. Add 4 mL of Glycerol Buffer to a 15 mL conical tube. Then add 4 mL of Glycerol Buffer to the mixture in the dounce homogenizer and mix by pipetting up and down several times. Carefully layer this solution of cell debris on top of the Glycerol Buffer in the 15 mL conical tube.

8. Centrifuge the tube (1000×g for 10 min, 4° C.) to pellet the nuclei.

9. Remove the supernatant using a pipette, taking care to pull off the upper layer with minimal mixing.

10. Repeat steps 5-9 one additional time.

This pellet of enriched nuclei can either be carried directly into the RNase H mapping protocol (BASIC PROTOCOL 2), or further crosslinked and used for CHART enrichment (BASIC PROTOCOL 3).

Basic Protocol 2.

Design of Capture Oligonucleotides that Target Accessible Regions of the RNA

The objective in this protocol is to design capture oligonucleotides that can hybridize specifically to the desired RNA, in this case roX2. In the context of crosslinked chromatin extracts, it is expected that some regions of the RNA will be more accessible for hybridization than others due to either secondary structure or steric occlusion by proteins. This protocol provides an example of a method for identifying the regions that are accessible for hybridization and designing capture oligonucleotides that target these regions.

A chromatin extract is made from the nuclei generated in BASIC PROTOCOL 1. Then candidate 20-mer synthetic DNA oligonucleotides are mixed one-at-a-time with this chromatin extract in the presence of an enzyme, RNase H, that hydrolyzes RNA at the sites of RNA-DNA hybrids. Oligonucleotides that hybridize to accessible sites in the RNA produce RNA-DNA hybrids and lead to enzymatic cleavage of the RNA. The degree of this RNase H sensitivity can be determined using RT-qPCR. Oligonucleotide sequences that lead to high RNase H sensitivity are used to design biotinylated capture oligonucleotides for CHART enrichment (BASIC PROTOCOL 3).

Materials

Nuclei pellet (from BASIC PROTOCOL 1)
Nuclei Wash Buffer (see recipe)
Sonication Buffer (see recipe)
Covaris S2 instrument (or other similar means of shearing DNA)
RNase H (NEB, 5 U/μL, cat. M0297L)
SUPERasIN (Ambion, AM2696)
20-mer oligonucleotides (IDT) For more information see Step 11.
DNase RQ1, (Promega, M6101)
Proteinase K (20 mg/mL, Ambion, AM2548)
PureLin Micro-to-Midi Total RNA Purification System (Invitrogen, cat. 12183-018)
Nanodrop spectrophotometer
SuperScript VILO cDNA Synthesis Kit (Invitrogen, cat. 11754-050)
ABI 7500 RT-PCR instrument or similar
iTaq SYBR Green Supermix with ROX (Bio-Rad, cat. 172-5850)
Appropriate qPCR primer sets Protocol 1. Resuspend the nuclei in Nuclei Wash Buffer (5 mL, on ice).

2. Centrifuge the tube (1000×g, 10 min, 4° C.) to pellet the nuclei.

3. Repeat steps 1 & 2 one additional time (two rinses total).

4. Resuspend pellet in 3 mL of Sonication Buffer and centrifuge as in step 2.

5. Resuspend the pellet to 3 mL final volume (—1.5 mL added buffer) of Sonication Buffer.

6. Process the nuclei using a Covaris instrument (30 min program, 10% duty cycle, intensity of 5, 4° C.) to make the chromatin soluble through fragmentation.

This assay has been successful using extract solubilized by different means, including Bransen sonication, and with average sheer sizes ranging from 200 bp-5 kb. It is likely that any instrument successfully used for ChIP experiments can be applied successfully (so long as it does not lead to RNase contamination of the extract, which is one advantage of using a non-invasive instrument like Covaris).

7. Separate the extract into four 1.7 mL tubes and clear the extract by centrifugation (16.1 k×g, 10 min, rt).

8. Separate the cleared extract into aliquots of 250 μL and continue to Step 9 immediately or flash freeze ($N_2$) and store at −80° C.

9. Set up a master mix (e.g., 36× master mix) of the following reagents:
   10 μL cleared extract (e.g., 360 μL)
   0.03 μL $MgCl_2$ (1 M stock) (e.g., 1.1 μL)
   0.1 μL DTT (1M stock) (e.g., 3.6 μL)
   1 μL RNase H (e.g., 36 μL)
   0.5 μL SUPERasIN (20 u/μL) (e.g., 18 μL)

10. In 8-strips of PCR tubes, add to each tube 10 μL master mix.

11. Add 1 μL of DNA oligo (100 pmol/μL stock) to each tube except for two controls where water should be used instead of a DNA oligonucleotide.

For a relatively short (~600 nt) RNA such as roX2, the majority of the RNA was tiled. However, for longer RNAs comprehensive tiling would be very resource intensive, and instead candidate regions are chosen based on the following criteria when information is available: (1) regions near conserved elements within the target RNA, (2) regions near known sites of protein interactions and (3) regions that have low repeat density. The tiled nucleotides are 20-mers that are complementary to the target RNA and overlap each other by 10 nt (e.g., Oligo 1 targets nucleotides 1-20; Oligo 2 targets nucleotides 10-30; Oligo 3 targets nucleotides 20-40; etc.) The DNA oligonucleotides used do not need to be purified beyond standard desalting.

12. Mix by pipetting up and down 20 times. Concentrate the liquid in the tubes by quick (~5 sec.) centrifugation.
13. Incubate in a PCR machine at 30° C. for 30 min.

A range of temperatures (30-37° C.) and times (30 min-1 hr) have been successfully employed.

14. Quick spin the tubes and add 1 μL of DNase master mix:
    1 μL per reaction RQ1 DNase (e.g., 40 μL)
    0.1 μL per reaction of 60 mM CaCl$_2$ (made from 6 μL 1 M stock into 94 μL ddH$_2$O) (e.g., 4 μL)
15. Incubate at 30° C. for 10 min.
16. Quick spin to capture all of the liquid and quench by adding 2 μL of freshly made quenching buffer into the cap, close, quick spin, mix by gentle flicking and quick spin once more.
    20 μL 0.5 M EDTA
    20 μL 1M Tris pH 7.2
    20 μL 20 mg/mL Proteinase K (added immediately before use)
    20 μL 10% SDS
17. Incubate in a PCR thermocycler for 60 min at 55° C.; then 30 min at 65° C.

This short crosslink reversal protocol saves time and works nearly as well as longer protocols. For modest increases in reversal efficiency, extend the 65° C. incubation 1-2 h.

18. Quick spin to capture the liquid. Purify RNA using PureLink RNA isolation kit according to the manufacture's directions. Include extra-on column DNase step. Elute the RNA into 30 μL ddH$_2$O.

Other companies' products have also been successfully used. Also note that the earlier DNase treatment (Step 14) is prior to crosslink reversal (Step 17), and therefore a second DNase treatment is included to remove DNA that was protected by crosslinking.

19. Determine the approximate concentration of RNA using a Nanodrop spectrophotometer.

This step is for quality control to ensure the RNA was not lost during handling. Usually the yield is between ~100-200 ng/μL.

20. Set up reverse transcription reactions as follows:
    2 μL 5×VILO master mix
    7 μL RNA solution from step 18.
    1 μL VILO RT enzyme (include one RT-)
21. Incubate as directed (25° C. 10 min.; 42° C. 60 min.; 85° C. 5 min.; 4° C. forever).
22. Dilute the RT reactions with ddH$_2$O (10 μL).
23. Analyze by qPCR using a ABI 7500 RT-PCR instrument and iTaq SYBR Green Supermix with ROX (the dye, unrelated to roX2).
    12.5 μL Supermix (need about 1.25 mL/plate)
    10.5 μL of primer mix (3 μL ea. primer into 420 μL H2O)
    2 μL of RT reaction (use multichannel)
    (94° C. 5 min. 40 cycles of [94° C. 30", 52° C. 30", 72° C. 1']).

For each RNase H reaction, analyze using at least three primer sets: (1) a primer set that amplifies a region of the target cDNA that includes the oligo probe, (2) a control primer set for an unrelated RNA (e.g., Act-5C transcript) to normalize input levels and (3) a control primer set outside the putative region of sensitivity but part of the target cDNA.

24. Analyze results with the following formula:

$$RNase\ H\ Sensitivity = \left( \frac{efficiency_{TARGET\ PRIMERS}^{C_{T,olgio}-C_{T,no\ oligo}}}{efficiency_{CONTROL\ PRIMERS}^{C_{T,olgio}-C_{T,no\ oligo}}} \right)$$

The locations of the peaks in sensitivity are robust, but the numerical sensitivities vary. This is acceptable because only the relative (and not the absolute) sensitivity is important. The efficiencies for each primer set can either be determined experimentally (as in Simon et al., fig S1A) or approximated as ~2.

25. Analyze the peaks from RNase H mapping, focusing on regions where two or more consecutive oligonucleotides induce sensitivity. Optimize a 24-25 nt sequences by BLAST for specificity in the genome and against off-target RNAs. Generally calculated melting temperatures between 58° C. and 65° C. is optimal.

Determining the relative importance of various capture oligonucleotide design parameters is ongoing; the optimization of these parameters will be established as CHART is applied to more RNAs.

26. Use these sequences to synthesize oligonucleotides of the form: [OLIGO SEQ]-L-BIO, where L represents a C18-spacer, and BIO is 3'-biotin TEG. These oligonucleotides can be ordered commercially.

Using 3'-modified oligonucleotides (as opposed to 5'-modified oligonucleotides) is preferable because the modifications will block the capture oligonucleotides from unwanted participation in downstream library preparation steps.

27. Make working dilutions of the capture oligonucleotide cocktails at 300 pmol/μL of each oligo.

Basic Protocol 3.
Performing Chart Enrichment

The capture oligonucleotides from BASIC PROTOCOL 2 can be used to enrich the target RNA from crosslinked chromatin extracts. For optimal enrichment, the chromatin extract is made using nuclei that are crosslinked to a greater extent than traditional ChIP protocols. Therefore the first part of this protocol is formaldehyde treatment of the nuclei. The chromatin is then sheered into smaller fragments, and the capture oligonucleotides are added under hybridization conditions. These conditions are optimized to maintain high solubility of the chromatin extract, and balance high yields of the desired RNA with the necessary stringency to avoid hybridization-induced artifacts. After capturing and rinsing the desired RNA with its targets, the bound material is eluted enzymatically.

Materials
  Nuclei pellet from 1×10⁹ cells (BASIC PROTOCOL 1)
  1×PBS (pH 7.4) (Appendix 2)
  Formaldehyde (16% w/v, 10 mL ampules, Thermo Scientific, cat. 28908)
  Wash Buffer 100 (WB100, see recipe)
  SUPERasIN (20 u/μL, Ambion, AM2696)
  Roche complete EDTA-free protease inhibitor cocktail
  Denaturant Buffer (see recipe)
  2× Hybridization Buffer (see recipe)
  MyOne Dynabeads C1 (Invitrogen, cat. 650.02)
  Dynal magnets for 1.7 mL tubes.
  Wash Buffer 250 (WB250, see recipe)
  RNase H Elution Buffer (HEB, see recipe)
Protocol
1. Thaw a pellet of nuclei from BASIC PROTOCOL 1 on ice.
2. Rinse the pellet twice with PBS (10 mL) using centrifugation (1000×g, 10 min) to capture the nuclei between each rinse. Use the rinses to transfer the nuclei to a 50 mL conical.
3. Resuspend in PBS (40 mL) and add formaldehyde (entire 10 mL ampule). Rotate the tube for 30 min. at room temperature.
4. Centrifuge (1000×g, 10 min, 4° C.) to collect the nuclei and resuspend in 50 mL of PBS.
5. Centrifuge (1000×g, 5 min, 4° C.) to collect the nuclei and transfer to a 15 mL conical tube using two times 5 mL of PBS (10 mL total).
6. Centrifuge (1000×g, 5 min, 4° C.) to collect the nuclei and rinse twice with WB100.
7. Resuspend the nuclei at to 3 mL final volume of WB100 supplemented with SUPERasIN (20 u/mL final) and protease inhibitors.
8. Sonicate the nuclei at power level 5-6 (holding the output between 30-40 W) for 10 min total process time (15" on, 45" off) in ice bath.
  We have also had success using Covaris to fragment the chromatin. These conditions should be determined empirically.
9. Separate into six 1.7 mL tubes and clear the extract by centrifugation (16,100×g, 20 min, 4° C.).
10. Aliquot the cleared extract (250-500 μL aliquots) and either continue directly to Step 11 or flash freeze (N₂) and store at −80° C.
11. Use 500 μL of extract from STEP 10.
12. Supplement the extract with:
  10 μL SUPERasIN
  5 μL DTT (1M)
  5 μL 100× protease inhibitors
13. Add 250 μL of Denaturant Buffer.
14. Add 750 μL of 2× Hybridization Buffer.
15. For each CHART experiment, use ~400 μL, which leaves enough for the roX2 CHART, the sense control, and a no-oligo control (from which the supernatant can act as an input control). Add 54 pmol (2.7 μL of a 20 μM CHART capture oligo cocktail BASIC PROTOCOL 2) for every 100 μL of extract (i.e., 10.8 μL/400 μL extract). Mix thoroughly with a pipette.
  Depending on the oligo cocktail, there is room for optimization of the concentrations of individual capture oligonucleotides in the cocktail, and also the total concentration of capture oligonucleotides (ranging from 10-50 μM stocks at the volumes listed above).
  A good controls for CHART experiments is to perform the experiment using the sense oligo control, in which the sequence of the oligonucleotides are of the wrong strand to hybridize to the target RNA. Other possible controls include using scrambled oligo controls, or using oligos directed against an unrelated RNA. Using a sense oligo control has the advantage that any artifactual signal caused by direct interactions between the capture oligos and the DNA will also be detected in the sense oligo control and can therefore be subtracted bioinformatically.
16. Incubate at room temperature for 6-12 h.
17. Centrifuge (16,100×g, 10 min, rt) to clear hybridization reaction. Transfer the supernatant to a fresh tube.
  It is important that the centrifuge does not heat the samples. Therefore a temperature controlled centrifuge should be used.
18. Repeat Step 14 one more time.
  It is important to remove small amounts of precipitation that form during the hybridization step as this precipitation can dramatically increase background in the CHART experiment.
19. Pre-rinse 150 μL MyOne Dynabeads with two times 500 μL ddH₂O using the magnetic stand to capture the beads in between rinses.
20. Resuspend beads in 100 μL ddH₂O and then add 50 μL Denaturant Buffer.
21. Add the cleared extract from Step 14 to the bead mixture and incubate overnight rotating gently end over end.
22. Capture the beads using a magnet and save the supernatant from the no-oligo control for later analysis.
  The supernatant from a no-oligo control makes for a good control since it takes into account any composition changes during handling of the samples.
23. Quick spin the bead suspension, resuspend the beads completely by pipette.
24. Transfer 150 μL of the bead solution into three fresh tubes, each containing 750 μL of WB250.
25. Capture with the beads with a Dynal magnet and wash three times with 750 μL WB250, completely resuspending the beads with gentle inversion between each mix.
26. Use 3×200 μL of HEB to transfer the combined bead mixtures in a fresh 1.7 mL tube.
27. Capture the beads, remove the majority of the supernatant, centrifuge the tubes briefly (1000×g, 5 sec), replace the tubes in the magnet and remove the residual liquid.
28. Remove the tubes from the magnet and add 100 μL freshly made HEB, resuspending the beads gently by pipette.
29. To elute the CHART-enriched material, add 2 μL RNase H, flick gently and incubate at room temperature for 10 min at rt.
  Make sure the RNase H is highly active (i.e., relatively new). The enzyme can lose activity upon handling; if the enzyme is insufficiently active, preventing elution and thereby dramatically reducing the CHART yields.
30. Centrifuge the tubes briefly (1000×g, 5 sec), and capture the beads.
31. Transfer the supernatant to a fresh tube and either process immediately or flash freeze in liquid nitrogen and store at −80° C.

Basic Protocol 4.

Preparation of Target DNA, RNA and Proteins from Chart Enrichment

The material resulting from CHART enrichment (BASIC PROTOCOL 3) is a crosslinked mixture of biomolecules consisting of the RNA of interest and its interacting partners, including its DNA and protein targets. Depending on the purpose of the experiment, the eluted material may be used for analysis of the enriched DNA, RNA or proteins. This protocol describes the handling of CHART enriched material to prepare it for standard analyses such as quantitative PCR or western blot analysis. This protocol also describes how to prepare the DNA for analysis by deep sequencing.

Materials
CHART enriched eluant (BASIC PROTOCOL 3)
Proteinase K (20 mg/mL, Ambion, AM2548)
Nucleic Acid XLR Buffer (see recipe)
Phenol:CHCl$_3$:isoamyl alcohol 25:24:1 Saturated with 10 mM Tris, pH 8.0, 1 mM EDTA (Sigma, cat. P3803)
Phaselock tubes (5 prime, cat. 2302800)
CHCl$_3$ (Fluka, cat. 25668)
GlycoBlue (Ambion, AM9515)
Kimwipes
MicroTube (6×16 mm) AFA Fiber with Snap-Cap round bottom glass tube (Covaris, cat. 520045)
PureLink Micro-to-Midi Total RNA Purification System (Invitrogen, cat. 12183-018)
VILO Reverse-transcription cDNA synthesis kit (Invitrogen, cat. 11754-050)
iTaq SYBR Green Supermix with ROX (Bio-Rad, cat. 172-5850)
ABI 7500 qPCR Instrument
Appropriate primer sets
Lane Marker Non-Reducing Sample Buffer (Pierce, cat. 39001)

For Preparation of CHART Enriched Nucleic Acids:
1. To remove proteins and crosslinks for analysis of the CHART enriched nucleic acids use 100 µL of the eluant, and add 25 µL Nucleic Acid XLR Buffer. Include an additional tube for analysis of the input. Note that the crosslink reversal for the purposes of analyzing the enriched proteins is described in the Protein analysis protocol below and requires a different crosslink reversal solution.
   Generally it is convenient to dilute the input sample to 10% equivalents in elution buffer.
2. Heat to 55° C. for 1 h and then to 65° C. for 30 min. For genome-wide mapping experiments, it is convenient to use 100 µL for analysis of DNA (Step 3a-13a) and the remaining 25 µL for analysis of the RNA (Step 3b-8b).

To Prepare DNA for Deep Sequencing:
3a. Dilute 100 µL of material from Step 2 into 100 µL of ddH$_2$O in a 1.5 mL phaselock tube and 200 µL of Phenol:CHCl$_3$:isoamyl alcohol.
4a. Shake vigorously and centrifuge (12,000×g, 5 min).
5a. Rinse the aqueous layer twice with 100 µL CHCl$_3$.
6a. Transfer 200 µL of the aqueous solution to a fresh tube and add 10 µL NaOAc (3M, pH 5.5) and 1 µL GlycoBlue. Then add 500 µL EtOH, vortex and incubate overnight at −20° C.
7a. Pellet the nucleic acids by centrifugation (16,000×g, 20 min., 4° C.).
8a. Carefully remove the supernatant and rinse the pellet with 500 µL of 70% EtOH.
   For longer-term storage, keep pellet in the 70% EtOH rinse at −80° C.
9a. Remove all of the liquid, air dry for 5 min. at room temperature with the tube covered by a Kimwipe.
10a. Resuspend the pellet in 100 µL of Tris buffer (10 mM, pH 8.0).
11a. Transfer the liquid to a MicroTube for Covaris.
12a. To reduce the average fragment size to 200-500 bp, process the tube by Covaris under the following conditions.
   DUTY CYCLE: 5%
   INTENSITY: 5
   CYCLES/BURST: 200
   TIME: 60 sec. (4 min program)
   BATH TEMP 4° C.
13a. Use this sheered material directly for library construction (e.g., UNIT 21.19, BASIC PROTOCOL 2).

To Prepare CHART Enriched RNA for RT-qPCR Analysis
3b. Purify 25 µL the CHART enriched, crosslink reversed RNA (Step 2) and input sample as a control using a standard purification kit (e.g., PureLink, Invitrogen). Include an on-column DNase digestion step.
4b. Set up reverse transcription reactions as follows:
   2 µL 5×VILO master mix
   7 µL RNA solution from Step 3b.
   1 µL VILO RT enzyme (include one without enzyme as an RT-minus control)
5b. Incubate as instructed (25° C. 10 min.; 42° C. 60 min.; 85° C. 5 min.; 4° C. forever).
6b. Dilute the reverse transcription reactions with ddH$_2$O (30 µL).
7b. Analyze by qPCR using a ABI 7500 RT-PCR instrument and BIO-RAD iTaq SYBR Green Supermix with ROX (the dye, unrelated to roX2).
   12.5 µL Supermix (need about 1.25 mL/plate)
   7.5 µL of primer mix (3 µL ea. primer into 300 µL H2O)
   5 µL of RT reaction (use multichannel pipette to add and mix)
   (94° C. 5 min. 40 cycles of [94° C. 30", 52° C. 30", 72° C. 1']).
8b. Calculate yields as follows:

$$\text{Yield} = \left( \frac{\text{Input dilution factor}}{\text{efficiency}_{PRIMERS}^{C_{T,CHART} - C_{T,INPUT}}} \right)$$

The efficiencies for each primer set can be determined experimentally (the values should be ~2). Given the high yields of roX2 recovered by CHART, it is convenient to use an input that is diluted to 10% equivalents.

Support Protocol: Analysis of CHART-Enriched Proteins
Materials
Protein XLR Buffer (see recipe)
Sample loading buffer (Pierce, cat. 39001)
Experiment
1. Transfer 20 µL of CHART enriched material from BASIC PROTOCOL 3 into a PCR tube.
2. Add 5 µL of Protein XLR Buffer.
3. Heat to 95° C. for 1 h in a PCR block and then cool to room temperature.
   This step reverses the crosslinks. Make sure to use a heated lid to avoid drying the samples.
4. Add 7.5 µL of Sample loading buffer (e.g., Pierce Non-Reducing Sample Buffer) and perform western blot analysis under standard conditions (e.g., UNIT 10.8).
   Note that the final salt concentration is reasonably high in these samples. Therefore, the input samples should be diluted in a buffer of similar salt to ensure that the lanes of the gel run evenly during PAGE analysis.

Support Protocol: Quality Control of CHART DNA Enrichment by qPCR.
Materials
iTaq SYBR Green Supermix with Rox (Bio-Rad, cat. 172-5850)
ABI 7500 qPCR Instrument
Appropriate primer sets Experiment CHART enrichment should be analyzed both before and after library construction by qPCR. Before library construction, the data is analyzed as yield relative to input:

$$\text{Yield} = \left( \frac{\text{Input dilution factor}}{\text{efficiency}_{PRIMERS}^{C_{T,CHART} - C_{T,INPUT}}} \right)$$

After library construction, the diluted libraries in triplicate using primers that will amplify known or expected binding sites (e.g., the endogenous roX2 locus and CES-5C2), and negative controls (e.g., Pka and Act-5C). Include a library constructed from the input. Note that the $C_T$ values for the input with different primers should be very similar to each other (within 1-2 $C_T$ values). Normalize the signal to input and to one of the negative control (e.g., Act-5C, which was used because amplification of the PKA was undetected for all three replicates in the roX2 CHART enriched samples):

$$\text{Fold enrichment} = \left( \frac{\text{efficiency}_{TARGET\ PRIMERS}^{C_{T,CHART} - C_{T,INPUT}}}{\text{efficiency}_{ACT-5C\ PRIMERS}^{C_{T,CHART} - C_{T,INPUT}}} \right)$$

It is not rare that the CHART enriched library has undetectable levels of one of the negative controls. A conservative estimate of the enrichment can be made by entering $C_T$ values of 40 in cases where no amplification is observed after 45 cycles.

Reagents and Solutions

Glycerol Buffer (500 mL)
  25% Glycerol (125 mL neat)
  10 mM HEPES pH 7.5 (5 mL of 1 M)
  1 mM EDTA (1 mL of 0.5 M)
  0.1 mM EGTA (50 µL of 1 M)
  100 mM KOAc (16.7 mL of 3 M stock)
  Immediately before use, add to 40 mL:
    0.5 mM Spermidine (200 µL of 0.1M, aliquoted −80° C.)
    0.15 mM Spermine (60 µL of 0.1M, aliquoted −80° C.)
    400 µL Complete EDTA-free Protease Inhibitor (from 100× stock)
    1 mM DTT (40 µL of 1M)
    200 u SUPERasIN (20 µL of 20 u/µL)

Sucrose Buffer (500 mL)
  0.3 M Sucrose (51.3 g solid)
  1% Triton-X (50 mL of 10% Stock)
  10 mM HEPES 7.5 (5 mL 1 M)
  100 mM KOAc (16.7 mL 3M stock)
  0.1 mM EGTA (50 µL of 1M)
  100 mM KOAc (16.7 mL of 3M stock)
  Immediately before use, add to 20 mL:
    0.5 mM Spermidine (100 µL of 0.1M, aliquoted −80° C.)
    0.15 mM Spermine (30 µL of 0.1M, aliquoted −80° C.)
    200 µL Complete EDTA-free Protease Inhibitor (from 100× stock)
    1 mM DTT (20 µL of 1M)
    200 u SUPERasIN (10 µL of 20 u/µL)

Nuclei Rinse Buffer (100 mL)
  50 mM HEPES pH 7.5 (5 mL 1M)
  75 mM NaCl (1.5 mL 5M)
  0.1 mM EGTA (20 ul of 0.5M)
  Immediately before use dilute 0.5 mL into 4.5 mL $H_2O$, add:
    200 u SUPERasIN (5 µL of 20 u/µL)
    1 mM DTT (5 µL of 1 M DTT)
    50 µL of 100× protease inhibitors Sonication Buffer (10 mL)
  50 mM HEPES pH 7.5 (500 µL 1M)
  75 mM NaCl (150 µL 5M)
  0.1 mM EGTA (2 ul of 0.5M)
  0.5% N-Lauroylsarcosine (1 mL, 5%)
  0.1% Sodium deoxycholate (100 µL, 10%)
  Immediately before use add (to 5 mL):
    100 u SUPERasIN (5 µL of 20 u/µL)
    5 mM DTT (25 µL of 1 M DTT)

Wash Buffer 100 (WB100, 50 mL)
  100 mM NaCl (1 mL of 5M stock)
  10 mM HEPES pH 7.5 (500 µL of 1M)
  2 mM EDTA (200 µL of 0.5M stock)
  1 mM EGTA (100 µL of 0.5M stock)
  0.2% SDS (1 mL of 10% stock)
  0.1% N-lauroylsarcosine (1 mL of 5% stock)
  Immediately before use:
    Add 100 µL PMSF (0.4 mM stock)
    Filter (0.22 µm)

Wash Buffer 250 (WB250, 50 mL)
  Same as WB100 except with 250 mM NaCl.

Denaturant Buffer
  8 M Urea
  200 mM NaCl
  100 mM HEPES pH 7.5
  2% SDS

2× Hybridization Buffer
  1.5 M NaCl
  1.12 M Urea
  10×Denhardt's Solution
  10 mM EDTA RNase H-elution Buffer (HEB, 2 mL)
  50 mM HEPES pH 7.5 (100 µL 1M)
  75 mM NaCl (30 µL 5M)
  0.125% N-Lauroylsarcosine (0.1 mL, 5%)
  0.025% Sodium deoxycholate (4 µL, 10%)
  40 u SUPERasIN (2 µL of 20 u/µL)
  10 mM DTT (20 µL of 1 M DTT)

Nucleic Acid XLR Buffer (400 µL)
  100 µL Tris 7.5 (1M Stock)
  100 µL SDS (10% Stock)
  200 µL Proteinase K solution (20 mg/mL)

Protein XLR Buffer (200 µL)
  67 µL Tris pH 8.8 (1.5M Stock)
  100 µL SDS (10% Stock)
  33 µL β-mercaptoethanol Discussion There are a growing number of large non-coding RNAs (lncRNAs) that have been implicated in the regulation of chromatin (Koziol and Rinn, 2010). One important goal is to determine the targets of these RNAs, including where they directly act in the genome. To this end, there has been substantial interest in using hybridization based approaches to map the targets of RNAs (Carter et al., 2002; Chu et al., 2011; Mariner et al., 2008; Simon et al., 2011). The advantage to the CHART protocol described here is the minimization of hybridization-induced artifacts by (1) targeting accessible regions of the RNA, and (2) avoiding extensive denaturation of the DNA. The conditions described here allow the isolation of both protein and DNA targets of an RNA, and can be extended to genome-wide mapping of the binding sites of a lncRNA (Simon et al., 2011).

Critical Parameters and Troubleshooting

The CHART reaction conditions have been carefully optimized to provide high yields of the desired RNA with its targets. Important parameters include the concentration of the extract, the level of crosslinking, the ionic strength and the concentration of urea. Using concentrated extracts improve CHART yield. Lower levels of crosslinking (as those used in ChIP) lead to low yields of DNA. The high ionic strength of the CHART conditions produces high yields, but higher ionic strength leads to precipitation of the chromatin. The high concentration of urea in the hybridization conditions maintains chromatin solubility and to provide the necessary stringency. The resolution of the experiment is determined by the shear size of the input chromatin. However, since the target RNA can also be sheared, a balance needs to be maintained between high-levels of shearing of the chromatin that increases resolution but might decrease CHART yield, and lower levels of shearing that may increase CHART yield but decreases the resolution of the experiment.

While CHART is optimized to avoid hybridization-induced artifacts, care still should be taken at each step to minimize likely artifacts. For example, it is important to use algorithms such as BLAST to avoid capture oligonucleotides that have the potential to base pair with off-target RNAs (i.e., avoid sequences with >14 nt matches to other expressed RNAs). One effective strategy to control for off target effects has been to use independent cocktails of capture oligonucleotides (Chu et al., 2011). In genome-wide data, artifacts tend to have sharp peaks and occur at genomic sites with high homology to either the capture oligonucleotide or the target RNA. Therefore care must be taken when interpreting peaks that meet these criteria.

Anticipated Results

In a successful CHART experiment, target RNA yields ranged from 5-50%. The corresponding DNA yields ranged from 0.1-2% which is also similar to the yields of tightly bound proteins. The enrichment values determined by comparing enriched loci with control loci were similar to ChIP, ranging up to thousands of fold. As the yields and enrichment were similar to ChIP, successful CHART experiments require a similar scale ($10^7$-$10^8$ cells/experiment).

Time Considerations

Starting from a cell pellet, the capture oligonucleotides were designed within approximately two days of work: one day for extract preparation and one day for RNase H mapping and oligonucleotide design. Once the capture oligonucleotides were obtained, CHART enrichment were performed in three partial days of work: one day for extract preparation and initiation of the hybridization reactions, one day for the addition of the beads and one day for washing the beads, elution, crosslink reversal and DNA analysis.

REFERENCES

Example 4

Carter, D., Chakalova, L., Osborne, C. S., Dai, Y. F., and Fraser, P. (2002). Long-range chromatin regulatory interactions in vivo. Nat Genet. 32, 623-626.

Chu, C., Qu, K., Zhong, F. L., Artandi, S. E., and Chang, H. Y. (2011). Genomic maps of long noncoding RNA occupancy reveal principles of RNA-chromatin interactions. Mol Cell 44, 667-678.

Koziol, M. J., and Rinn, J. L. (2010). RNA traffic control of chromatin complexes. Curr Opin Genet Dev 20, 142-148.

Mariner, P. D., Walters, R. D., Espinoza, C. A., Drullinger, L. F., Wagner, S. D., Kugel, J. F., and Goodrich, J. A. (2008). Human Alu RNA is a modular transacting repressor of mRNA transcription during heat shock. Mol Cell 29, 499-509.

Simon, M. D., Wang, C. I., Kharchenko, P. V., West, J. A., Chapman, B. A., Alekseyenko, A. A., Borowsky, M. L., Kuroda, M. I., and Kingston, R. E. (2011). The genomic binding sites of a noncoding RNA. Proc Natl Acad Sci USA 108, 20497-20502.

The invention claimed is:

1. A method for identifying a target nucleic acid sequence comprised within chromatin that associates with a known ribonucleic nucleic acid (RNA) sequence comprising the steps:
   (a) determining one or more oligonucleotide sequences for use in a capture probe for the known RNA sequence by:
      i) preparing a reversibly cross-linked chromatin extract;
      ii) providing candidate oligonucleotides between 15 and 25 nucleotides in length that are each complementary to a separate region of the known RNA sequence;
      iii) separately combining each of the candidate oligonucleotides of step ii) with the reversibly cross-linked chromatin extract, in the presence of RNase H, under conditions suitable for RNA-DNA hybridization and RNA hydrolysis of RNA-DNA hybrids, to thereby produce a chromatin-oligonucleotide mixture;
      iv) hydrolyzing DNA present in the chromatin-oligonucleotide mixture;
      v) purifying RNA from the chromatin-oligonucleotide mixture;
      vi) measuring RNAse H sensitivity; and
      vii) identifying a candidate oligonucleotide as a sequence for use in a capture probe when RNAse H sensitivity in step vi) is detected;
   (b) obtaining a sample that comprises the target nucleic acid sequence and the known RNA sequence in a reversibly cross-linked chromatin extract purified from reversibly cross-linked nuclei;
   (c) contacting the sample with one or more capture probes having an oligonucleotide sequence determined by step (a), wherein the capture probes comprise the oligonucleotide sequence and at least one affinity label, and wherein the capture probes specifically hybridise with the known RNA sequence;
   (d) providing conditions that allow the one or more capture probes to hybridise with the known RNA sequence so as to form a hybridization complex comprising the capture probe, the known RNA sequence and the target nucleic acid sequence;
   (e) isolating the hybridization complex by immobilising the hybridization complex via a molecule that interacts with the affinity label; and
   (f) analyzing the constituents of the isolated hybridization complex so as to identify the target nucleic acid sequence.

2. The method of claim 1, wherein the target nucleic acid sequence is located in genomic DNA, within a gene, or within a regulatory sequence.

3. The method of claim 1, wherein the regulatory sequence is within a promoter, a coding region, or a non-coding region.

4. The method of claim 1, wherein the known RNA sequence that is associated with the target nucleic acid sequence is a ncRNA or an mRNA.

5. The method of claim 1, wherein the one or more capture probes comprise DNA and/or at least one modified nucleotide analogue.

6. The method of claim 1, wherein the affinity label is selected from the group consisting of: biotin or an analogue thereof; digoxigenin; fluorescein; dinitrophenol; and an immunotag.

7. The method of claim 1, wherein the hybridization complex is immobilized through a molecule that binds to the at least one affinity label and which molecule is attached to a solid substrate.

8. The method of claim 1, wherein the conditions that allow the one or more capture probes to hybridise with the at least one RNA sequence in step (d) comprise:
  (a) a salt concentration selected of from about 100 mM to about 1.5 M, wherein the salt used is one or more of sodium chloride, sodium acetate, tetra-alkylammonium salts, lithium chloride, ammonium acetate, and cesium chloride; and
  (b) a concentration of a denaturant compound within a range of about 0.5M to about 5 M, wherein the denaturant used is one or more of urea, formamide, dimethylsulfoxide, guanidine hydrochloride, and dimethylformamide.

9. The method of claim 1, wherein step iii) is performed in 3 mM MgCl12, 10 mM DTT, 100 pmol oligonucleotide.

10. The method of claim 1, wherein hydrolyzing step iv) is by adding DNase and adjusting the reaction mixture to 500 uM $CaCl_2$.

11. The method of claim 1, wherein the reversibly cross-linked chromatin extract of step (a) is prepared by formaldehyde cross-linking.

12. The method of claim 1, wherein the reversibly cross linked chromatin extract and the reversibly cross-linked nuclei of step b) are prepared by formaldehyde cross-linking.

13. The method of claim 1, wherein measuring RNAse H sensitivity of step (a) vi) is by performing RT-qPCR on the RNA obtained in step (a) v).

14. The method of claim 1 further comprising further analyzing the constituents of the isolated hybridization complex so as to identify one or more additional factors associated with the target nucleic acid sequence.

15. The method of claim 14, wherein the one or more additional factors comprise at least one non-coding RNA (ncRNA) with or without a polypeptide, and/or at least one messenger RNA (mRNA) with or without a polypeptide.

* * * * *